(12) United States Patent
Wang et al.

(10) Patent No.: US 10,487,309 B2
(45) Date of Patent: Nov. 26, 2019

(54) INCORPORATION OF PLANT VIRUS PARTICLES AND POLYMERS AS 2D AND 3D SCAFFOLDS TO MANIPULATE CELLULAR BEHAVIORS

(71) Applicants: Qian Wang, Columbia, SC (US); Lim Andrew Lee, Columbia, SC (US)

(72) Inventors: Qian Wang, Columbia, SC (US); Lim Andrew Lee, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

(21) Appl. No.: 15/424,064

(22) Filed: Feb. 3, 2017

(65) Prior Publication Data

US 2017/0175079 A1    Jun. 22, 2017

Related U.S. Application Data

(62) Division of application No. 14/062,059, filed on Oct. 24, 2013, now abandoned.

(60) Provisional application No. 61/795,736, filed on Oct. 24, 2012.

(51) Int. Cl.
*C12N 7/00* (2006.01)
*C12N 5/00* (2006.01)

(52) U.S. Cl.
CPC ............. *C12N 5/0068* (2013.01); *C12N 7/00* (2013.01); *C12N 2501/11* (2013.01); *C12N 2501/115* (2013.01); *C12N 2501/15* (2013.01); *C12N 2533/50* (2013.01); *C12N 2770/00031* (2013.01)

(58) Field of Classification Search
None
See application file for complete search history.

(56) References Cited

U.S. PATENT DOCUMENTS

| 6,060,317 | A | 5/2000 | Malech |
| 6,503,732 | B1 | 1/2003 | Fitchen et al. |
| 7,928,290 | B2 | 4/2011 | Rasochova |
| 2009/0029441 | A1* | 1/2009 | Wang ................. B82Y 5/00 435/235.1 |
| 2009/0053261 | A1* | 2/2009 | Lindbo ................ A61K 39/12 424/199.1 |
| 2010/0112072 | A1* | 5/2010 | Wang .................. A61K 9/5138 424/490 |

(Continued)

FOREIGN PATENT DOCUMENTS

KR    20120095562 A  *  8/2012
WO    WO 2009120895 A2    10/2009

OTHER PUBLICATIONS

Omidian et al., "Elastic, Superporous Hydrogel Hybrids of Polyacrylamide and Sodium Alginate," Macromolecular Bioscience 6: 703-710 (2006).*

(Continued)

*Primary Examiner* — M Franco G Salvoza
(74) *Attorney, Agent, or Firm* — Dority & Manning, P.A.

(57) ABSTRACT

Methods are generally disclosed for attaching a cell binding motif to a carboxy end of a coat protein of a Tobacco Mosaic Virus particle to form a modified-TMV particle; and attaching a cell to the cell binding motif of the modified-TMV particle. Methods are also disclosed for incorporated virus particles, e.g., TMV virus particles into hydrogels.

21 Claims, 27 Drawing Sheets

Specification includes a Sequence Listing.

(56) References Cited

U.S. PATENT DOCUMENTS

2014/0234359 A1* 8/2014 Newell ............... A61K 39/12
424/186.1

OTHER PUBLICATIONS

Lee et al., "Alginate: properties and biomedical applications" Prog Polym Sci 37(1): 106-126 (2012).*
KR 20120095562 A (Google Translation in English)(2012).*
Lewis et al., "Microfluidic Fabrication of Hydrogel Microparticles Containing Functionalized Viral Nanotemplates," Langmuir 26(16): 13436-13441 (Year: 2010).*
Bolisay et al., "Molecularly imprinted polymers for tobacco mosaic virus recognition," Biomaterials 27: 4165-4168 (Year: 2006).*
Smith et al., "Modified Tobacco mosaic virus particles as scaffolds for display of protein antigens for vaccine applications," Virology 348: 475-488 (2006) (Year: 2006).*
Frolova et al., "Trastumazab-binding peptide display by Tobacco Mosaic Virus," Virology 307: 7-13 (Year: 2010).*
Lee et al., "Mutant Plant Viruses with Cell Binding Motifs Provide Differential Adhesion Strengths and Morphologies", Biomacromolecules 2012, 13, 422-431.
Pokorski et al., "The Art of Engineering Viral Nanoparticles", Molecular Pharmaceuticals, vol. 8, No. 1, 29-43.
Chung et al., "Fabrication of engineered M13 bacteriophages into liquid crystalline films and fibers for directional growth and encapsulation of fibroblasts", Soft Matter, 2010, 6, 4454-4459.
Zhu et al., "Controlled growth and differentiation of MSCs on grooved films assembled from monodisperse biological nanofibers with genetically tunable surface chemistries", Biomaterials 32, 2011, 4744-4752.
Wang et al., "Icosahedral Virus Particles as Addressable Nanoscale Building Blocks", Angew. Chem. Int. Ed., 2002, 41, No. 3, 459-462.
Destito et al., "Biomedical nanotechnology using virus-based nanoparticles", Curr. Opin. Microbiol. Immunol. 2009, 327, 95-122.
Terashima et al., "Human ferritin cages for imaging vascular macrophages", Biomaterials 32, 2011, 1430-1437.
Lee et al., "Fabricating Genetically Engineered High-Power Lithium-Ion Batteries Using Multiple Virus Genes", Science 324, 2009, 1051-1055.
Jennings et al., "The coming of age of virus-like particle vaccines", Biol. Chem., vol. 389, May 2008, 521-536.
Raja et al., "Icosahedral Virus Particles as Polyvalent Carbohydrate Display Platforms", ChemBioChem 2003, 4, 1348-1351.
Miermont et al., "Cowpea Mosaic Virus Capsid: A Promising Carrier for the Development of Carbohydrate Based Antitumor Vaccines", Chem. Eur. J. 2008, 14, 4939-4947.
Kaltgrad et al., "Anti-carbohydrate Antibodies Elicited by Polyvalent Display on a Viral Scaffold", ChemBioChem 2007, 8, 1455-1462.
Mammen et al., "Polyvalent Interactions in Biological Systems: Implications for Design and Use of Multivalent Ligands and Inhibitors", Angew. Chem. Int. Ed. 1998, 37, 2754-2794.
Nemerow et al., "Insights into adenovirus host cell interactions from structural studies", Virology 384, 2009, 380-388.
DiCara et al., "Foot-and-Mouth Disease Virus Forms a Highly Stable, EDTA-Resistant Complex with Its Principal Receptor, Integrin αvβ6 : Implications for Infectiousness", Journal of Virology, vol. 82, No. 3, Feb. 2008, 1537-1546.
Kiessling et al., "Synthetic Multivalent Ligands as Probes of Signal Transduction", Angew. Chem. Int. Ed. 2006, 45, 2348-2368.
Petrie et al., "Multivalent Integrin-Specific Ligands Enhance Tissue Healing and Biomaterial Integration", Sci. Transl. Med, vol. 2, Issue 45, Aug. 18, 2010, 1-7.
Hynes et al., "The Extracellular Matrix: Not Just Pretty Fibrils", Science 2009, 326, 1216-1219.
Danen et al., "Fibronectin, Integrins, and Growth Control", Journal of Cellular Physiology 189, 2001, 1-13.
Kaur et al., "The promotion of osteoblastic differentiation of rat bone marrow stromal cells by a polyvalent plant mosaic virus", Biomaterials 29, 2008,4074-4081.
Kaur et al., "The synergistic effects of multivalent ligand display and nanotopography on osteogenic differentiation of rat bone marrow stem cells", Biomaterials 31, 2010, 5813-5824.
Kaur et al., "Regulation of osteogenic differentiation of rat bone marrow stromal cells on 2D nanorod substrates", Biomaterials 31, 2010, 1732-1741.
Ng et al., "PDGF, TGF-β, and FGF signaling is important for differentiation and growth of mesenchymal stem cells (MSCs); transcriptional profiling can identify markers and signaling pathways important in differentiation of MSCs into adipogenic, chondrogenic, and osteogenic lineages", Blood, vol. 112, No. 2, Jul. 15, 2008, 295-307.
Solmesky et al., "Serum Free Cultured Bone Marrow Mesenchymal Stem Cells as a Platform to Characterize the Effects of Specific Molecules", PLoS One, vol. 5, Issue 9, 1-11.
Nakaoka et al., "Effects of surface chemistry prepared by self-assembled monolayers on osteoblast behavior", J. Biomed. Mater. Res. A, vol. 94A, Issue 2, Aug. 2010.
Hu et al., "Copper-catalyzed ortho-acylatioon of phenols with aryl aldehydes and its application in one-step preparation of xanthones", Chem. Commun. 48, 2012, 11256-11258.
Lee et al., "Multivalent Ligand Displayed on Plant Virus Induces Rapid Onset of Bone Differentiation", Molecular Pharmaceutics, 9 (7), Jul. 2012, 2121-2125.
Luckanagul et al., "Porous Alginate Hydrogel Functionalized with Virus as Three-Dimensional Scaffolds for Bone Differentiation", Macromolecules 2012, 13, 3949-3958.
Sitasuwan et al., "A plant virus substrate induces early upregulation of BMP2 for rapid bone formation", Integr. Biol, 2012, 4, 651-660.
Schlick, et al., "Dual-Surface Modification of the Tobacco Mosaic Virus", J. Am. Chem. Soc. (2005) 127, 3718-3723.
Detzel et al., "Polyelectrolyte Multilayers in Tissue Engineering," Tissue Engineering, Part B, vol. 17, No. 2, 2011, pp. 101-113.
Santi et al., "Virus like particles production in green plants," Methods. Sep. 30, 2006, 40(1), pp. 66-76.
Brill et al., "Recombinant tobacco mosaic virus movement protein is an RNA-binding, a-helical membrane protein," PNAS vol. 97, No. 13: 7112-7117 (2000).
Aldaoud et al. , "Rapid, Random Evolution of the Genetic Structure of Replicating Tobacco Mosaic Virus Populations," Intervirology 30: 227-233 (1989).
Duffy et al. "Rates of evolutionary change in viruses: patterns and determinants," Nature Reviews Genetics, vol. 9: 267-276 (2008).
Yoon et al., "High-temperature-mediated spontaneous mutations in the coat protein of cucumber mosaic virus in Nicotiana tabacum," Arch Virol156: 2173-2180 (2011).
Lindbeck et al., "Coat Protein-Related Polypeptides from in Vitro Tobacco Mosaic Virus Coat Protein Mutants Do Not Accumulate in the Chloroplasts of Directly Inoculated Leaves," Molecular Plant Microbe Interactions, vol. 4, No. 1: 89-94 (1991).
Wang et al., "Molecular Mechanism of Plant Growth Promotion and induced Systemic Resistance to Tobacco Mosaic Virus by Bacillus spp.," J. Microbial. Biotechnol. 19(10): 1250-1258 (2009).
Chaudhary et al., "Interactions of Bacillus spp. And plants—special reference to induced systemic resistance (ISR)," Microbiological Research 164: 493-513 (2009).
Creager et al., "Tobacco Mosaic Virus: Pioneering Research for a Century," Plant Cell11: 301-308 (1999).
Liu et al., "Expression of human acidic fibroblast growth factor in Nicotiana benthamiana with a potato-virus-X-based binary vector," Biotechnol. Appl. Biochem 48: 143-147 (2007).

* cited by examiner

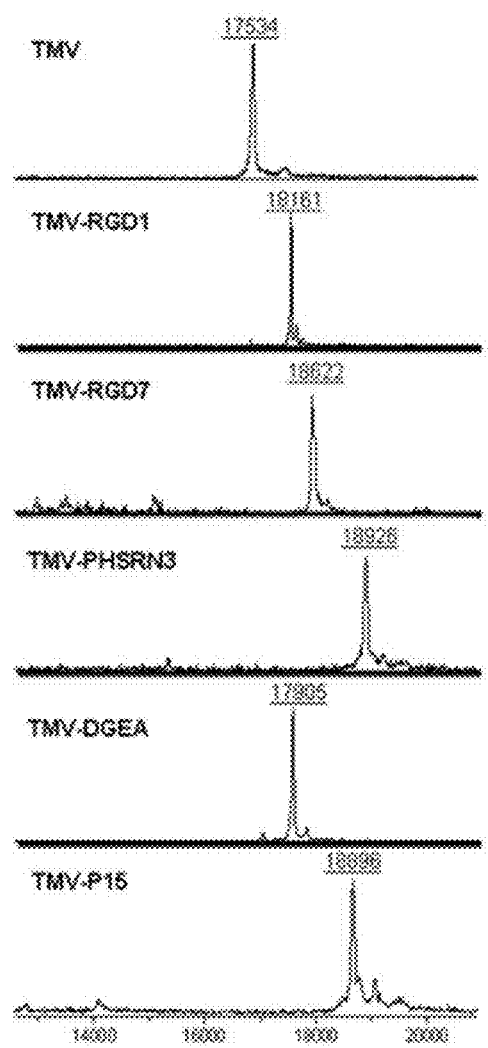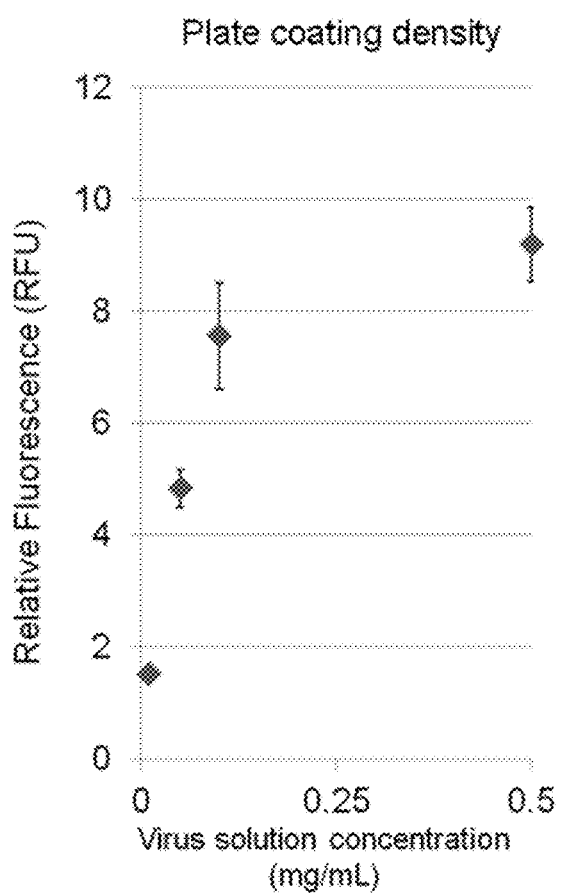
*Fig. 2A*  *Fig. 2B*

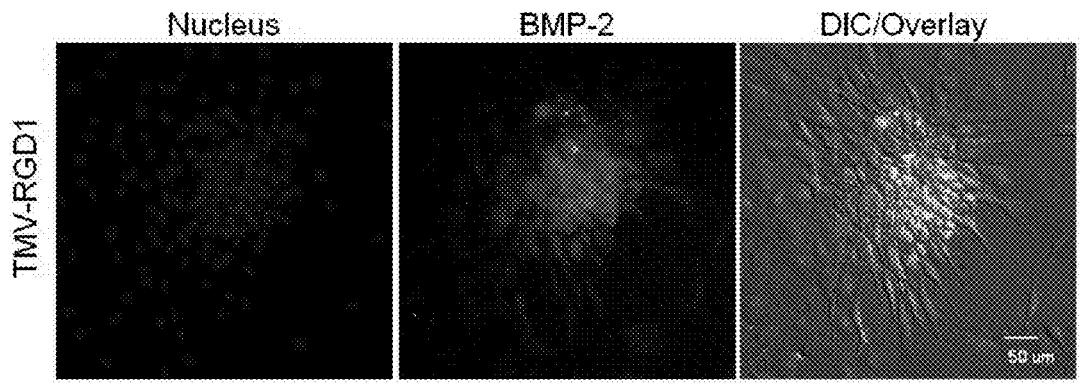
Fig. 18A
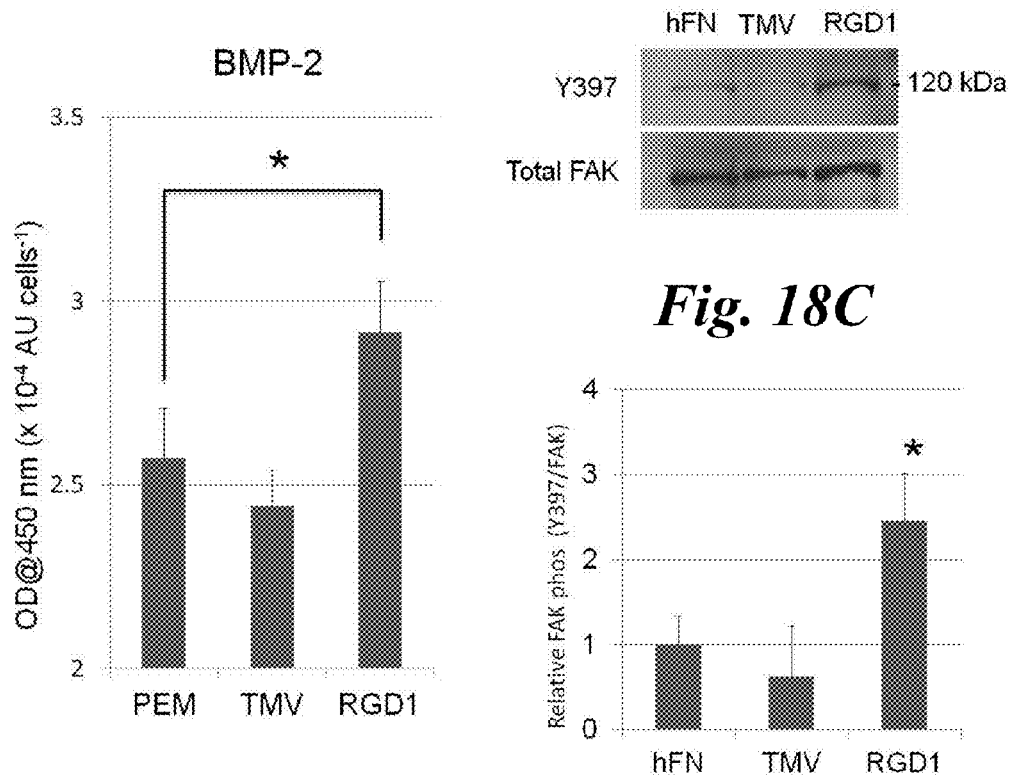
Fig. 18B
Fig. 18C
Fig. 18D

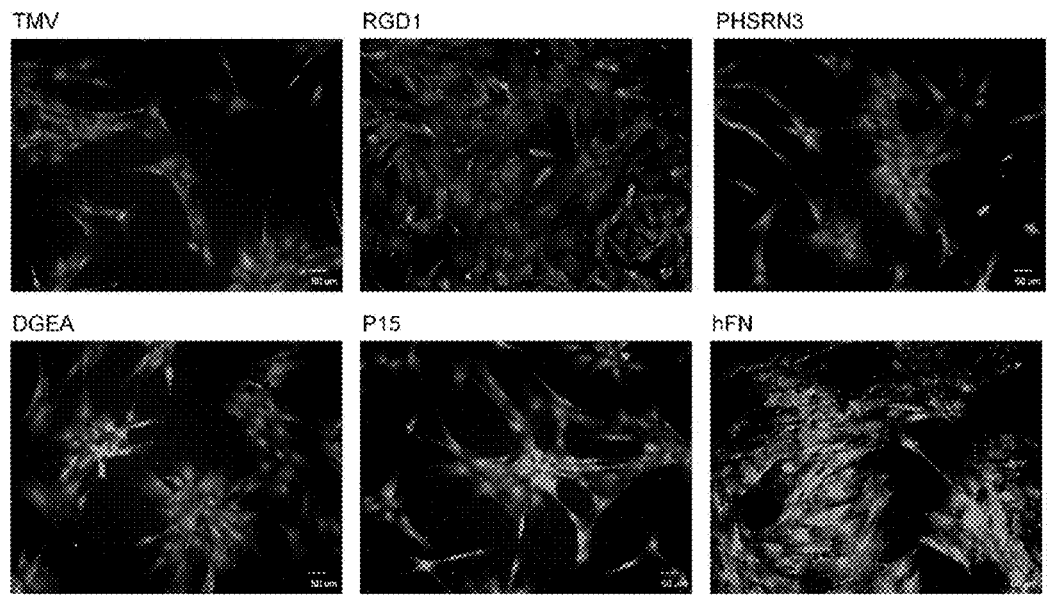
*Fig. 22A*
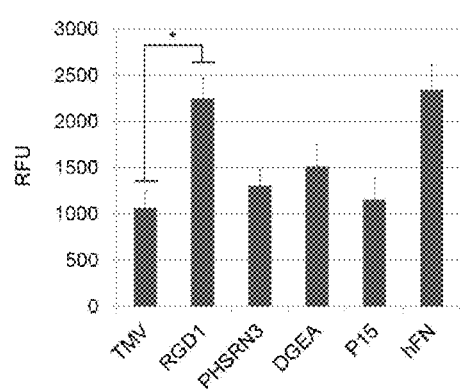 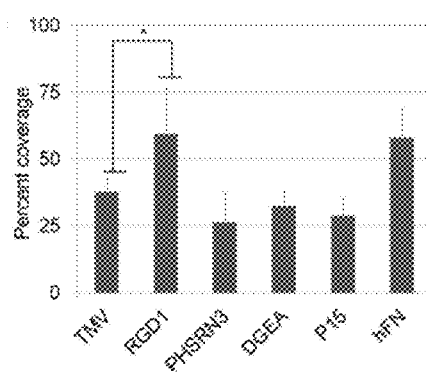
*Fig. 22B*  *Fig. 22C*

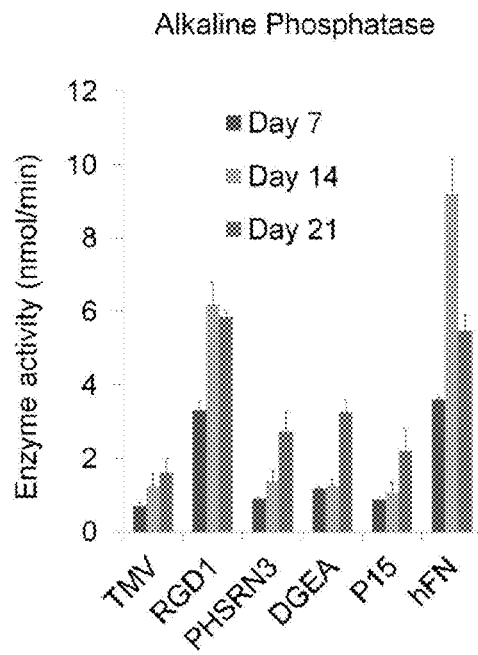
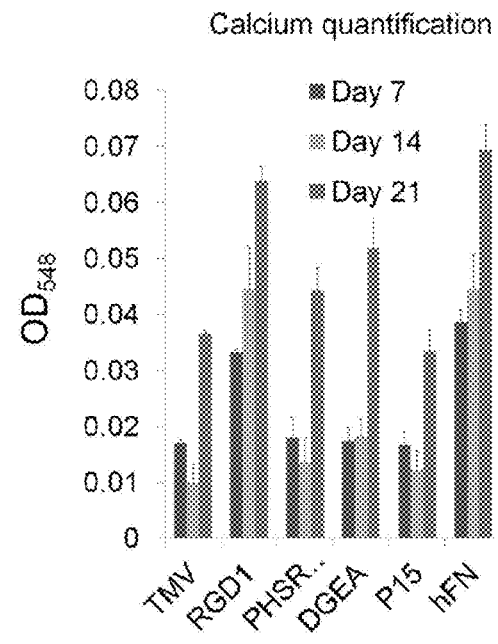
*Fig. 23A*  *Fig. 23B*
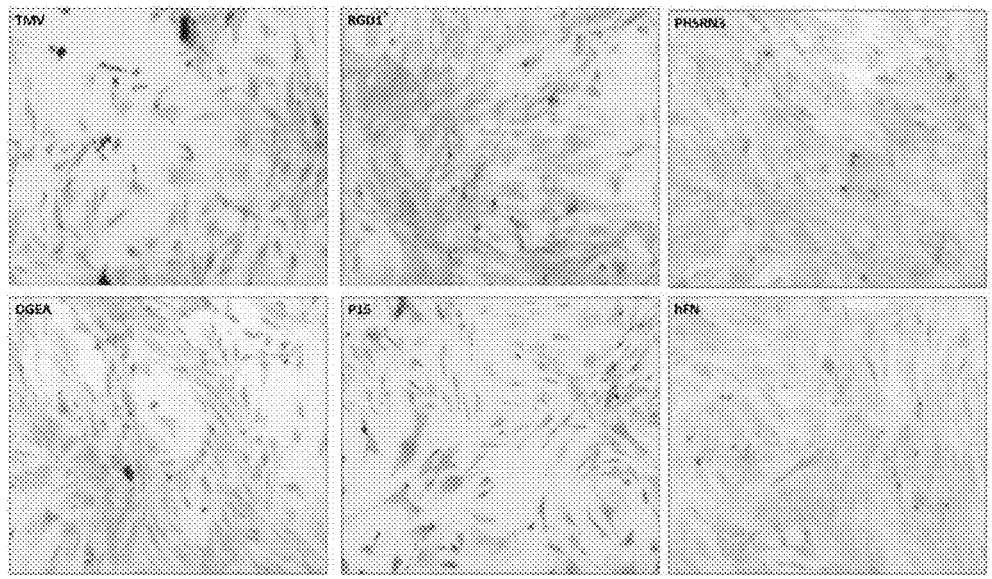
*Fig. 23C*

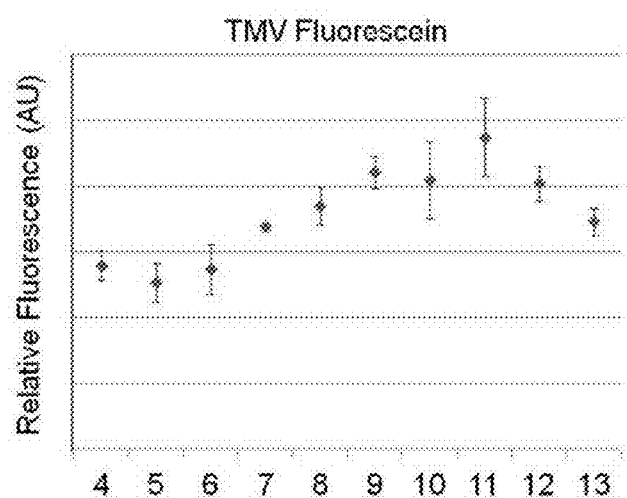
*Fig. 24C*
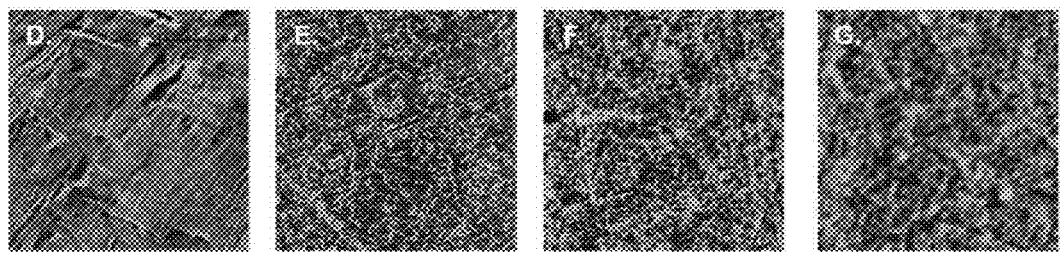
*Fig. 24D-G*

INCORPORATION OF PLANT VIRUS PARTICLES AND POLYMERS AS 2D AND 3D SCAFFOLDS TO MANIPULATE CELLULAR BEHAVIORS

CROSS REFERENCE TO RELATED APPLICATION

The present application is a divisional application claiming priority to U.S. patent application Ser. No. 14/062,059 having a filing date of Oct. 24, 2013, which claims priority to U.S. Provisional Patent Application Ser. No. 61/795,736 filed on Oct. 24, 2012 of Wang, et al. titled "Incorporation of Plant Virus Particles and polymers as 2D and 3D Scaffolds to Manipulate Cellular Behaviors," the disclosures of which are incorporated by reference herein.

GOVERNMENT SUPPORT CLAUSE

The present invention was developed with funding from the National Science Foundation under award CHE-0748690 awarded by the National Science Foundation. The government retains certain rights in this invention.

SEQUENCE LISTING

The instant application contains a Sequence Listing which has been submitted electronically in ASCII format and is hereby incorporated by reference in its entirety. Said ASCII copy, created on Jun. 13, 2014, is named USC-379_SL.txt and is 13,102 bytes in size.

BACKGROUND

Plant viruses and other virus-like particles are utilized in expanded roles as multi-facet nanosized building blocks for directing cell growth and differentiation. Plant viruses are isolated in high purity with batch to batch consistencies in time-honored fashion at low costs. The surface properties of the virus are adjusted through chemical or genetic modifications to incorporate new biologically relevant functional groups. Furthermore, the symmetrical arrangement of the viral proteins make the viral particles attractive scaffolds for displaying identical copies of the functional groups for applications in stem cell cultures, electronics, catalysis, drug/gene delivery, imaging, and immunotherapy.

An argument for using viruses as a biomaterial lies on the premise that structurally ordered functional groups recruit different cellular responses compared to unordered ligands. For example, influenza virus attaches to erythrocytes through multiple binding between hemagglutinin and sialic acid, and some animal viruses display integrin binding sites in a pentameric motif to promote cell internalization. The adhesion force associated with the clusters of integrin binding motifs can be 7-fold stronger over non-clustered ligand-receptor interactions. In cell signaling, the integrin receptors, which are targets for the RGD peptide, form dynamic clusters which are crucial in cell adhesion, motility, as well as echano-transduction, which can all invariably affect stem cell differentiation.

TMV is one of the simplest viruses known. Each viral particle consists of 2130 identical protein subunits arranged in a helical motif around a single stand of RNA to produce a hollow protein tube. The internal and external surfaces of the protein consist of repeated patterns of charged amino acid residues, such as glutamate, aspartate, arginine, and lysine. The rod like TMV is 300 nm in length and 18 nm in diameter. The chemistry of TMV has been studied extensively, and it has been previously demonstrated that coating surfaces with TMV and another plant virus, Turnip yellow mosaic virus (TYMV), enhanced mesenchymal stem cell differentiation towards bone-like phenotype.

Studies have indicated that the coat protein of Tobacco mosaic virus (TMV) can tolerate up to 25 amino acid insertions near its carboxy terminus. By inserting cell-binding sequences to the virus coat protein, specific bio-functionalities can be engineered for use in tissue engineering. The advantages of using TMV or other plant virus particles are multi-fold. First, the structural features and the size range of the virus could be envisioned as highly stabilized, macromolecular extracellular matrix mimetic. The natural extracellular matrix (ECM) proteins play important roles in guiding cell adhesion, migration, proliferation and stem cell differentiation. However these ECM proteins difficult to obtain high yields in cost-effective manner, but the virus-based ECM mimics are routinely purified in high purity (>99%) in time-honored manner. Second, previous studies with plant virus coated substrates demonstrated that the coating of surfaces with native and phosphate-modified virus particles accelerated stem cell differentiation towards bone-like tissues from 21 days of culture to 14 days. The accelerated differentiation process was marked by increased expression levels of key osteogenic markers and an important growth factor known as bone morphogenetic protein-2 (BMP-2). Although the role of TMV coated substrates and BMP-2 has not been fully elucidated, these early studies indicate that the virus-mediated differentiation is not simply based on virus-cell interactions but multiple interactions between the osteoinduction factors (dexamethasone, beta-glycerophosphate and ascorbic acid), serum/cytokine soluble factors, and surface topography.

SUMMARY

Objects and advantages of the invention will be set forth in part in the following description, or may be obvious from the description, or may be learned through practice of the invention.

Methods are generally disclosed for attaching a cell binding motif to a carboxy end of a coat protein of a Tobacco Mosaic Virus particle to form a modified-TMV particle; and attaching a cell to the cell binding motif of the modified-TMV particle.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, which includes reference to the accompanying figures.

FIG. 1A shows a computer reconstructed image of the structure of TMV from a top-down view.

FIG. 1B shows a computer reconstructed image of the structure of TMV from a side cut-away view of the single disc of TMV.

FIG. 1C shows a computer reconstructed image of a single coat protein of TMV with highly rigid region and highly flexible regions. The inside pore along the proximal is slightly flexible with the alpha helices in the mid-section being highly rigid with the carboxy end of the coat protein being highly flexible. This region has been reported to tolerate up to 20-25 amino acid insertions. Images were rendered using PyMol with coordinates 2TMV.pdb1 from Protein Data Bank.

FIG. 2A shows a mass spectrometric analysis of the plant virus mutants direct from plant sap. The high level of coat protein expression in plants permitted the direct detection of the coat protein from crude plant sap by MALDI-TOF MS.

FIG. 2B shows a plot of the RFU vs/concentration taken by modifying TMV particles with fluorescein to the interior surface and then coating on high binding plates at various concentrations (0.01, 0.05, 0.1, and 0.5 mg/mL). At 0.1 mg/mL, the coating density reached a maximum. All coating experiments were done with n=8 with three separate experiments. Significant values were based p values less than 0.05 with two-tailed equal variance Student t-test.

Figure 3:
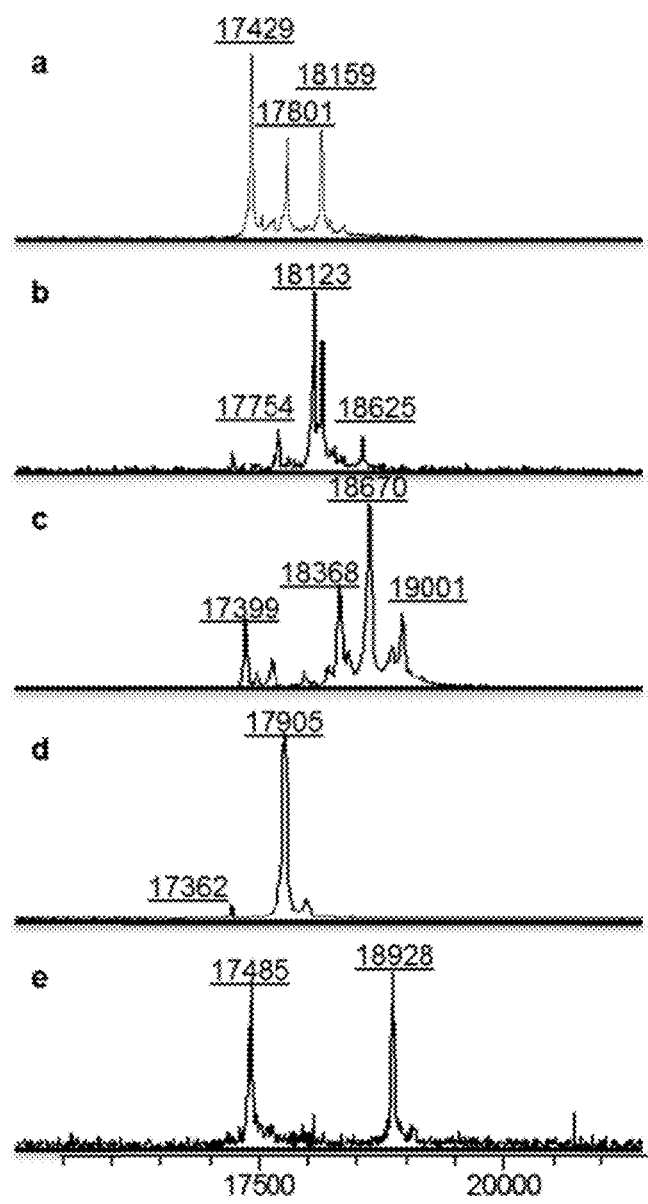

FIG. 3 shows the mass spectrometric analysis of several degraded plant virus mutants: (a) TMV-RGD1; (b) TMV-RGD7; (c) TMV-PHSRN3; (d) TMV-DGEA; (e) TMV-P15.

Figure 4:
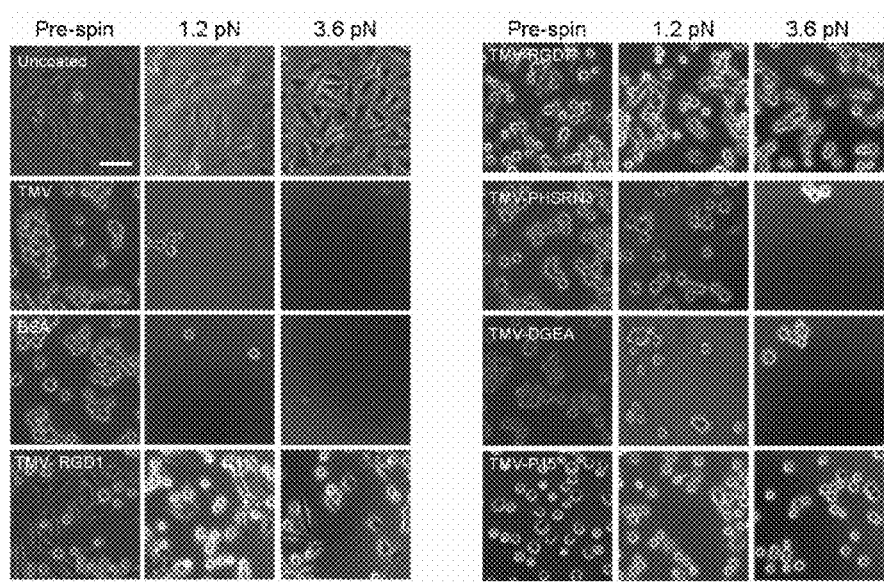

FIG. 4 shows the phase contrast light microscopy images of BHK cells prior and post centrifugation. The uncoated substrate provided the highest level of attachment for the BHK cells in serum-free conditions, whereas the wild type TMV coating blocked cell attachment to the plate. 1% BSA coating was used to block all non-specific interactions between the cells and substrate. The cells on TMV-RGD1 coated substrate showed filopodial extensions, as expected with the presence of RGD tripeptide sequence, as well as for the RGD7 coated substrate. Both TMV-RGD1 and TMV-RGD7 substrates seem to support similar attachment levels with similar long cell body extensions. The fibronectin synergy mimetic, TMV-PHSRN3, provided weaker attachment with most of the cells detaching at 30 g spin which is approximately 3.6 pN per cell. Similar detachment forces were observed for on collagen mimetic, TMV-DGEA coated substrates. Although the cells on the other collagen mimetic, TMV-P15 coated substrates did not exhibit the long filopodial extensions as on RGD1 or RGD7 substrates, higher detachment forces were measured for the cells on P15. Scale bar is 50 microns.

Figure 5A:
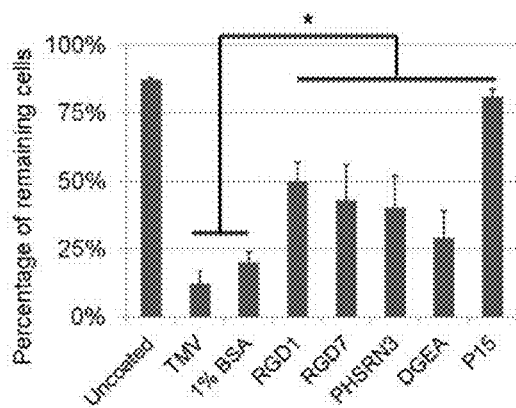

FIG. 5A shows a centrifugal adhesion assay to measure detachment forces of several BHK cells. An inverted spin at 10 g (~1.2 pN/cell) for 5 minutes resulted in cell detachment from TMV and BSA coated substrates, whereas approximately 50% of the cells were detached for TMV-RGD1, RGD7, and PHSRN3 coated substrates. Only a fourth of the cells were remaining for the TMV-DGEA coated substrates. TMV-P15 coated substrate, despite the lack of filopodial extensions, had the highest percentage of cells remaining on the substrate.

Figure 5B:
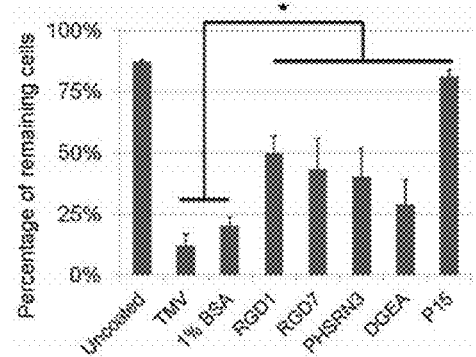

FIG. 5B shows that the centrifugal adhesion assay using a higher centrifugal force of 30 g (~3.6 pN/cell) detached the cells from PHSRN3 and DGEA (SEQ ID NO: 4) coated substrates, whereas slight decrease in the number of cells was measured on RGD1, RGD7 and P15. *p<0.05 (n=6, unpaired Student t-test) when compared to TMV coated substrates from three separate experiments. Error bars denote standard error of mean.

Figure 5C:
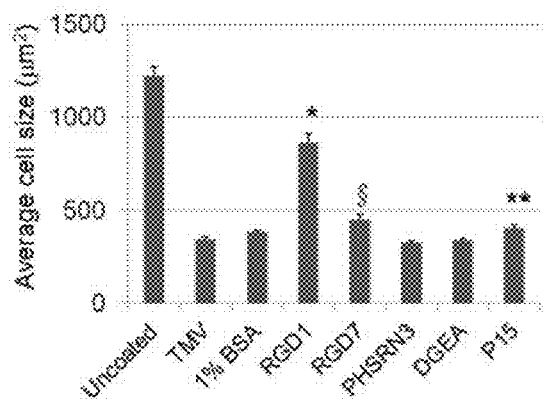

FIG. 5C illustrates the average cell body sizes prior to subjecting the cells to inverted centrifugation. There appears to be no clear relation between cell body sizes to adhesion forces. *p<0.001; § p<0.005; **p<0.01 (n=50, unpaired Student t-test) when compared to cells on TMV coated substrates. Error bars denote standard error of mean.

Figure 5D:
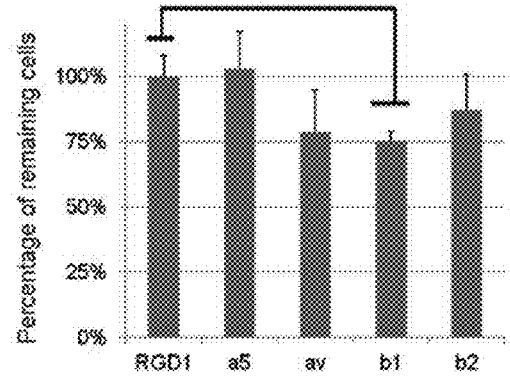

FIG. 5D presents the results of integrin specific monoclonal antibody inhibition studies for RGD1. Based on the results, cell adhesion is only slightly reduced with anti-β1 integrin antibody for cells on TMV-RGD1.

Figure 5E:
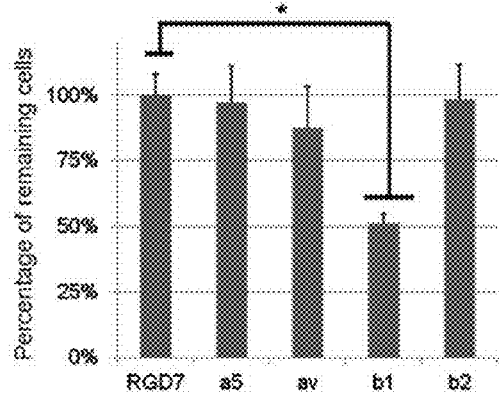

FIG. 5E presents the results of integrin specific monoclonal antibody inhibition studies for RGD7. Based on the results, the cells on TMV-RGD7 show less attachment.

Figure 5F:
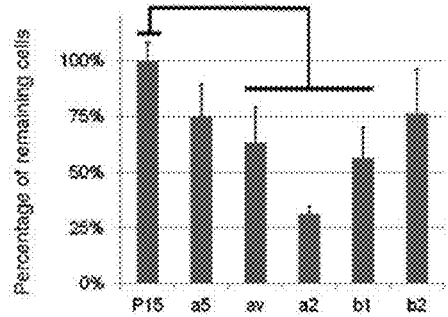

FIG. 5F presents the results of integrin specific monoclonal antibody inhibition studies for P15 coated substrates. Cell attachment on TMV-P15 is dramatically reduced when receptors are inhibited with anti-α2 antibody. *p<0.05 (n=4, paired, two-tailed Student t-test).

Figure 6:
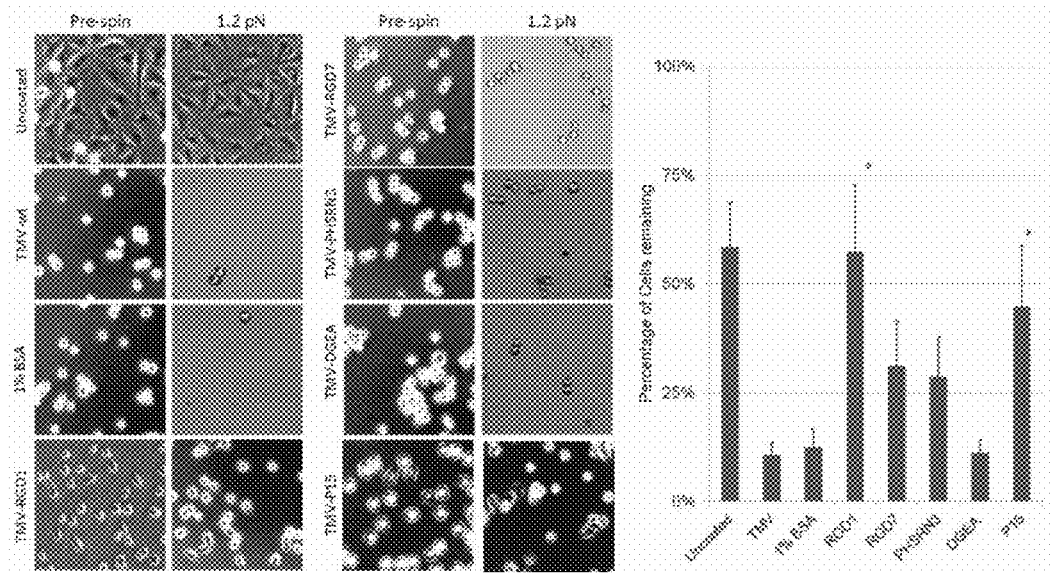

FIG. 6 shows a centrifugal adhesion assay to measure detachment forces for CHO cells. An inverted spin at 10 g (~1.2 pN/cell) for 5 minutes resulted in cell detachment from majority of the substrates except for TMV-RGD1 and TMV-P15 coated substrates *p<0.05 (n=6, unpaired Student t-test) when compared to TMV coated substrates from three separate experiments performed with six replicates. Error bars denote standard error of mean.

Figure 7:
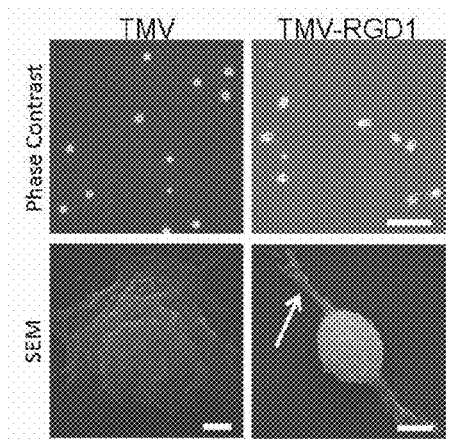

FIG. 7 shows the cell Morphology on TMV (left column) and TMV-RGD1 (right column). The cells cultured on TMV were round and poorly spread, but the cells on TMV-RGD1 possessed long and thin filopodial extensions. The white arrow points to the extended filopodia on TMV-RGD1. Such morphological features are not commonly found on other surface coatings. Scale bar for phase contrast images (top row) is 100 microns, and scale bars for SEM images (bottom row) are 2 microns and 10 microns for TMV and TMV-RGD1, respectively.

Figure 8A:
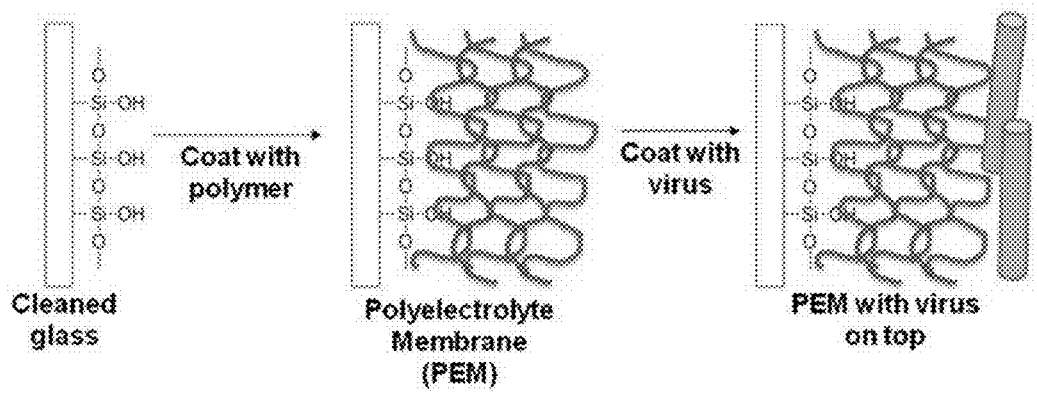

FIG. 8A shows results of plant viruses as substrates for stem cell cultures. Shown is a schematic illustration of PEM preparation by cleaning the glass substrate to generate hydroxyl groups on the surface followed by coating with PAH, then PSS. The last layer is the virus coating.

Figure 8B:
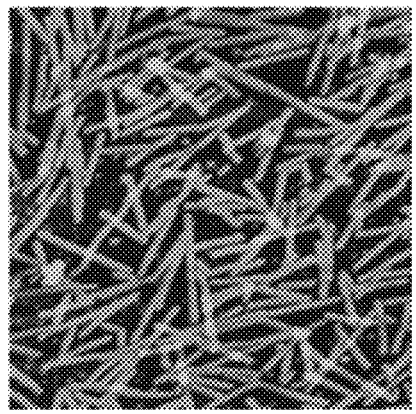

FIG. 8B shows AFM height image (2.5×2.5 microns) of TMV on the top layer and indicates the viral particles are mostly intact and laid flat on the surface.

Figure 8C:
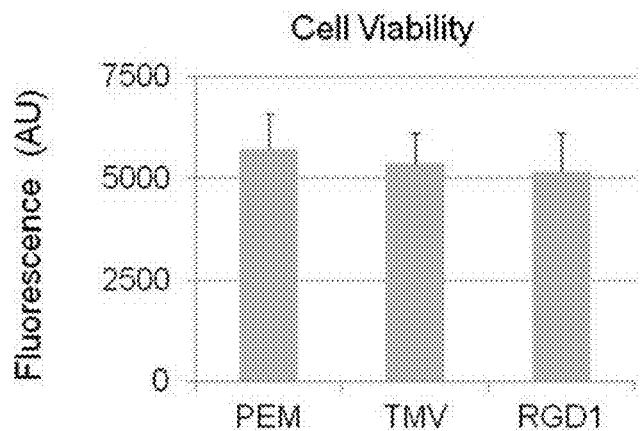

FIG. 8C shows that the average cell metabolic rates based on CellTiter Blue (Promega) indicate similar viability across all substrates, indicating the plant viruses are not toxic to the cells.

Figure 9:
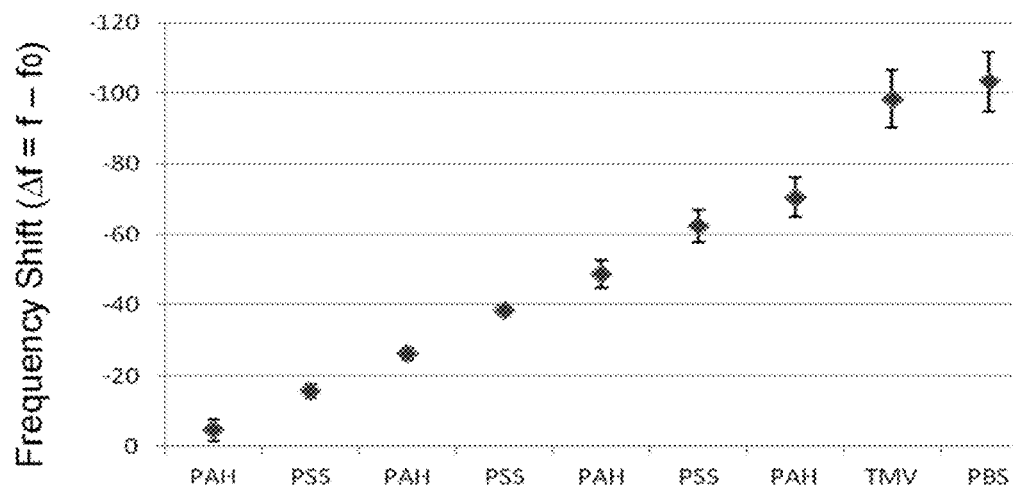

FIG. 9 shows the QCM measurements of PAH/PSS polyelectrolyte membrane with TMV. Each layer of coating decreases the frequency in a linear fashion. TMV coating was followed by incubation in 1x PBS solution for one hour. A slight shift in frequency was observed, likely due to the osmolarity difference between TMV (100 mM K Phos pH 7.0) versus PBS. Error bars denote standard deviation from the mean (n=9) and 3 separate experiments in triplicates.

Figure 10:
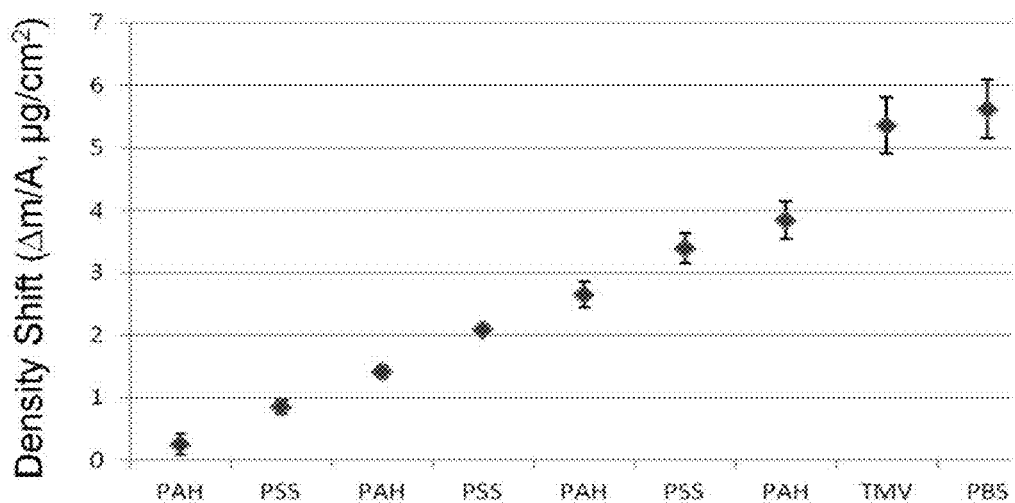

FIG. 10 shows the mass density shift of polyelectrolyte membrane. A linear mass shift is observed until TMV coating, where the total amount of viral particles averaged 1.5±0.3 µg/cm$^2$. Incubation with PBS solution allowed for slight swelling of the PEM, increasing the density shift by 0.3±0.1 µg/cm$^2$. Error bars denote standard deviation from the mean (n=9) from three separate experiments performed in triplicates.

Figure 11:
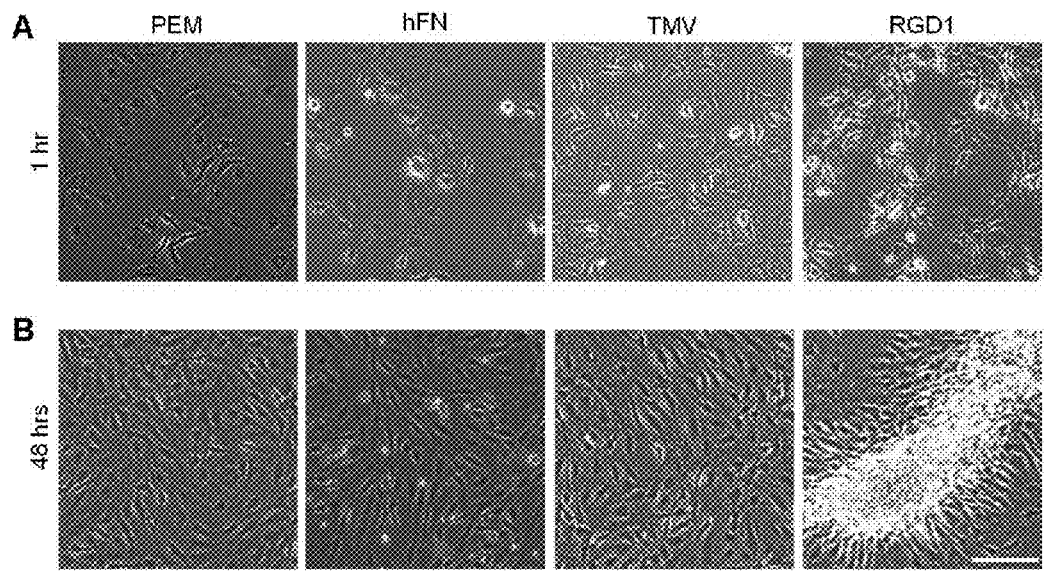

FIG. 11 shows stem cells aggregate after 48 hours of osteoinduction. Phase contrast microscopy images of BMSCs (row A) after one hour of seeding, the cells on PEM, hFN (human fibronectin), TMV and TMV-RGD1 coatings on top of PEM exhibit similar morphologies for all three samples, (row B) but after 2 days in serum-free osteogenic media, only the cells on TMV-RGD1 coating (labeled as RGD1 on figure) aggregate to large nodules. Scale bar is 200 microns.

Figure 12A:
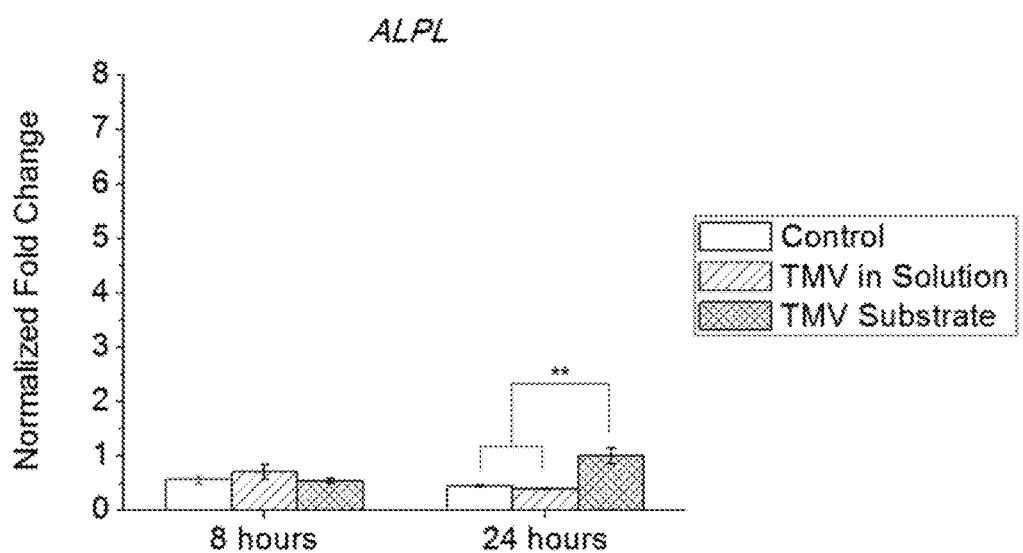

FIG. 12A shows RT-qPCR analysis for osteo-specific gene expression of BMSCs under osteogenic conditions. For each growing condition, the profiles showed two time points: 8 and 24 hours after induction with osteogenic media. Gene expression in the cells seeded on TCP, TCP with TMV in solution and TMV substrate under osteogenic conditions. As shown, ALPL expression was upregulated in cells grown on TMV at 24 hours.

Figure 12B:
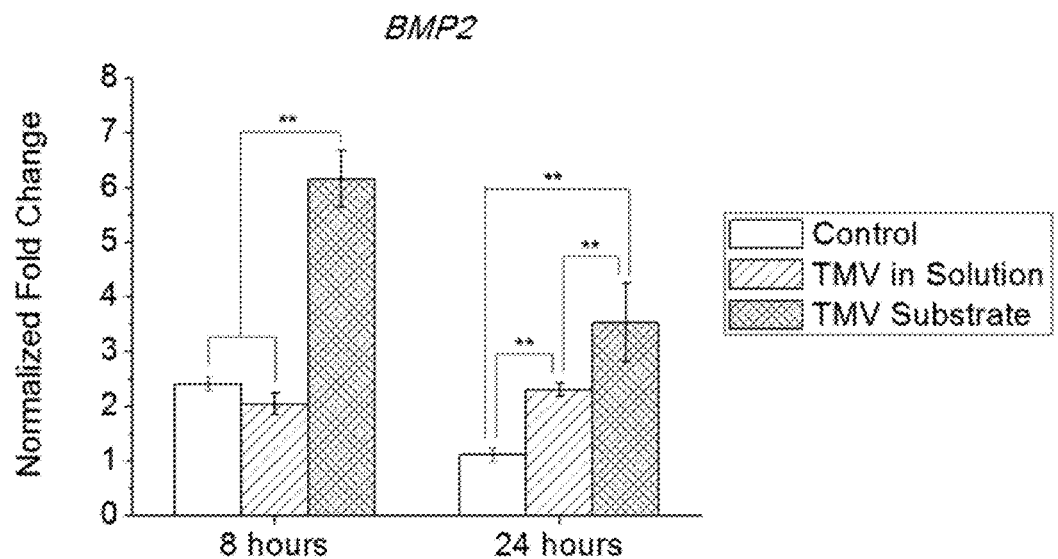

FIG. 12B shows BMP2 expression at both time points was significantly increased in cells grown on TMV substrates.

Figure 12C:
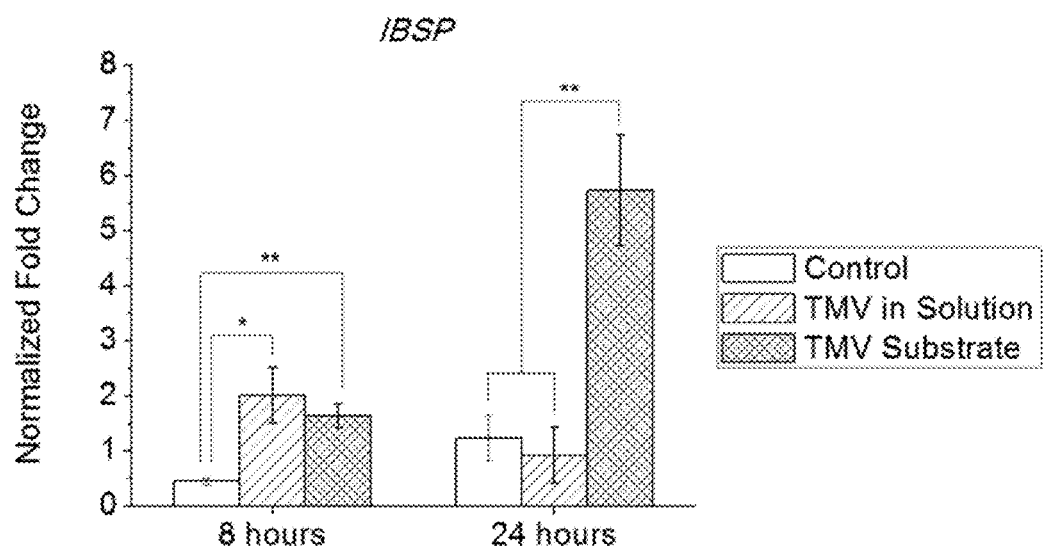

FIG. 12C shows IBSP was highly expressed in cells grown on TMV substrates at both time points. In all graphs, the error bars denote±1 s.d. (**) and (*) represent $p<0.05$ and $p<0.1$, respectively.

Figure 13A:
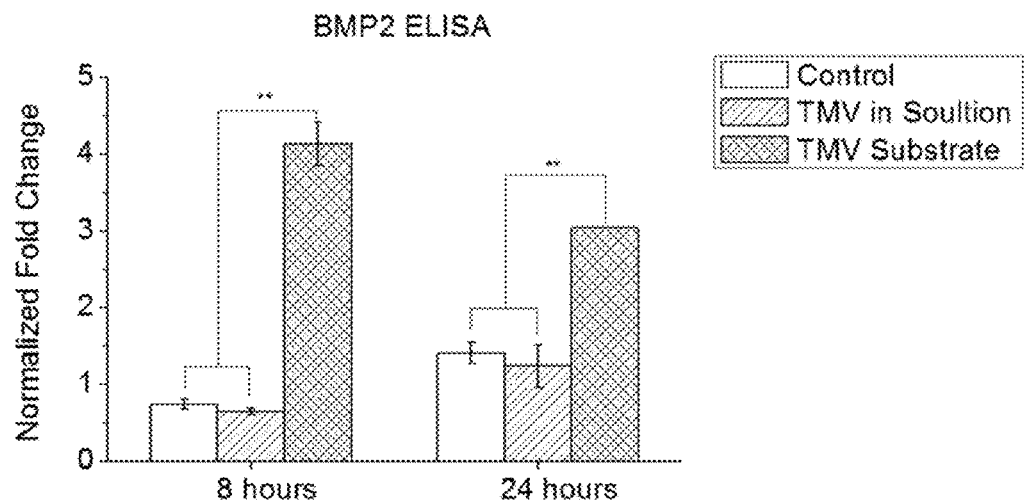

FIG. 13A shows the differential expression and localization of BMP2 analyzed by ELISA and immunohistochemical staining. As shown, the quantification of BMP2 protein expression at 8 and 24 hours was normalized to cell number by ELISA. The values are expressed as fold change compared to cells on TCP before osteoinduction. The error bars denote±1 s.d. *$p<0.01$ based on equal variance two-tailed Student t-test.

Figure 13B:
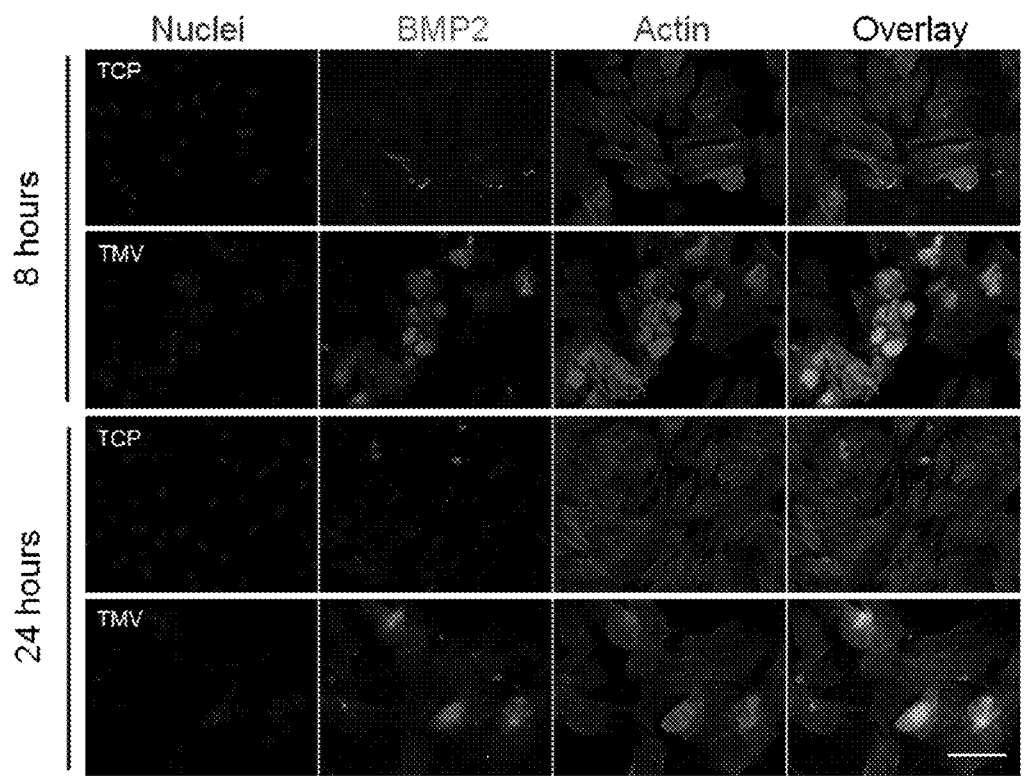

FIG. 13B shows the cells on TCP control or TMV substrate that were collected at 8 and 24 hours after osteogenic induction. At both time points, cells on TMV-coated surface expressed more BMP2 protein and the protein is highly expressed at cell aggregates. Scale bar is 100 μm.

Figure 14A:
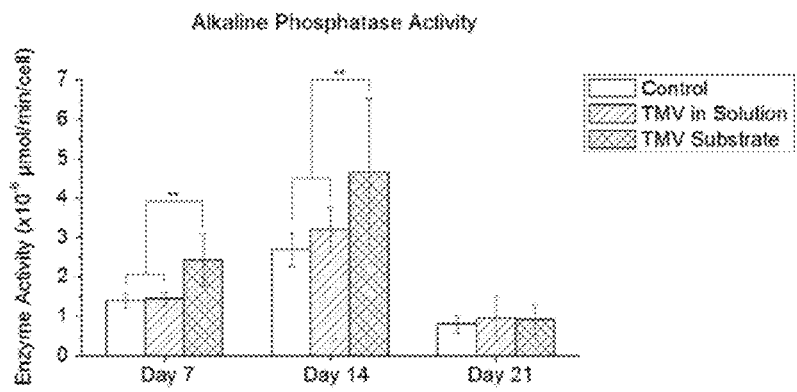

FIG. 14A shows cytochemical analysis of bone differentiation process of BMSCs on TCP, TCP with TMV in media, TMV substrate at 7, 14, and 21 days after osteogenic induction. Shown is alkaline phosphatase activity of cells in three different conditions. Cells on TMV substrate have an increase in enzyme activity at day 7 and 14, whereas the addition of TMV solution does not alter the enzyme activity when compared to control. Alkaline phosphatase activity drops to baseline at day 21 for all conditions.

Figure 14B:
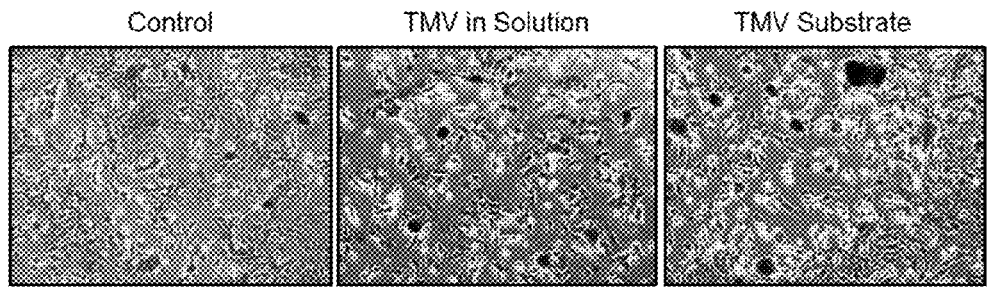

FIG. 14B shows alizarin red staining of each sample at day 14.

Figure 14C:
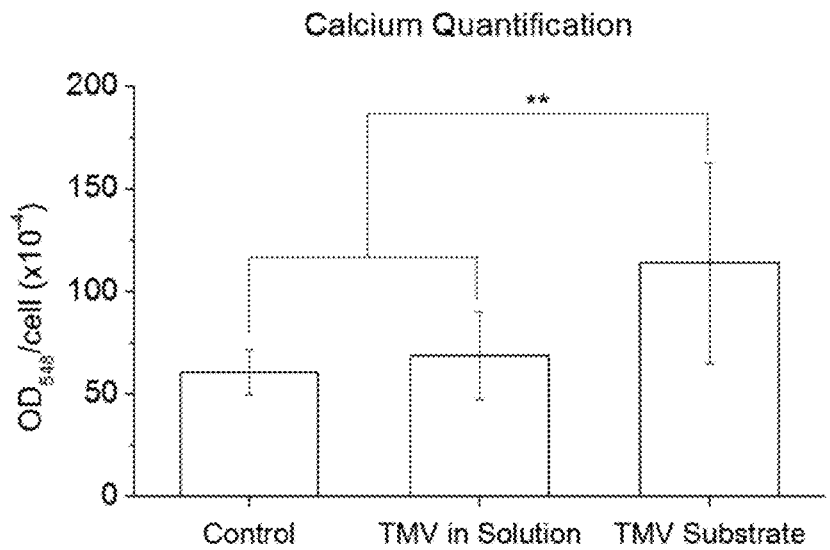

FIG. 14C shows absorbance at 548 nm normalized to cell number to indicate relative amount of calcium deposit at day 14 stained by alizarin red solution. The mineralization of cells on TMV substrate doubles that of TCP and TMV in solution, suggesting an improvement in osteogenesis (** $p<0.05$ based on equal variance two-tailed Student t-test). The error bars denote±s.d.

Figure 15:
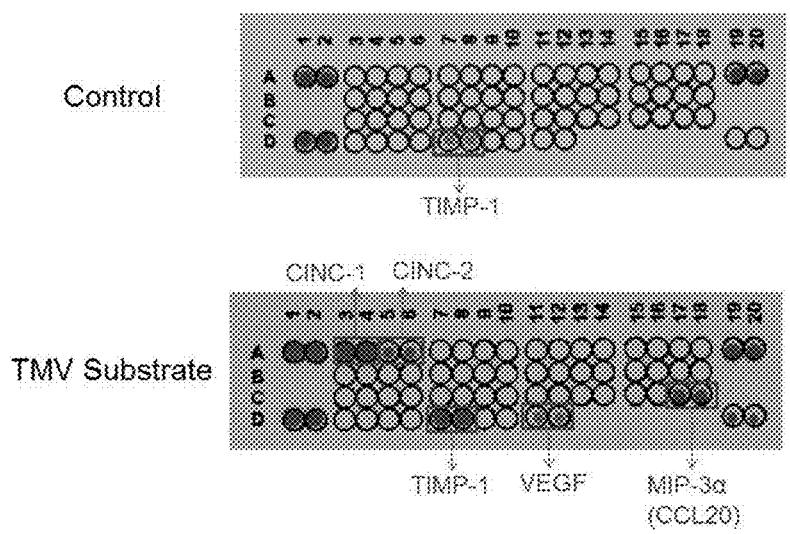

FIG. 15 shows a comparison of cytokine profiles in culture media of BMSCs on TCP control and TMV substrate for 24 hours, prior to osteoinduction. An antibody array containing 29 different cytokines was used to compare protein profiles produced by cells on different substrates. TIMP-1 was detected in both cultures with higher levels from TMV substrate. However, the productions of some cytokines and growth factors were induced only by TMV-coated wafer, including CINC-1, CINC-2, MIP-3a, and VEGF.

Figure 16:
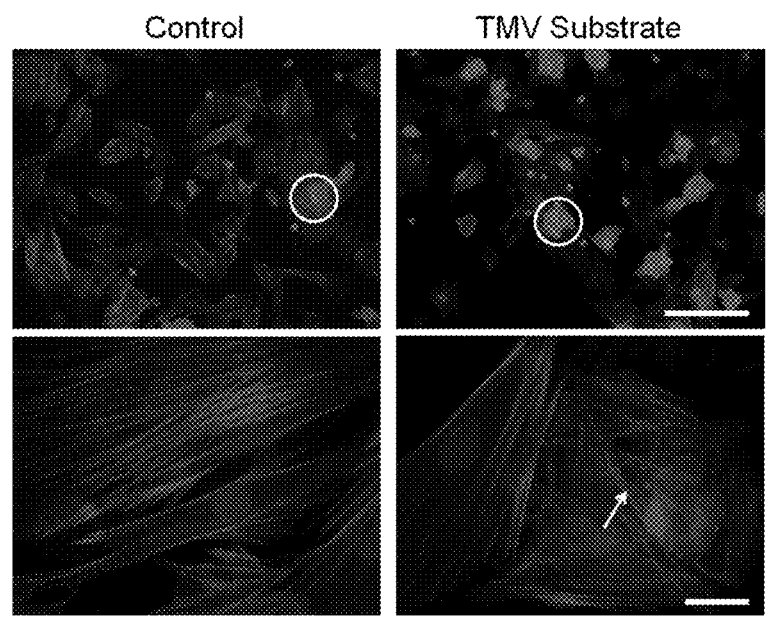

FIG. 16 shows cytoskeleton immunochemical staining showing actin polymerization and organization of cells on TCP control and TMV substrate after 24 hours seeding, prior to osteoinduction, at low- (top row) and high-magnification (bottom row). Similar fibrous cytoskeleton organization was observed where cells spread out in both cell cultures. However, in cell aggregates on TMV substrate the actin intensity was higher (white circles) and well-defined actin filament was absent (white arrow). Scale bars are 200 μm for top row and 25 μm for bottom row.

Figure 17A:
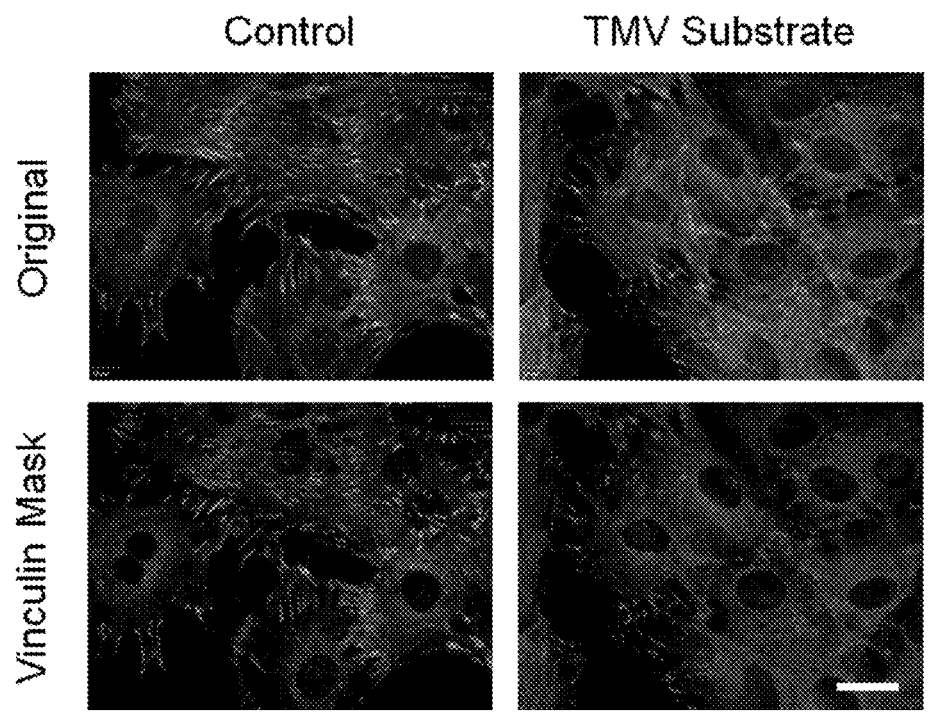

FIG. 17A presents immunochemical staining showing the difference in vinculin size of cells on TCP control or TMV substrate for 24 hours. Shown are immunofluorescence images of cells on different substrates for 24 hours prior to osteoinduction (top panel). The bottom panel illustrates vinculin masking and selection for size analysis. The selected vinculin spots as part of focal adhesion complex are highlighted.

Figure 17B:
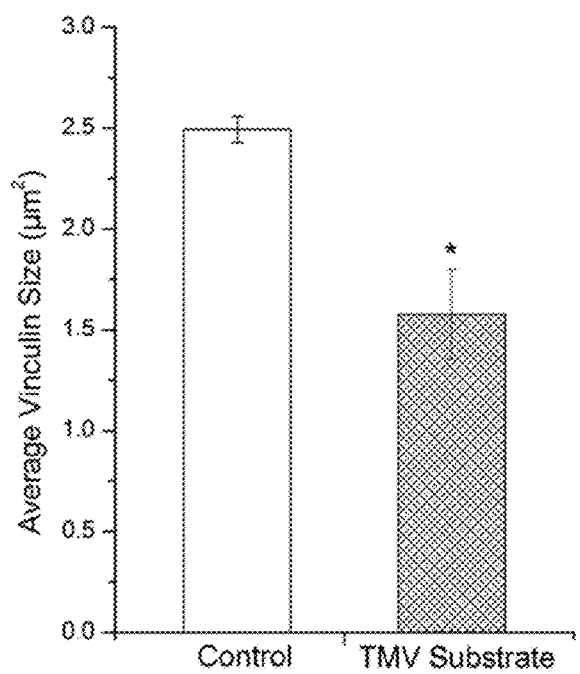

FIG. 17B shows average vinculin size of cells on either TCP or TMV-coated surface. The error bars denote±s.d. and *$p<0.05$ based on equal variance two-tailed Student t-test.

FIG. 18A shows BMP-2 expressions are localized to the nodules, most are found on TMV-RGD1 substrates (annotated as RGD1 on figure). Scale bar is 100 microns for phase contrast and 50 microns for DIC/fluorescence images.

FIG. 18B illustrates results of BMP-2 expression quantified by probing with anti-BMP2 primary followed by anti-mouse goat IgG-HRP with TMB solution. Error bars denote±SEM (n=12). *$p<0.05$ using two-tailed equal variance Student t-test comparing TMV-RGD1 to all substrates.

FIG. 18C presents determination of focal adhesion kinase (FAK) activity by probing with anti-FAK pY397 and anti-total FAK. pY397 FAK intensity was normalized against total FAK and set relative to hFN controls. Error bars denote±s.d. (n=3). *$p<0.05$ using two-tailed equal variance Student t-test.

FIG. 18D shows that the increase in focal adhesion kinase phosphorylation at residue Y397 observed for cells cultured on TMV-RGD-1 coated substrates was two-fold above the levels detected for cells on human fibronectin.

Figure 19A:
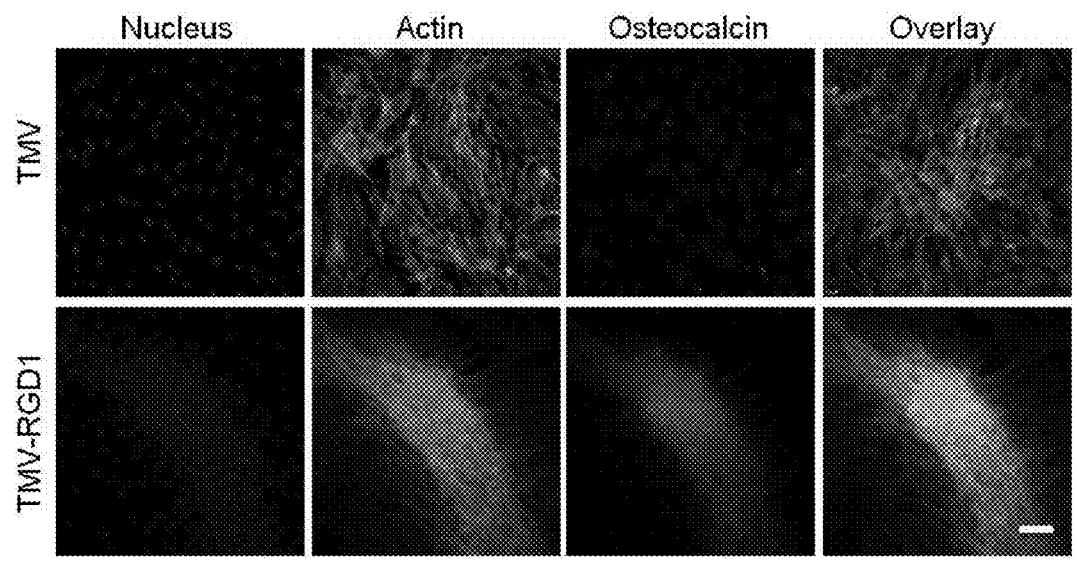

FIG. 19A shows osteocalcin expression after 2 days of induction. A canonical osteogenic marker, osteocalcin, is exclusively found on cell aggregates growing on TMV-RGD1 coated substrates. For cells on TMV, the isolated cells express low levels of osteocalcin which was similar to uncoated PEM. Scale bars are 100 microns for FIG. 19A.

Figure 19B:
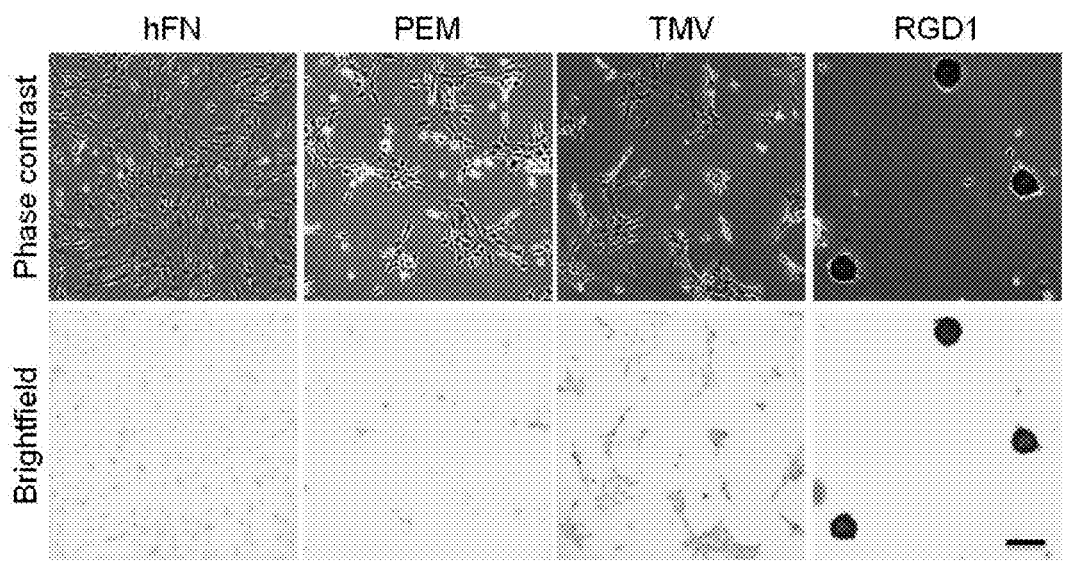

FIG. 19B: BMSCs undergo rapid nodule formation on TMV-RGD1 coated substrates only. Phase contrast and brightfield images of BMSCs cultured in osteogenic media for 2 days then stained with Alizarin Red S (red) for calcium. The cells on virus coated substrates stain positive for calcium deposits faster than on cells on human fibronectin substrates. The largest aggregates are observed for the cells cultured on TMV-RGD1 coated substrates. Scale bars are 200 microns for FIG. 19B.

Figure 20:
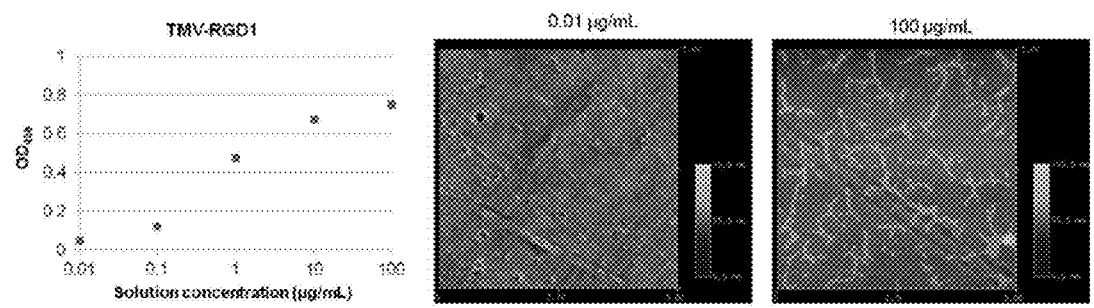

FIG. 20 shows tobacco mosaic virus coating on high binding plates. The coating was monitored by indirect ELISA, where the virus is coated to the substrate, then probed with anti-TMV polyclonal sera from immunized Rabbits (purchased from Sigma), followed by anti-rabbit goat antibody conjugated with HRP. The lower OD (optical density) indicates low density coating, with higher OD indicating more virus on coated on substrates. At concentrations above 100 μg/mL, the signal appears to be saturated. The two images (middle and right panels) are representative atomic force microscopy height images of substrates coated in low virus concentration (0.01 μg/mL) and high virus concentration (100 μg/mL). Despite the near saturated signal from ELISA, the AFM images indicate less than full coverage of the surface with virus particles. Scan area for both images are 5×5 microns.

Figure 21:
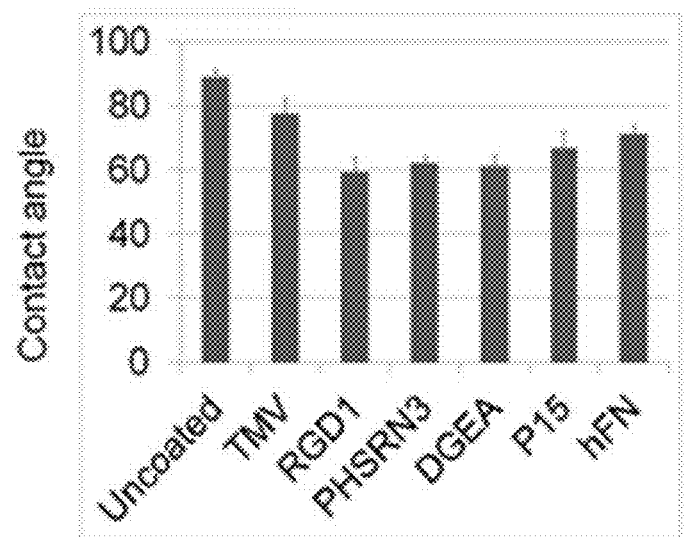

FIG. 21 shows water contact angle measurements of high binding plates coated with Tobacco mosaic virus and mutants. Each well was coated with 100 ul of virus solution at 0.1 mg/mL in pure water. The surfaces were washed 3 times with pure water and cut out from the plate. VCA Optima was used to measure the water contact angle by sessile drop test.

FIG. 22A shows results from rat bone marrow derived mesenchymal stem cells that were seeded on the virus coated high binding plates. The cell attachment and spreading on the various mutants were visualized by staining the live cells with calcein AM within 24 hours of seeding (the live cells indicated by the green fluorescence). Scale bar is 50 microns.

FIG. 22B: Fluorescence intensity (RFU—relative fluorescence unit) is a measurement from the fluorescence plate reader for the different samples. Higher fluorescence intensity correlates to greater spreading of the cells on the substrates.

FIG. 22C: Cell spreading was measured from each microscope image and averaged, then normalized to the total area of each picture frame. This measurement matches the fluorescence measurements from the plate reader.

FIG. 23A shows results of rat bone marrow derived mesenchymal stem cells seeded on the virus coated high binding plates that were differentiated under serum-free osteogenic media. The alkaline phosphatase activity assay indicates progressive differentiation of the cells in serum-free media over 21 days with cells seeded on TMV-RGD1 and human fibronectin (hFN) exhibit high enzymatic activity levels.

FIG. 23B: Calcium measurements also indicate progressive increase in mineralization over the 21 day time frame with RGD1 and hFN substrates having consistently higher calcium levels than the other substrates.

FIG. 23C: Cells stained with Alizarin Red S were imaged with brightfield inverted microscope.

Figure 24A:
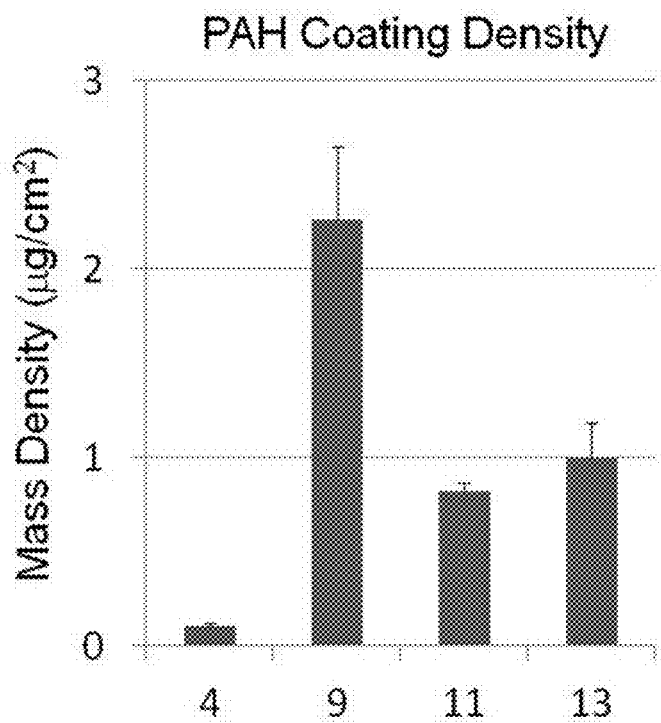

FIG. 24A shows results of surface coating optimization using single layer of polyelectrolytes. The illustrated results of quartz crystal microbalance studies indicate that PAH deposition is highest when surfaces are coated at pH near the pI value of PAH (~9.5).

Figure 24B:
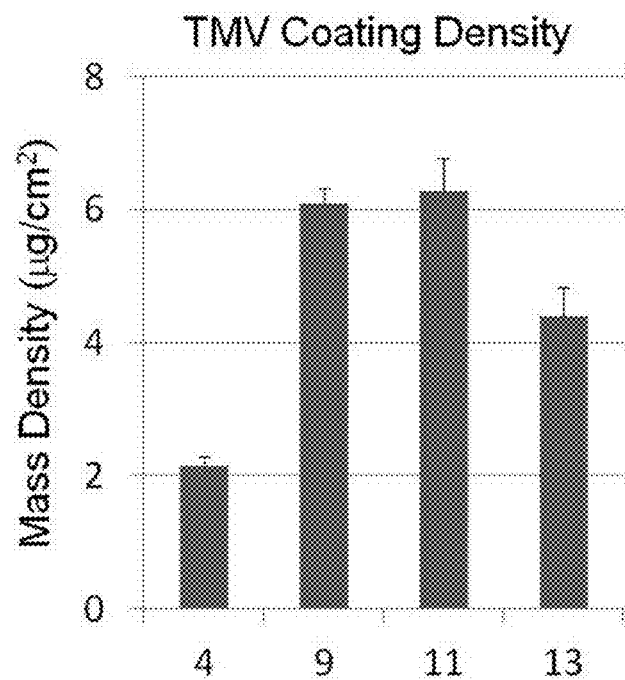

FIG. 24B: Virus deposition reaches maximum density for quartz surfaces coated with PAH solutions prepared at pH 9-11 (virus concentration=1 mg/mL and 100 mM potassium phosphate pH 7 buffer).

FIG. 24C: Fluorescently labeled TMV particles were used to coat tissue culture polystyrene and monitored using a fluorescent plate reader (ex/em=490/520 nm). The results on plasticware coincide with the QCM measurements on quartz wafers.

FIG. 24D: Atomic force microscopy height image of uncoated surface.

FIG. 24E: Atomic force microscopy height image of surface at pH 4.

FIG. 24F: Atomic force microscopy height image of surface at pH 11.

FIG. 24G: Atomic force microscopy height image of surface at pH 13. The scan areas for the AFM height images in FIGS. 24D-24G are all 5 by 5 microns.

Figure 25:
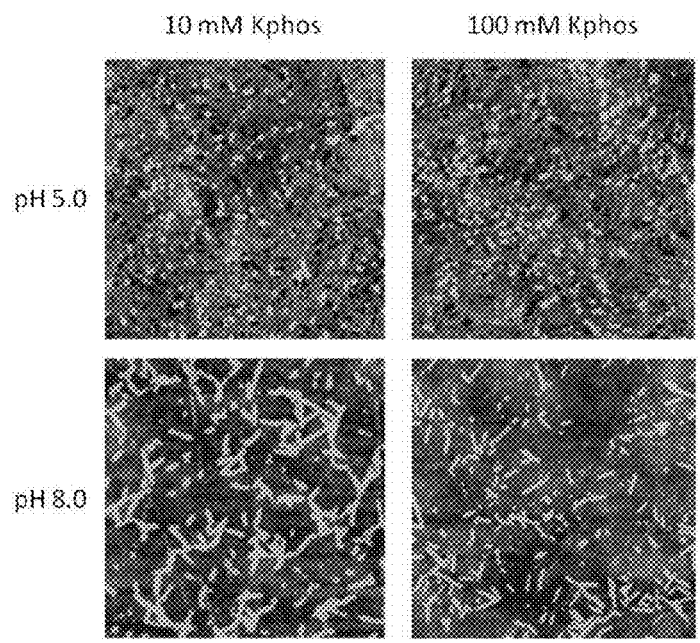

FIG. 25 shows surface coating optimization using single layer of polyelectrolytes. Atomic force microscopy height images of surfaces coated with TMV particles at different pH and buffer strengths. The scan areas for the AFM height images are all 5 by 5 microns.

Figure 26:
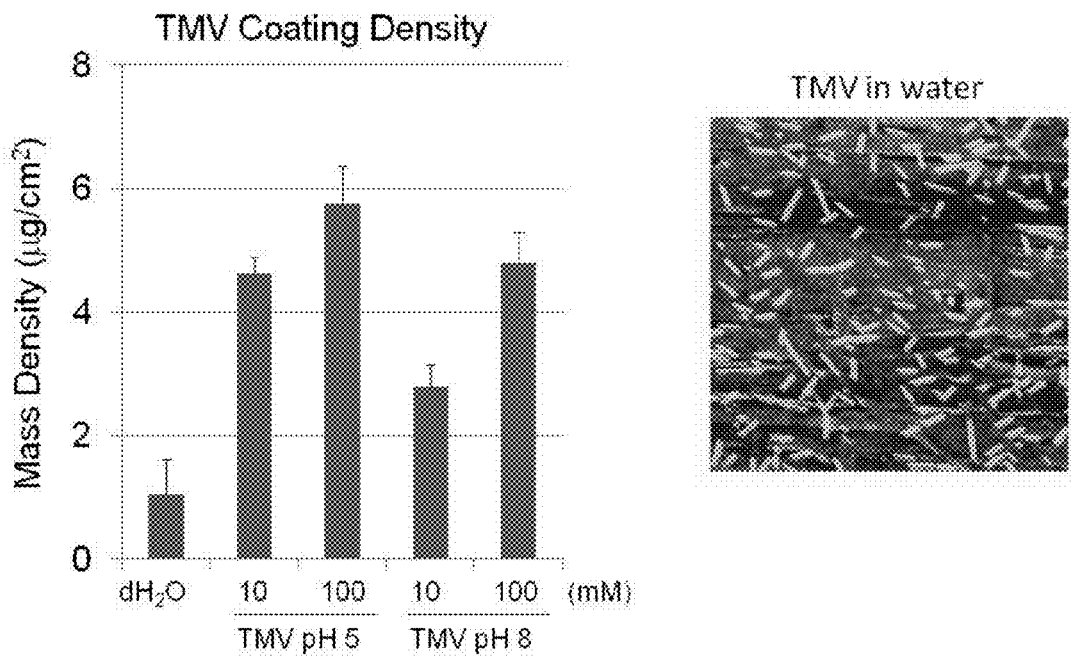

FIG. 26 shows surface coating optimization using single layer of PAH. QCM measurements corroborate the results from the AFM height images, where the pH 5 solutions provide highest depositions of the viral particles on PAH. Increasing the pH to 8 decreases the amount of virus deposited on the surface. Eliminating the salt and using TMV in water further decreased the deposition, as indicated by both AFM and QCM analyses.

Figure 27:
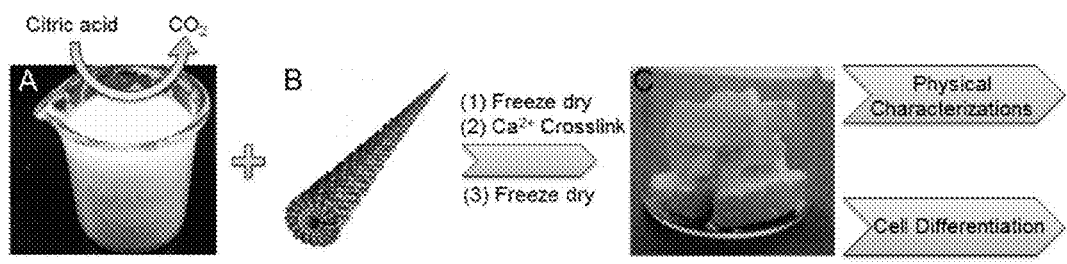

FIG. 27 shows a schematic of a synthetic procedure of generating virus functionalized porous composite hydrogels. Functionalization of composite hydrogels for use in stem cell cultures can be achieved through direct mixing of virus solution to the foamy mixture of alginate. Step A: Alginate mixture comprised of low viscosity alginate, Pluronic F108, sodium bicarbonate with an equivalent amount of citric acid to generate gas template foamy mixture. Step B: TMV was added 5 min before the foamy mixture was frozen and lyophilized. The lyophilized sample was crosslinked with $CaCl_2$. Step C: Porous composite hydrogel was obtained after dialysis against 0.1 M $CaCl_2$ and lyophilization.

Figure 28:
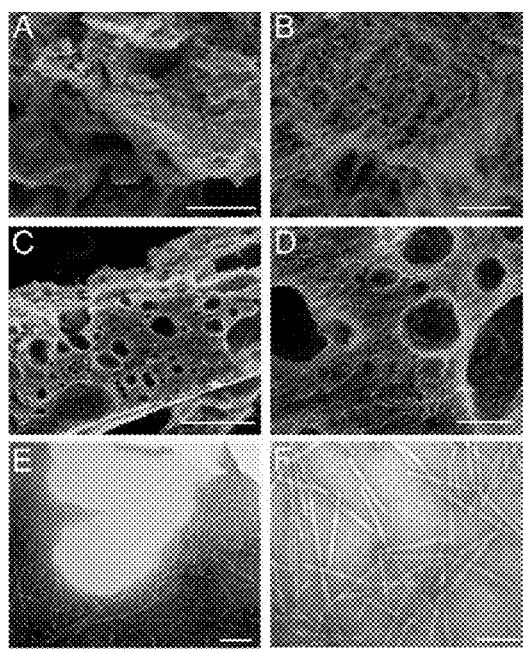

FIG. 28 shows Scanning electron micrographs of hydrogels and TMV particles labeled A-F: (A) and (B) PAH at different magnifications; (C) and (D) TMV-PAH at different magnifications. The images of TMV-PAH reveal larger macropores and interconnecting channels than PAH. Transmission electron micrographs of (E) intact TMV particles released from TMV-PAH after decrosslinking with EDTA, and (F) purified native TMV particles in buffer. Scale bars are 500 microns for (A) and (C), 100 microns for (B) and (D) and 200 nm for (E) and (F).

Figure 29A:
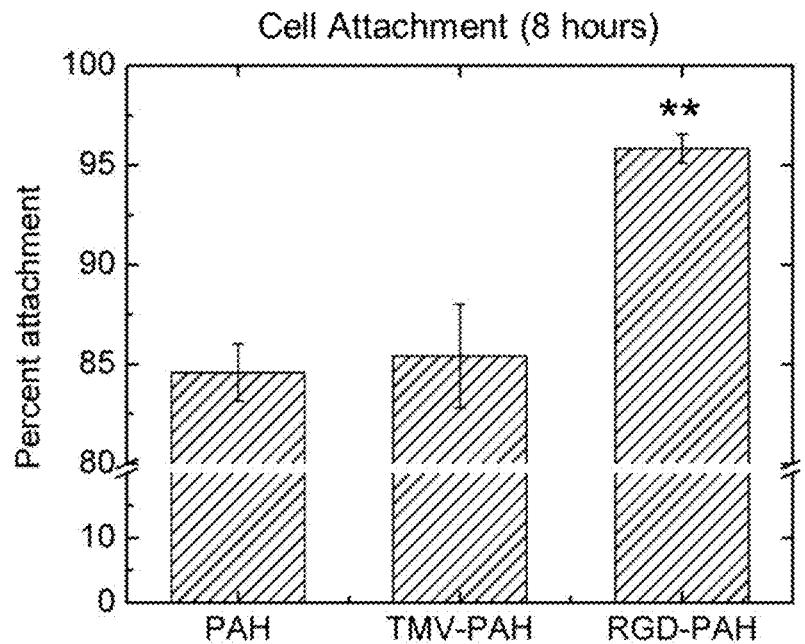

FIG. 29A shows cell attachment and viability in different types of porous composite hydrogels. Cell attachment was observed from counting the floating cells in the media after initial cell seeding for 8 h. Percent attachment of BMSCs in each type of hydrogels is presented. Values expressed are mean (n=3)±S.D.

Figure 29B:
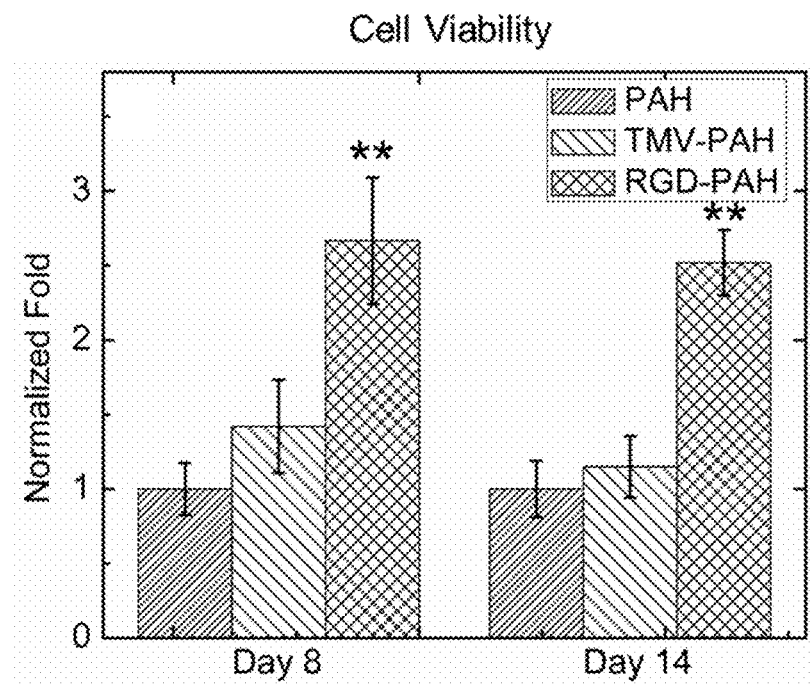

FIG. 29B presents CellTiter Blue® metabolic activity assay of BMSCs culture in different types of hydrogels at different time points. Values expressed are mean (n=3) ±S.D. of RFU that were normalized against PAH for each time point. Samples were compared using paired equal variance student t-test, **p<0.005.

Figure 30A:
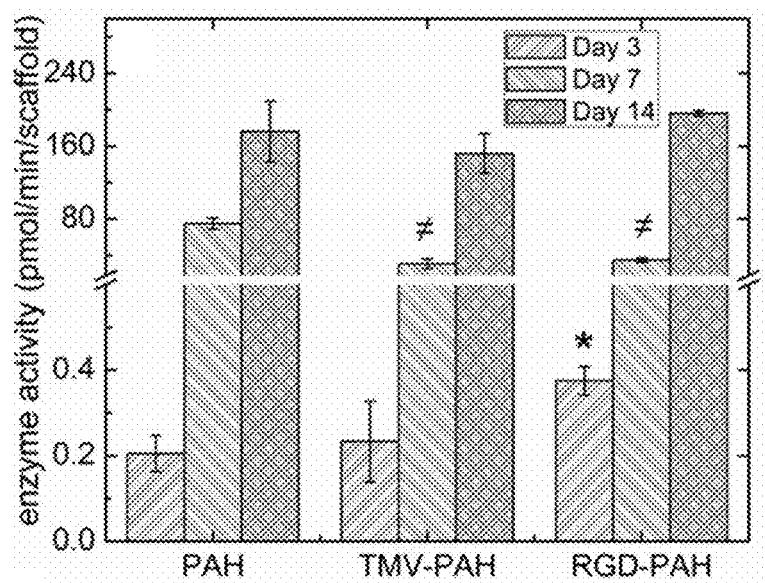

FIG. 30A shows results of osteogenesis assays of BMSC in porous composite hydrogels. ALP activity assay was performed on day 3, 7, and day 14 of osteogenic culture. Values expressed are mean (n=3)±S.D., ≠/*paired equal variance Student t-test, p<0.05.

Figure 30B:
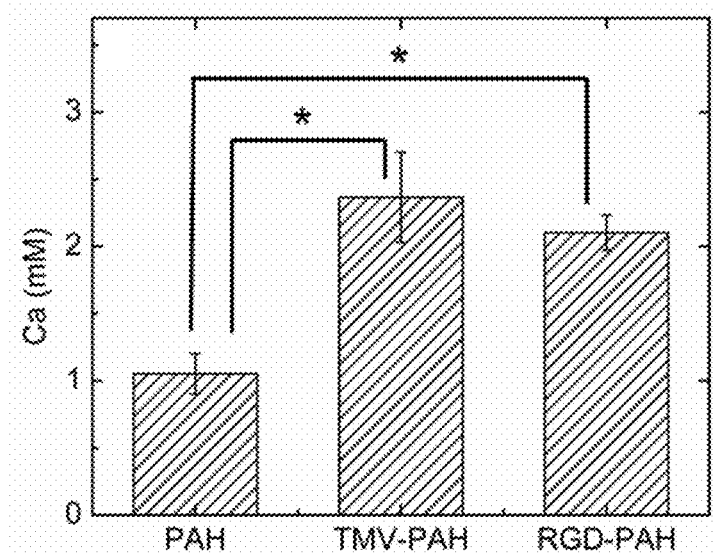

FIG. 30B shows calcium deposition quantified by ICP-OES on day 6 after background subtraction from control samples with no cells. Values expressed are mean (n=3) ±SEM, *paired equal variance Student t-test, p<0.05.

Figure 30C:
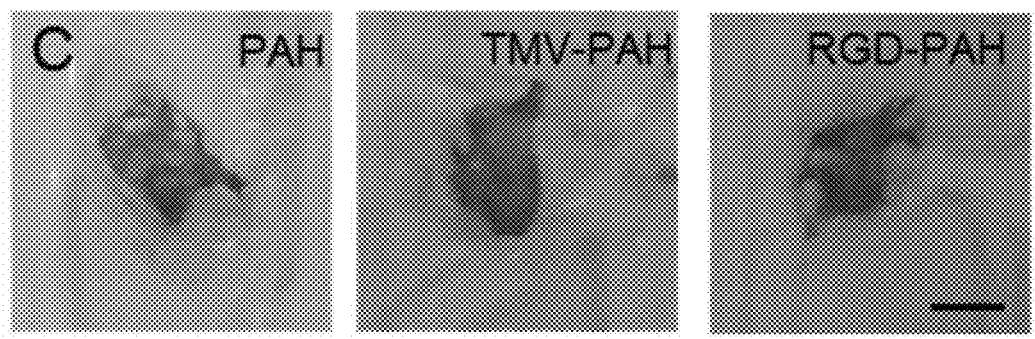

FIG. 30C: Thin sections of hydrogels stained with Alizarin red on day 14 cultures, scale bar=2 mm.

Figure 31:
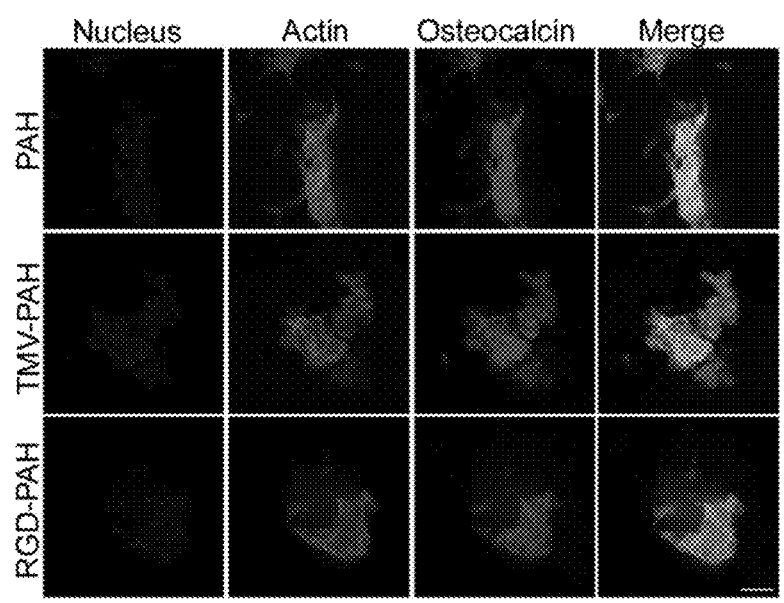

FIG. 31 shows confocal images of differentiated BMSCs in 3D composite hydrogels stained for nucleus ($1^{st}$ column), actin ($2^{nd}$ column), and osteocalcin (3rd column). Scale bar=50 microns.

DETAILED DESCRIPTION

Reference now will be made to the embodiments of the invention, one or more examples of which are set forth below. Each example is provided by way of an explanation of the invention, not as a limitation of the invention. In fact, it will be apparent to those skilled in the art that various modifications and variations can be made in the invention without departing from the scope or spirit of the invention. For instance, features illustrated or described as one embodiment can be used on another embodiment to yield still a further embodiment. Thus, it is intended that the present invention cover such modifications and variations as come within the scope of the appended claims and their equivalents. It is to be understood by one of ordinary skill in the art that the present discussion is a description of exemplary embodiments only, and is not intended as limiting the broader aspects of the present invention, which broader aspects are embodied exemplary constructions.

Methods are generally provided for adding cell binding sequences to the carboxy terminus of the TMV coat protein to promote cell attachment and cell differentiation.

In addition, we have confirmed that other plant viruses, including cowpea mosaic virus, turnip yellow mosaic virus, potato virus X, can also be employed in the cell culture studies using similar protocol listed in this invention disclosure. However, to simplify the writing, we use TMV in the text and the protocol, which can similarly be adapted to other virus systems.

EXAMPLES

Based on the above discussion, several genetically-modified TMV mutants were designed with reported cell adhesion sequences to expand the virus-based tools for cell studies. To assess whether TMV exhibit any natural affinity towards mammalian cell types, the cells were seeded in serum-free conditions on surfaces coated with TMV and TMV mutant particles. The attachment strengths of the cells were measured by an inverted centrifugation, and the results suggest that native TMV exhibit no specific cell attachment sequences. Among the cells cultured on glass substrates coated with mutant TMV particles, the cells on substrates coated with mutant virus expressing RGD tripeptide motifs, had formed filopodial extensions with weaker attachment profile. The cells on TMV expressing collagen I mimetic sequence (P15) displayed little spreading but higher attachment strength. These differences in cell morphologies and their associated spreading behaviors seem to suggest that the cells are using different sets of receptors to bind to the two substrates coated with the mutant viruses.

Among the reported TMV mutants that afforded higher binding affinities, one mutant (TMV-RGD1) was selected as a prototype to test whether substrates coated with the mutants enhanced stem cell differentiation. Two polyelectrolytes were used to alternatively coat the surface in order to stably integrate the virus to the surface. A specific serum-free osteogenic cultures was formulated to further enhance the cell differentiation from 14 days to 2 days. The virus-based cell cultures along with chemically defined serum-free cell cultures is a powerful model for studying how accelerated bone healing process occurs and potential use as a bio-scaffold in the medical community.

A step closer towards realizing the application of virus-based scaffolds as a medical tool was by transitioning from standard 2D coated substrates to 3D cultures. The transition from 2D to 3D is tantamount to studying cell behaviors in a more native setting, as the cells are naturally embedded within a 3D matrix. This transition from 2D to 3D alters many chemical and physical properties, and often the studies from 2D systems do not equally translate in 3D systems. The transition of TMV was realized by generating hydrogels through a gas templated solid foam assembly method reported by Barbetta et al. The primary materials were biodegradeable polysaccharide (alginate), a biocompatible polymer as a surfactant (plurionic F-108), and virus particles. The virus particles incorporated in the hydrogel were structurally intact and surface accessible, as demonstrated by increasing cell affinity towards hydrogels made with TMV-RGD1 mutant. Stem cell differentiation and viability were measured within the hydrogel. Alkaline phosphatase activity at early time points suggest more of the stem cells commit towards osteogenic lineage when cultured in 3D systems with TMV particles. Calcium mineralization occurs earlier for the stem cells in TMV and TMV-RGD1 hydrogels when compared to no virus hydrogel controls.

Besides the unique nature of TMV, other biologically relevant functional groups can be engineered to alter the scaffolds (2D and 3D) for better therapeutic applications.

1. Mutation of Tobacco Mosaic Virus

Biological functions were incorporated by inserting sequences derived from extracellular matrix proteins to enhance cell binding to the plant virus particles. The results herein show that native TMV has no apparent cell binding ligands based on our experimental conditions, and several mutants containing cell binding amino acid sequence inserts were stably expressed in tobacco plant host. Among the mutant CP sequences designed, five allowed systemic infection and were purified with moderate virus yields from the tobacco hosts. In order to screen the functionality of the mutants, we adapted a centrifugal adhesion assay, in which the average attachment strengths between large population of cells and substrate could be quantitatively measured with simple and reliable method. The method allowed for measuring the functionality of the mutants in biological system in a low-cost and highly reproducible manner, whereas previous studies required high investment of specialized media, time and delicate bone marrow stem cells harvested from animal hosts. Based on the centrifugal assay, one particular mutant based on collagen I peptide mimic (P15), provided the strongest attachment profiles, whereas the commonly used RGD mutants exhibited much lower detachment forces. In contrast, a peptide fragment derived from collagen I (DGEA (SEQ ID NO: 4)) and the synergy site of fibronectin (PHSRN (SEQ ID NO: 55) appeared to have slight benefit in promoting cell adhesion when displayed on the viral particles. This reported centrifugal assay will facilitate screening larger arrays of virus CP mutants prior to transferring the platform for in-depth study with stem cells.

Figure 1A:
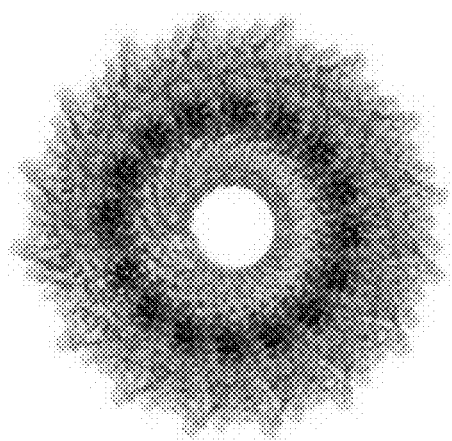
FIG. 1D shows a transmission electron microscopy image of an isolated TMV mutant, TMV-RGD1, with scale bar of 200 nm.
FIG. 1E shows an atomic force microscopy height image of TMV-RGD1 dried on a surface (2.5×2.5 microns).
Figure 1B:
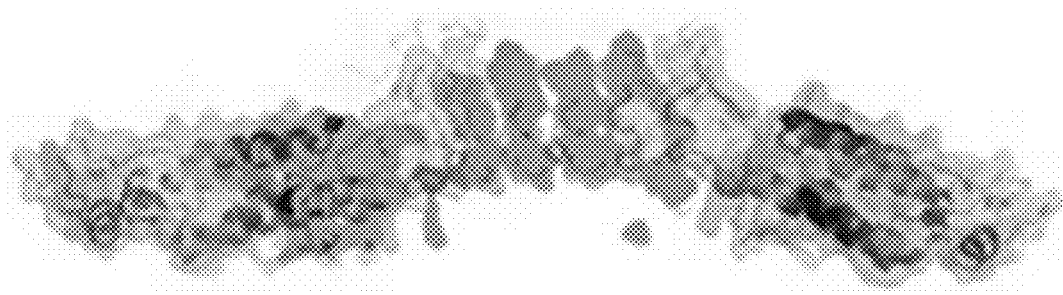
Figure 1C:
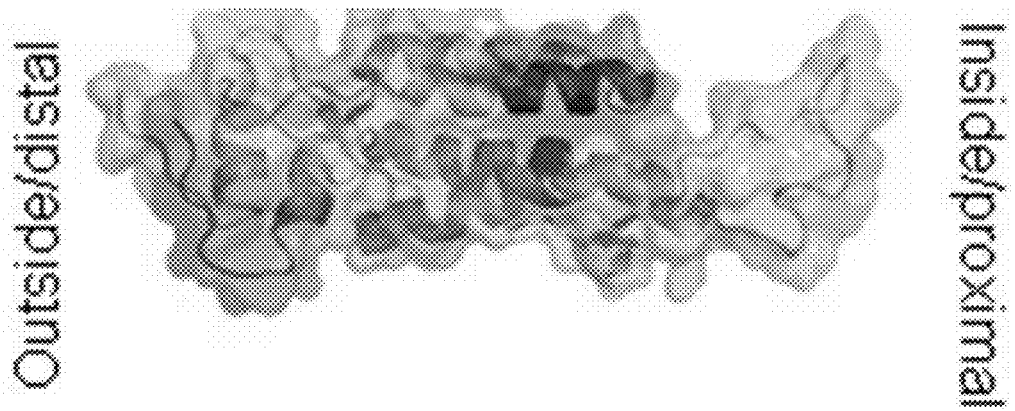
Figure 1D:
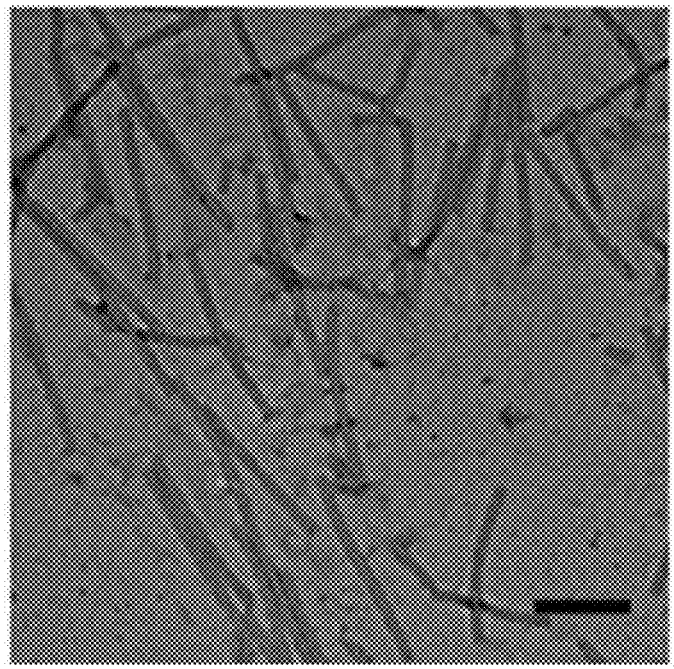
Figure 1E:
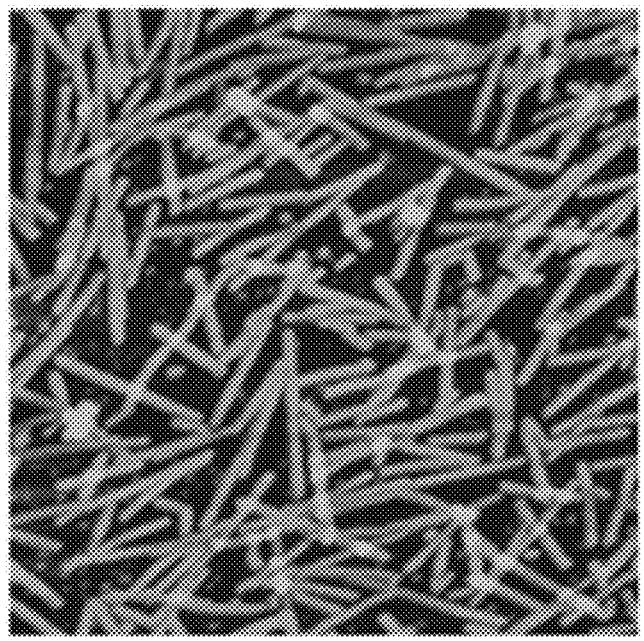

TMV has been well characterized since its initial discovery in the late 19th century. Recent studies with viruses as nanosized materials have renewed interests in manipulating the surface properties of the TMV capsid without disrupting its overall structural integrity and morphology for the differentiation of mesenchymal stem cell towards osteoblasts. The site of insertion was based on other studies with TMV, where majority of the papers reported to be near the carboxy terminus of the viral coat protein (FIG. 1A, FIG. 1B). The genetic modification was based on previous reports of TMV tolerating large inserts near its carboxy region (FIG. 1C). The amino acid sequences were selected based on peptide fragments reported to bind integrin receptors or partial sequences derived from other integrin binding matrix proteins (i.e. collagen, vitronectin, fibronectin, and integrin-binding sialoprotein) with sequences ranging from 4 amino acids up to 15 amino acids. Majority of the inserts were designed to not deviate from the original isoelectric point of the CP to avoid issues with virus infectivity in the tobacco plant hosts.

Nine RGD mutants, 3 fibronectin synergy mutants (PHSRN (SEQ ID NO: 55)), and two collagen mimetics were designed in total (Table 1). Of the 14 mutants designed, five allowed systemic infection in tobacco hosts (Table 2). The maximal yields for the mutants ranged from 3% to 50% of the unmodified virus particles with varying stabilities (Table 3). The low efficiency could be attributed to multiple factors, ranging from transfection efficiency by mechanical abrasion, inability of mutant CP to form the capsid, aberrant interactions with other integral proteins in the host, poor propagation of the mutant virus in the plant host or susceptibility of the host strain (*N. benthamiana* vs *N. tabacum* cv Samsun). The low transfection efficiency observed with mechanical abrasion can be circumvented by using agrobacteria-based infiltration. Alternatively, a library-based passage and selection scheme reported by Smith et al. could overcome some of the limitations observed with single mutant infections reported here to generate the mutants. In any case, the expression of recombinant proteins with viral vectors in any host will be limited by host tolerance.

TABLE 1

List of isolated TMV mutants (SEQ ID NOS 1-5, respectively, in order of appearance)

| Mutants | Insert Sequence | Calculated Mass (m/z) | Observed Mass (m/z) |
|---|---|---|---|
| RGD1 | GRGDSPG | 18161 | 18161 |
| RGD7 | AVTGRGDSPASS | 18621 | 18622 |
| PHSRN3 | EDRVPHSRNSIT | 18927 | 18926 |
| DGEA | DGEA | 17908 | 17905 |
| P15 | GTPGPQGIAGQRGVV | 18910 | 18896 |

TABLE 1

Virus yields and stabilities

| Mutants | Yield (mg/g of leave) | Stability[*] |
|---|---|---|
| Wild Type TMV | 2-3 | 1 |
| RGD1 | 0.5-1 | 1 |
| RGD7 | 0.5-1 | 1 |
| PHSRN3 | 0.1-0.2 | 3 |
| DGEA | 1-2 | 2 |
| P15 | 0.1-0.2 | 4 |

[*]1—very stable (6 months at 4° C.); 2—stable (3-6 months at 4° C.); 3—fairly stable (2-3 months at 4° C.); 4—poor stability (<2 months at 4° C.)

All five mutants were isolated in large quantities (>100 mg) using the standard purification methods used to purify wild type TMV. The structural integrity of the mutant viruses was verified by sucrose gradient centrifugation, transmission electron microscopy (TEM) and atomic force microscopy (AFM) (FIG. 1B, FIG. 1C). In addition, the final ultracentrifugation step in the purification protocol eliminates any incomplete assemblies of the virus particle. Therefore, obtaining any purified isolates of the mutants can be seen as clear indication of its structural integrity. The genetic insertions encoding for the peptide sequences fused to virus CP were verified by RT-PCR sequencing of the extracted virus particles and mutant protein expression was confirmed by MALDI-TOF MS (FIG. 2A). The genetic stabilities of the mutants were also confirmed by using the plant sap from infected plants to introduce the mutants to new tobacco

TABLE 2

List of TMV mutants (SEQ ID NOS 1, 6-10, 2, 11-14 and 3-5, respectively, in order of appearance)

| Mutants | Insert Sequence | Insert Site | Calculated Mass (m/z) | Observed Mass (m/z) |
|---|---|---|---|---|
| RGD1 | GRGDSPG | Extended after T159 | 18161 | 18161 |
| RGD2 | GAGSGRGDSGA | Inserted between S155-G156 | 18408 | n/i* (no infection) |
| RGD3 | TGRGDSPASS | Deleted G156-T159 and extended from S155 | 18124 | n/i |
| RGD4 | GEPRGDTYRA | Deleted G156-T159 and extended from S155 | 18311 | n/i |
| RGD5 | AGSGRGDSGA | Inserted between S155-G156 | 18350 | n/i |
| RGD6 | GEPRGDTYRAY | Inserted between S155-G156 | 18801 | n/i |
| RGD7 | AVTGRGDSPASS | Inserted between S155-G156 | 18621 | 18622 |
| RGD8 | ENGPRGDNYRA | Inserted between S155-G156 | 18766 | n/i |
| RGD9 | AGSGEPRGDTYRASGA | Inserted between S155-G156 | 18621 | n/i |
| PHSRN1 | PHSRNG | Extended after T159 | 18183 | n/i |
| PHSRN2 | EDRVPHSRNS | Deleted G156-T159 and extended from S155 | 18387 | n/i |
| PHSRN3 | EDRVPHSRNSIT | Inserted between S155-G156 | 18927 | 18926 |
| DGEA | DGEA | Inserted between S155-G156 | 17908 | 17905 |
| P15 | GTPGPQGIAGQRGVV | Inserted between S155-G156 | 18910 | 18896 | hosts, a process known as passaging. RT-PCR sequencing and MALDI-TOF MS of the viral particles isolated from newly infected hosts showed no deviation from the original mutation, even after ten passages for all mutants. In previous mutagenesis studies with Cowpea mosaic virus, mutants were found to revert back to its original genotype, which raised concerns that TMV mutants in older passages would revert back to their original wild type sequence. However, we have yet to observe such reversions in any of the mutants reported here.

2. Initial Cell Culturing Studies

The functionality of the TMV mutants was screened by coating the virus particles on high binding 96-well plates. The coating density optimization was determined by fluorescently labeling the carboxyl groups exposed to the interior surface by carbodiimide chemistry. The maximal fluorescence intensity was achieved by coating for 20 minutes with the virus solution concentration of 0.1 mg/mL (FIG. 2B). The virus coated plates were seeded with a large population of BHK or CHO cells for one hour in serum-free media. These two cell lines, unlike fibroblasts, express lower levels of extracellular matrix proteins and allow for the direct observation of the cell attachment to the substrate without adding inhibitors such as cycloheximide. Furthermore, avoiding the use of serum prevents proteins within the serum from adsorbing to the surface and promoting cell attachment. In this study, the surfaces coated with unmodified viruses behaved similarly to the negative controls (1% BSA coated), suggesting that the TMV capsid lacks specific cell binding motifs for the two cell lines tested here. Although in previous stem cell cultures, rapid cell differentiation was observed on the same wild type TMV capsids, several differences in the culture methods make it difficult to directly compare these two results. First, a different cell type was used. Some cells can secrete large quantities of ECM proteins, which may displace or interact with the underlying virus coatings. How these matrix proteins may interact with the virus provide additional variables. Furthermore, previous studies relied on extensive use of serum, which contains many cell-binding proteins (fibrinogen, collagen, growth factors). In this experimental system, we focused on the ability of the native virus and its variants to interact with two types of mammalian cell lines, baby hamster kidney (BHK) cells, which are known to produce low levels of extracellular matrix proteins and Chinese hamster ovarian (CHO) cells, which are commonly used for suspension cultures and adhesion cultures. Relative ease in culturing these cell lines and their low level of matrix protein provided us with simple, yet reliable means of screening the virus coated substrates. Based on these two cell lines, no apparent cell binding was observed for the native TMV capsid.

Prolonged storage at 4° C. was detrimental to the virus mutants with inserted peptide sequences often cleaved. Partially cleaved products were observed by MALDI-TOF MS (FIG. 3), which corresponded to loss of peptide fragments from the carboxy end (Table 4). These cleaved mutants still appeared to be structurally similar to that of wild type when observed under TEM, but did not promote cell attachment (data not shown). The genetic sequences, when analyzed by RT-PCR sequence, were unaffected and despite the protein degradation, these viral particles still infected and propagated in plant hosts. Non-degraded viral particles were recovered from the newly infected plant hosts, which suggest the observed degradations of the CPs are due to the presence of trace amounts of plant proteases or a low level of microbial contamination. Use of protease inhibitors during purification and storage decreased degradation. Storage of the viruses in −20° C. with a single freeze/thaw cycle did not change the structural features. Smaller rodlets (lengths<100 nm) were observed on TEM when virus underwent multiple freeze/thaw cycles (>3 cycles).

TABLE 4

The corresponding peptide loss associated with the truncated TMV coat protein. A mass difference of 17 is associated to the loss of a hydroxy ion. (SEQ ID NO:S 15-22, respectively, in order of appearance)

| | Mutants | Δm/z | Peptide loss |
|---|---|---|---|
| A. | RGD1 | 18159 − 17801 = 358 | DSPG (374) |
| | | 18159 − 17429 = 730 | TGRGDSPG (746) |
| B. | RGD7 | 18625 − 18123 = 502 | SSGPAT (519) |
| | | 18625 − 17754 = 871 | DSPASSGPAT (889) |
| C. | PHSRN3 | 19001 − 17399 = 1602 | RPHSRNSITGPAT (1394) |
| | | 19001 − 17399 = 1602 | DVRPHSRNSITGPAT (1608) |
| D. | DGEA | 17905 − 17372 = 543 | EAGPAT (545) |
| E. | P15 | 18928 − 17485 = 1443 | GPQGIAGQRGVVGPAT (1465) |

3. Cell Adhesion Depending on the Sequence of Peptide Insertion on Tobacco Mosaic Virus For BHK cells, the uncoated substrates promote strong attachment with the expected pyramidal shaped spreading (FIG. 4). These surfaces were used as positive controls. A small number of unattached, rounded cells could also be observed on these substrates, and these cells were immediately removed after the first round of centrifugation at relative centrifugal force (RCF) of 10 g (equals to detachment force of 1.2 pN/cell based on Eq. 1).

$$F_D=(\rho_{cell}-\rho_{media})\cdot V_{cell}\cdot RCF \quad \text{(Eq. 1)}$$

Based on the study by Reyes and Garcia, the detachment force (FD) imposed per cell can be calculated based on RCF multiplied by the cell mass. For mass calculation, we assumed similar parameters as stated in previous study, where $\rho_{cell}$=1.07 g/$cm^3$ and $\rho_{media}$=1.00 g/$cm^3$ with $V_{cell}$~1700 $cm^3$. The advantage of the inverted centrifugal assay is that the system is simple yet provides several quantifiable variables. By altering variables such as proteins, cell types, seeding times, relative centrifugal forces, the assay can provide robust statistics for quantifying cell adhesion as a standard method for high-throughput screening of virus coated substrates.

For the cells seeded on TMV and BSA coatings, we observed a large population of the rounded cells, which were immediately removed upon the first round of centrifugation, which indicates that the cells poorly adhere to native TMV (FIG. 4). The BHK cells seeded on the TMV-RGD1 mutant exhibited a bipolar cell shape with long spindle shape morphology. Similar morphology was also observed on cells cultured on TMV-RGD7 mutant, which contains longer flanking sequences derived directly from fibronectin. The cells on the other mutants, TMV-PHSRN3, -DGEA, and -P15 remained rounded with no filopodial extensions.

The cells on both RGD mutants had similar attachment profiles after the first round of centrifugation, whereas the cells on PHSRN (SEQ ID NO: 55) and DGEA (SEQ ID NO: 4) had much weaker attachments (FIG. 5A). The mutant containing collagen I peptide mimetic (P15) showed the highest level of cell attachment, resembling similar cell attachment levels to positive controls (FIG. 5A). The cells on TMV-P15 did not possess the pyramidal or the spindle shape, which is traditionally associated with spreading cells. Despite the lack of lamellopodial or filopodial extensions, the cells on TMV-P15 exhibited the highest attachment strengths. After a 30 g spin, approximately 50% of the cells detached from the RGD mutants (TMV-RGD1 and -RGD7), and majority of the cells were detached for cells on TMV-PHSRN and TMV-DGEA (FIG. 4 and FIG. 5B). The initial cell body sizes on the various mutants did not provide a (FIG. 5C). Despite the cell shape, the attachment strengths for the cells on TMV-P15 closely resembled to that of the uncoated wells even after the highest centrifugal force tested.

The centrifugal adhesion assay of the TMV mutants had been performed with another mammalian cell line, CHO cells. These cells also secrete little to no extracellular matrix proteins, therefore making it an ideal candidate to observe how the cells interact with the substrates. At RCF of 10 g, approximately 60% of the cells remained attached for the CHO cells for the positive controls, and for cells on TMV-RGD1 and TMV-P15 (FIG. 7). Similar to the previous results, the cells on uncoated surfaces exhibited pyramidal morphology which is typically observed for cultures on standard tissue culture polystyrene plasticwares. TMV and BSA blocked the cell attachment and the RGD1 insertion restored cell attachment. The cell spreading was again limited to a spindle shape with thin filopodial protrusions, again similar to the morphologies observed for BHK cells. However, TMV-RGD7 coated substrates did not promote attachment as strongly as the RGD1 variant for the CHO cells (FIG. 6). The mutant containing fibronectin synergy site, TMV-PHSRN3, and the short collagen I mimetic (TMV-DGEA) had lower attachment strengths with no apparent cell spreading. TMV-P15, again showed strong attachment profile, similar to that of the uncoated and RGD1 variant, but the cells still did not show long filopodial protrusions. The mutants with collagen I peptide mimetics, TMV-DGEA and TMV-P15, pose an interesting dilemma. Based on the weak attachment profiles for TMV-DGEA, the short insert could be sterically hindered and therefore it fails to bind to the corresponding receptor, whereas the longer 15 amino acid insert of P15 is more accessible and thereby allowing it to bind to cell surface receptors.

4. Specific Integrin Proteins can Interact with Mutant Tobacco Mosaic Virus

Specific integrin receptors were blocked with monoclonal antibodies ($\alpha 2$, $\alpha 5$, $\alpha V$, $\beta 1$, $\beta 2$) for three mutant substrates that showed the highest binding strengths (RGD1, RGD7, P15). Cell attachment was unaffected by anti-$\alpha 2$, $\alpha 5$, $\beta 2$ antibodies for cells seeded on TMV-RGD1 coated substrates (FIG. 5D). Since alpha subunit of integrin receptors do not possess the RGD binding pocket, it is reasonable that cell binding is unaffected when blocked with anti-alpha antibodies. Only a minor drop (~25%) in attachment was observed for cells on RGD1 when blocked with anti-$\beta 1$, which suggests that RGD1 mediates attachment through the vitronectin ($\alpha V \beta 3$) receptor rather than through fibronectin or collagen receptors ($\alpha 5 \beta 1$ and $\alpha 2 \beta 1$, respectively). For the cells seeded on RGD7, attachment is drastically reduced with the anti-$\beta 1$ antibodies (FIG. 5E). This specific reduction by anti-$\beta 1$ antibodies suggests that RGD7 mediates cell attachment more through the fibronectin receptor than through the vitronectin receptors. However, additional studies will be necessary to determine whether these mutants are truly specific for one integrin receptor type. For the cells seeded on collagen mimic, TMV-P15, anti-60 2 and -$\beta 1$ antibodies reduced attachment to 30% and 55% of controls, whereas the cells treated with anti-$\alpha 5$ or -$\beta 2$ showed no statistically significant reduction in attachment (FIG. 5F). Interestingly, anti-av treated cells exhibited a drop in attachment. Ongoing studies involving receptor binding affinity, downstream molecular events, and focal adhesion complexes on these mutants will shed some light to how these multivalent protein scaffolds affect cell surface receptors, their downstream molecular signals, and ultimately the cell behaviors.

The cell morphologies for two samples were closely inspected by scanning electron microscopy (SEM) with the BHK cells cultured on TMV and TMV-RGD1. To facilitate the imaging process under high vacuum and sample handling for SEM, the cells were seeded on glass coverslips and limited to two distinctive samples. The morphological feature of cells on TMV and TMV-RGD1 were observed by higher magnification (FIG. 7), where only on the TMV-RGD1 coated substrates, the cells possess long filopodial extensions while still retaining rounded cell bodies. The cells on TMV coated surface remain rounded with short extensions around the cell body. These long bipolar cell body shapes are typical for many of the BHK cells cultured on the RGD variants (TMV-RGD1 and -RGD7).

5. Bone Tissue Differentiation Studies

Based on models of infectious viruses and the importance of ligand/receptor clusters, we rationalized that plant viruses can function as non-infectious, multivalent probes for studying complex ligand/receptor interactions. Moreover, the compatibility of viruses for cell cultures has been well documented by several groups. M13 bacteriophage engineered to display cell binding motifs were assembled into tissue engineering matrices to support neural cells and to control the directionality of cell growth. Previous studies in our group demonstrated that substrates coated with plant viruses supported mesenchymal stem cell growth and accelerated differentiation. The stem cells cultured on modified phosphate modified Tobacco mosaic virus (TMV) had increased calcium mineralization and had higher expression levels of genes related to bone formation, or osteoblastogenesis.

We hypothesized that cell differentiation on plant viruses could be further improved by addressing three parameters. First, a cell binding motif, GRGDSPG (SEQ ID NO: 1), was extended from the carboxy end of TMV coat protein to promote attachment. The RGD sequence is based on the well-known RGD tripeptide sequence to target integrin receptors and the flanking sequences are derived from the fibronectin sequence. As a control substrate, recombinant human fibronectin (hFN) was used. Second, the cells were cultured in chemically defined, serum-free media with growth factor supplements. Bovine serum contains xenogeneic proteins and growth factors, and therefore cannot be used for ex vivo implant models. The selection of growth factors was based on previous studies shown to enhance bone differentiation of mesenchymal stem cells. And lastly, layer-by-layer assembly was used to ensure stable display of the virus on the substrate (FIG. 8A). Poly(allylamine) hydrochloride was selected due to its primary amines, which has a positive charge upon protonation and can electrostatically bind the viruses to the substrate, as verified by atomic force microscopy (FIG. 8B). The cells were cultured with osteo-inducing factors (dexamethasone, L-ascorbic acid 2-phosphate, and $\beta$-glycerophosphate), 1×ITS (insulin, transferrin, and selenium) and growth factors8 (bFGF, TGF-$\beta 1$, EGF) in serum-free media for 2 days. All substrates showed relatively similar cell viability as determined by CELLTITER BLUE™ cell viability assay (FIG. 8C).

The average deposition density of virus (~1 µg/cm$^2$) on PEMs was measured by quartz crystal microbalance (FIG. 9 and FIG. 10).

BMSCs attached and spread on all substrates within one hour of seeding (FIG. 11A), followed by aggregation of cells on TMV-RGD1 within 48 hours of culture (FIG. 11B). The cell aggregates on TMV-RGD1 resembled the bone nodules observed in previous cultures. However, previous cultures required extended incubation time of up to 14 days, whereas here we observe similar phenomenon within 48 hours (FIG. 11B). The nomenclature of the mutant was classified as previously reported.

6. TMV on Surface Alters BMP2 and IBSP Gene Expression

For the characterization of the cells cultured on the various substrates, we probed for key osteogenic markers (BMP-2, osteocalcin and calcium sequestration). Kaur et al reported that unmodified TMV was a potent modulator of bone differentiation with rapid increase in bone morphogenetic protein-2 (BMP-2) gene expression within the first 24 hours of osteoinduction. The result suggests that bone differentiation on the virus substrate is mediated through the upregulation of BMP-2 expression.

We further examined the temporal changes in gene expression involved in early differentiation (ALPL, BMP2 and IBSP) for cells cultured on TMV coated substrates, cells supplemented with TMV in solution, and cells cultured on conventional TCP (FIG. 12A-FIG. 12C). Although there was no significant difference in ALPL mRNA expression for cells cultured on the three different substrates after 8 hours, the expression significantly increased after 24 hours in cells cultured on TMV substrate. For cells cultured on TMV coated substrates, BMP2 expression levels were six-fold higher than uninduced cultures after 8 hours of osteoinduction. In comparison, the cells in traditional cultures had only slightly increased BMP2 gene expression by two-fold (FIG. 12B). The initial increase in BMP2 gene expression for TCP had diminished back to basal level after 24 hours, whereas the cells cultured on TMV coated substrate still maintained higher BMP2 gene expression levels, a three-fold increase over TCP substrates (FIG. 12B). Although the addition of TMV as a solution supplement to the culture media resulted in a modest increase in BMP2 expression at 24 hours, it failed to provide the same effects as the virus-coated substrates. The initial results with TMV in solution indicate that the coating of the virus to the solid support is necessary to affect early BMP2 gene expression and the virus itself does not act as a soluble inducer. The results also suggests that TMV coated substrates enhance osteogenic differentiation of BMSCs by increasing BMP2 mRNA levels.

In addition to increased BMP2 gene expression, mRNA levels for integrin-binding sialoprotein (IBSP), a secreted extracellular matrix protein required for hydroxyapatite formation, increased over time in both TCP and TMV samples. IBSP is an osteogenic marker associated with mineralizing tissues, hence the increase in IBSP gene expression within 24 hours is an important discovery in explaining the role of TMV in osteogenic differentiation. IBSP gene expression levels for cells grown on TMV were two-fold higher than those of TCP after 8 hours of osteoinduction and the difference further increased to five-fold after 24 hours (FIG. 12C). The addition of TMV as a solution to the culture media did not provide the similar increase in IBSP expression levels as TMV coated substrates (FIG. 12C).

The apparent increase in BMP2 and IBSP mRNA levels for the cells on TMV-coated substrates suggest that these two proteins are involved in the enhancement of osteogenic differentiation (FIG. 12B, FIG. 12C). The observed differences in gene expression of BMP2 and IBSP indicate that the surface coating with the virus moderates BMP2 and IBSP expression levels within the first day, and the virus itself does not act as a soluble chemical inducer, but rather as a substrate with unique topographical features, or offering a rough surface, at both nanometer and micrometer scales.

The increase in BMP2 mRNA expression level was corroborated by ELISA, showing a similar trend of BMP2 increase at 8 and 24 hours in osteogenic media (FIG. 13A). In comparison to uninduced controls, the cells on TMV coated substrates expressed four-fold and three-fold higher levels of BMP2 at 8 and 24 hours, respectively. For TCP culture, there was no significant increase in BMP2 production at either time points (FIG. 13A). Clearly, among the three growth conditions, only TMV coated surface induced a significant increase in BMP2 mRNA and protein expression after 8 hours of osteogenic induction.

Immunofluorescence imaging for BMP2 revealed that the morphogen is localized to the cell aggregates. As shown in FIG. 13B, BMSCs on TMV stained positive for BMP2 with higher fluorescence intensity at both time points. BMP2 was observed around the cells that formed nodules or aggregates. It is hypothesized that too strong substrate binding may inhibit osteogenic differentiation. Similar to the previous results, the cells with TMV in solution stained poorly for BMP2. The concentrations of secreted BMP2 in conditioned media from the three culture conditions were measured by sandwich based ELISA. Higher concentration of BMP2 was observed in media with cells on TMV substrate, compared to cells on TCP with and without TMV supplemented in the media. The concentrations ranged between 100-200 µg/mL (data not shown), which is consistent with that reported in an ultrasound-induced BMP2 secretion within 24 hours.

7. Enhanced Osteogenesis Requires TMV Coating on Substrate

The enhancement in bone differentiation was also assessed by measuring ALP activity and calcium deposition at day 7, 14, and 21. ALP is an early marker of osteogenesis and its activity mediates matrix mineralization. Although only minor upregulation of ALPL mRNA levels was observed by RT-qPCR after 24 hours, ALP enzyme activity assays over the course of 3 weeks showed significant differences at day 7 and 14 (FIG. 14A). Similar to the earlier results, the addition of TMV in solution does not increase ALP activity, and only the cells on TMV coated substrates had significantly higher enzyme activities compared to controls. The enzyme activity at day 21 diminishes to the same level for all samples, suggesting that the observed level may be a basal activity level of ALP during mineralization stage.

Calcium deposition was determined at day 14 by staining with Alizarin Red S. Small nodules of mineralized calcium were observed for controls and cells supplemented with TMV in solution, whereas the nodules were visibly larger for the cells on TMV-coated substrates (FIG. 14B). UV-Vis absorbance measurements of the extracted dyes indicated the cells on TMV substrate had double content of calcium compared to control (FIG. 14C). The addition of TMV solution does not enhance matrix mineralization. These results confirm our hypothesis that TMV provides a topographical cue to enhance osteogenic differentiation, likely by changing the surface roughness. The combined results from RT-qPCR, ELISA and immunostaining clearly indicate that BMP2 expression was significantly induced within 24 hour of induction with a peak expression level at 8 hours. The enhancement requires the virus as a substrate rather than as a solution supplement, suggesting the role of topography or surface roughness in TMV-mediated osteogenesis.

8. TMV Coating Alters Cytokine Expression, Actin Depolymerisation and Focal Adhesion We investigated the cells' response to the virus by screening such cytokines or other relevant growth factors which could affect early bone differentiation other than BMP2. Cytokine antibody arrays for 29 cytokines were used to screen the conditioned media from cells cultured on TCP and TMV coated wafers. The media consisting of primary media only was collected after 24 hours of culture and examined. Tissue inhibitor of metalloproteinases-1 (TIMP-1) was the only molecule secreted from both culture conditions, while cytokine-induced neutrophil chemoattractant 1 (CINC-1), CINC-2, MIP-3α, and vascular endothelial growth factor (VEGF) were detected from the conditioned media for the cells on TMV wafers (FIG. 15). According to Kim et al., CINC-1 and MIP-3α recruit neutrophils and monocytes to induce osteogenesis. However, the previous studies did not correlate these cytokines with enhanced BMP2 upregulation during osteogenesis. Future studies on the osteogenic effects of these individual cytokines may reveal their involvement in BMP2-mediated bone differentiation. It could possibly lead to a discovery of new biomaterials to elicit these cytokine productions in order to improve bone healing.

The remaining 24 cytokines, CINC-3, ciliary neurotrophic factor (CNTF), fractalkine, GM-CSF, sICAM-1, IFN-γ, IL-1 α, -1β, -1ra, -2, -3, -4, -6,-10, -13, -17, IP-10, lipopolysaccharide induced c-x-c chemokine (LIX), L-selectin, monokine induced by gamma interferon (MIG), MIP-1α, RANTES, thymus chemokine and TNF-α were below the detection limits of the cytokine array.

Since there was no established direct correlation of other cytokines and osteogenesis, cell morphologies were closely observed prior to osteoinduction. It was demonstrated that BMP2 production was highly localized around the cell nodules. The investigation of actin polymerization and organization was carried out to compare cells on TCP and TMV substrates prior to osteoinduction, at which time cell aggregation was first observed. The actin intensity by phalloidin staining was more intense in cells on TMV substrate, indicating higher activity from actin polymerization which could facilitate mobilization of cells to form nodules within 24 hours of cell seeding (FIG. 16). At higher magnification, cells on TCP surface maintained highly aligned sarcomeric striations, whereas cells on TMV substrate displayed non-aligned striations. These observations are similar to an experiment by Mendonca et al., which demonstrated that cells on a rougher surface topography exhibit an undefined long axis with thicker actin filaments leading to less initial cell spreading followed by enhanced mineralization.

The interaction between cell and ECM is mediated by cell surface receptors (i.e. integrins). Vinculins, part of focal adhesion complexes (FACs), couple the integrins to the cytoskeleton allowing crosstalk between ECM and intracellular signalling. Previous studies illustrated that increased localization of vinculin is associated with larger focal adhesion (FA) size and strengthening of adhesion leading to reduced cell motility. Smaller size of FAs suggests that BMSCs attached to TMV substrate weakly, whereas larger size of FACs dictates stronger cell-substrate adhesion. While BMSCs on standard TCP exhibited larger average vinculin size, indicating stronger adhesion to the underlying substrate, the cells on TMV substrate showed smaller FA sizes (FIG. 17A, FIG. 17B). The significantly smaller FA size for cells on is likely to increase cell motility and facilitate the formation of cell aggregates within 24 hours of seeding. Further studies are necessary to further establish the correlation of the focal adhesion of BMSCs on virus-coated substrates with the downstream responses.

9. TMV Mutants can Further Promote the BMP-2 Production and Osteogenesis

To determine whether TMV-RGD1 coated substrates can mediate similar response in BMSCs, the two day cultures were fixed and probed with anti-BMP2 antibodies. Significantly higher levels of BMP-2 were found for BMSCs on TMV-RGD1 (FIG. 18A, FIG. 18B) and localized only to the large cell aggregates which are only present on TMV-RGD1 substrates (FIG. 18A). An advantage of the virus is the multivalent ligand display capability. To probe for its effect on cells, we probed for focal adhesion kinase activity. Phosphorylation of FAK at Y397 is associated with increased activity of FAK, and such increase in FAK activity has been associated with multivalent ligands and increased osteogenesis (bone formation). An increase in focal adhesion kinase phosphorylation at residue Y397 was also observed for cells cultured on TMV-RGD1 coated substrates (FIG. 18C), two-fold above the levels detected for cells on human fibronectin (hFN) (FIG. 18D).

Expression of osteocalcin, a protein primarily expressed in mature bone cells (osteoblasts and osteocytes), was observed only in the cells grown on TMV-RGD1 substrates, whereas the cells on other substrates had little to no detectable levels (FIG. 19A). The cells were stained with Alizarin Red S, the cell aggregates stained red for calcium minerals (FIG. 19B). These cell aggregates, which resemble the typical nodules found in previous studies after 14 days of osteoinduction on TMV substrates, were formed within 2 days and stained positive for calcium with Alizarin Red, a typical cytochemical stain for calcium in cells undergoing osteogenesis. As the stem cells undergo bone differentiation, calcium is sequestered and mineralized with surrounding matrix proteins to form mineralized bone tissues. Higher intensity of the cytochemical stain is observed primarily for the cell clumps found on TMV-RGD1 coated substrates (FIG. 19B).

These adaptations significantly shortened the rate of our previous differentiation time requirement from 2 weeks to 2 days of osteoinduction. Previous studies indicate that mesenchymal stem cells are induced for two to three weeks to observe canonical osteoblast phenotypes. The results herein show that a TMV variant can promote cell differentiation and show calcium sequestration and expression of established osteogenic markers within two days of osteoinduction. These results suggest that virus-based biomaterials can function as alternative matrix mimetics to promote stem cell differentiation.

The rate of stem cell differentiation on TMV coated substrates was enhanced by manipulating three factors. The virus was genetically modified with a cell binding ligand. A chemically defined media and a stable display of the virus by layer-by-layer assembly provided robust culture protocol that supported rapid cell differentiation. In this study, we observed the typical bio-markers for bone induction within two days of culture, which is dramatically enhanced when compared to previous reports requiring 14 days for differentiation. The cells aggregated only on the TMV-RGD1 substrates, whereas the cells on hFN remained spread and stained poorly for calcium minerals. BMP-2 and osteocalcin, which are found in cells undergoing bone differentiation, were only found in cells cultured on TMV-RGD1 substrates. A study has shown that the primary amino groups on substrates enhance osteogenesis, and such groups are displayed on the polyelectrolyte (PAH), which is the top-most layer. However, the amino group alone cannot account for the increased number of nodules observed on TMV-RGD1 as shown in the results (FIG. 18, and FIG. 19). The enhanced rate of differentiation could be due to the cell binding peptide, but fibronectin coating does not provide the same rapid differentiation (FIG. 19).

10. New Coating Protocol for Preparing Homogeneous TMV Surface for Cell Culturing A major limitation of the layer-by-layer coating is the required multiple coatings of polyelectrolytes. While an automated process can be adapted to achieve a faster coating process, for general laboratory use, repetitive coating process requires long procedural time frames (20 hours to coat 5×24 well plates) when performed manually. To address this issue, a preliminary study was conducted using high binding plates without any polyelectrolyte coating. The results have indicated that the virus can be directly bound to the high binding 96-well plates by incubating 100 µl of the virus solution for 20 minutes at room temperature. Different concentrations of the virus solution ranging from 0.01 µg/mL to 100 µg/mL were used to monitor the optimal coating density on the high binding plates by ELISA (FIG. 20). The direct coating of virus on high binding plates were initially used for cell adhesion studies, but these initial studies indicate that surfaces are not fully covered by the virus particles.

Coating the high binding plates with virus and the different mutants slightly altered the hydrophobicity of the surfaces (FIG. 21). Original uncoated surfaces indicated a high water contact angle (~90°), and coating with wild type TMV increased hydrophilicity as indicated in a decrease in the water angle angle (~80°). The mutants TMV-RGD1, PHSRN3, DGEA further lowered the water contact, indicating increasing hydrophilicity. TMV-P15 and human fibronectin coatings retained a slightly more hydrophobic surface than the other three mutants.

The high binding plates coated with virus and the different mutants, then the plates coated with virus particles were seeded with rat bone marrow derived mesenchymal stem cells. Cell spreading was measured after staining the cells with Calcein-AM for 1 hour at 37° C. (FIG. 22). The cells were imaged by confocal microscope using GFP filters (FIG. 22A) and spreading was calculated by two different methods. In one method, the overall fluorescence intensity of each sample was measured using a fluorimeter (FIG. 22B), and the other method measured the area coverage per image frame (FIG. 22C). To calculate percent coverage, the area covered by the cells was divided by the total area of the frame. Three images per well was taken from 4 different wells (n=12 per sample). Despite the incomplete coverage of the virus particles on the high binding plates, the cells attached and spread on the TMV-RGD1 mutant in a similar manner to human fibronectin coated substrates.

rBMSCs seeded on the plates were treated with chemically defined serum-free osteogenic media for 21 days to initiate differentiation. Cell differentiation was monitored every 7 days by measuring alkaline phosphatase activity and calcium deposition (FIG. 23A-FIG. 23C). Higher level of enzymatic activity was observed for the cells cultured on TMV-RGD1 coated substrates in comparison to the cells cultured on other mutants and on unmodified TMV (FIG. 23A). This increased enzymatic activity indicating its progression towards osteogenic differentiation. However in comparison to the cells on human fibronectin (hFN) coated substrates, the cells cultured on TMV-RGD1 had equal or lower levels of enzymatic activity for the three time points examined. Since this particular enzymatic activity is reported to increase during mid-differentiation phase and to decrease during its final stages of differentiation, it remains to be discovered whether the cells on TMV-RGD1 had already reached maximal enzymatic activity prior or post day 14 of differentiation time point. Calcium quantifies for the differentiating cells were also calculated every 7 days on the various mutants including unmodified TMV and hFN coated controls. The increasing calcium levels suggest that the cells on TMV-RGD1 maintain its high rate of differentiation, similar to that of cells cultured on hFN coated controls (FIG. 23B) and the progression of osteogenic differentiation is similar to that of its alkaline phosphatase activity levels. Calcium levels for the cells cultured on the rest of the mutants increased on day 21 to the levels observed on day 14 for the cells on TMV-RGD1 and hFN coated substrates. The cells stained with Alizarin Red S dye for calcium deposits were imaged after day 14. The differentiating cells were imaged after 14 days of osteogenic differentiation (FIG. 23C). The red colored regions represent higher levels of calcium deposits around the stem cells. Based on these images, the cells appear to have low levels of calcium deposits and do not show full progression towards osteoblastic cells. Unlike the previous layer-by-layer coatings, these surface coatings appear to delay the cell differentiation rates.

Despite the potential use of the direct coating of virus on high binding plates, there are several drawbacks to this methodology. One drawback for using uncoated high binding plates is the virus coating consistency. Another limitation is the slow differentiation observed with chemically—defined serum free culture conditions. In the previous layer-by-layer assemblies, osteogenic differentiation was observed within 2 days of culture, whereas for the high binding plates, the cells still required prolonged culture periods (>21 days). Due to these limitations (slow differentiation and uneven virus coatings), alternative coating methods were sought. Surface coating optimizations to achieve even surface coatings and more consistent surface depositions were conducted.

Based on the previous results, an amine displaying polyelectrolyte appeared to be well suited for the cell differentiations. To maintain that amino group, a single layer of polyelectrolyte (polyallylamine hydrochloride—PAH) was used at different pH ranging from 4 to 13 (FIG. 24A-FIG. 24G). First, the densities of PAH deposited at different pH were monitored by QCM (FIG. 24A). The measurements indicated that raising the pH to the pI value of PAH (~9-9.5) resulted in the greatest amount of polyelectrolyte being deposited on the quartz surface (FIG. 24B). TMV depositions increased on surfaces coated with PAH solutions with decreasing acidity, with maximum depositions being reached around pH 9-11, then decreasing when pH levels of PAH solutions were further increased to 12 and 13 (FIG. 24C). These surface coatings were visualized as uncoated (FIG. 24D), PAH coated at pH 4 (FIG. 24D), pH 11 (FIG. 24E) and pH 11(FIG. 24F). The distinctive shape of TMV (rod-like) is more distinct on pH 4 (FIG. 18E), but the coverage appears to be less than 50% of the entire area. On the other hand, the rod-like particles are not visible on the high density coatings at pH 11 (FIG. 24F) and pH 13 (FIG. 24G). A trade-off between high density coatings and even coatings of TMV particles (high coverage with clearly visible side-by-side assemblies) appear to exist.

To further explore this balance of various factors pH, salt and virus concentrations, we examined virus depositions starting at PAH coating solution at pH 5, then using two different buffer pH's (5 and 8) and two different buffer concentrations (10 and 100 mM of potassium phosphate). The desired result was to find the factors that would allow for near complete coating of the surface with virus particles and side-by-side assemblies with high reproducibility.

Two major reasons behind this desired coating were:

1) Complete surface coverage would be better correlated to the changes in cellular behaviors, whereas partial coverage would allow the underlying layer to interact and possibly overwhelm the effects of the virus coatings;

2) All of the cell binding sequences are inserted along the longitudinal axis of the virus particle, therefore laying the virus particles on its side was essential to maximize the exposure of these ligands at its highest densities.

The deposition of the virus was monitored by AFM using TMV in 10 or 100 mM buffer either in pH 5 or 8. All substrates were prepared with PAH at pH 5 prior to coating with virus particles (FIG. 25). Based on the results, coating the virus particles at pH 8 alone gave to the least amount of particles on the surface, and lowering the pH of the virus solution to 5 increase deposition to the PAH coated surfaces.

The AFM results were further validated by QCM to monitor the deposition of the virus at the two different pH and buffer concentrations (FIG. 26). All substrates were prepared with PAH at pH 5 prior to coating with virus particles. Based on the results, coating the virus particles at pH 8 alone gave to the least amount of particles on the surface, and lowering the pH of the virus solution to 5 increase deposition to the PAH coated surfaces. Eliminating the salt, completely eliminated the inter particle charge screening and reduced coverage and deposition, as indicated by both QCM and AFM.

Testing these single PAH coatings for stem cell culture will be essential and verifying that these single layer coatings can provide the same rapid differentiation potential in chemically defined serum-free media will become the critical next step. Overall, we observe rapid stem cell differentiation in serum-free, chemically defined osteogenic media on genetically modified plant virus particles. This initial culture optimization in xeno-free cultures on multivalent scaffolds is an important step for the future development of ex vivo implant models. Furthermore, the virus is a powerful molecular tool that can be isolated consistently at low costs, with no observable cytotoxic effects, and the potential for large libraries of ligands (single or multiple) for dissecting some key regulating events in stem cell differentiation.

The underlying mechanism involved for this enhanced will require additional in depth analysis between the ligand sequence, mock sequence, varied ligand densities, substrate chemistries. One possible explanation is based on the interactions between virus, substrate, and growth factors to provide additive effects on bone differentiation to reduce the time required to observe osteo-typical markers. Additional comparative studies with collagen, other TMV variants, and structurally different viruses will provide further clues to the role of ligand organization, its effect on downstream signaling events (i.e. specific integrin receptors, FAK) and controlling the enigmatic stem cell behavior. The simplicity in altering the coat protein gene of TMV and the high yield of these virus variants from the plant host make these virus particles an attractive material for exploring how bionanoparticles can be used to control cell differentiation. The induction of rapid bone formation with autologous mesenchymal stem cells is highly relevant for future clinical applications where speedy ex vivo cultures of stem cells into bone tissues can ameliorate patients in urgent need of bone defect replacements.

11. Viral Particles can be used to Functionalize Biocompatible Porous Hydrogels

In regenerative medicine, synthetic extracellular matrix is crucial for supporting stem cells during its differentiation process to integrate into surrounding tissues. Hydrogels are used extensively in biomaterials as such synthetic matrices to support the cells. However, in order to mimic the biological niche of a functional tissue, various chemical functionalities are involved. We further developed a method of functionalizing highly porous hydrogel with functional groups by mixing the hydrogel with plant virus particles. Again, TMV and its mutants were used as the prototypical particles, while the methods can be extended to similar rodlike or spherical viruses.

Our approach is designed to be performed in a single pot with the sequential additions of reagents to ultimately incorporate biologically relevant functionalities in 3D scaffolds. TMV were introduced into the hydrogel by adding the non-infectious virus particles during the formation of gas template porous alginate hydrogels (PAH) (FIG. 27). The process involving no covalent modification and no further purification, which is contrary to peptide or protein conjugated hydrogels that require extensive dialysis to remove untethered peptides/proteins. The homogeneous mixture of alginate in bicarbonate solution with low concentration of surfactant (Pluronic F-108) is reacted with a mild acid (citric acid) to generate $CO_2$ in situ (FIG. 1A). The incorporation of the virus solution pursues and the entire foamy material is flash frozen and crosslinked. Additional procedures involving further dialysis and lyophilization provided the final PAH functionalized with the virus particles.

The initial characterization of the virus-incorporated PAH by ESEM revealed that the addition of the virus did not hinder pore formation with the macropore and interconnecting channels ranging between 10-500 microns for both PAH and TMV-PAH. In a close up magnification, PAH appears to have smaller pores and dense network (FIG. 28B), whereas large well-defined spherical pores (100 to 500 microns) are formed in TMV-PAH (FIG. 28D). The ESEM images show that the hydrogel formation is not hindered by the incorporation of the virus, but rather facilitates the formation of large, well-defined pores. The integrity of virus particles incorporated in PAH was assessed by de-crosslinking with EDTA to chelate $Ca^{2+}$ ions. This resulted in the subsequent release of TMV from PAH. TEM imaging of the dissolved TMV-PAH showed intact TMV particles (FIG. 28E), which were similar in size when compared to the TMV particles prior to incorporation (FIG. 28F). UV-Vis absorbance measurement of the de-crosslinked TMV-PAH solution could give the concentration of the TMV recovered that indicated that nearly all of virus could be retrieved after treating the hydrogel with EDTA.

The virus-incorporated PAH was also shown to have similar physical properties that could potentially assist 3D cell culture including swelling property, stability, and structural basis of pore architecture. The hydrogels could absorb water up to 7 folds of their initial dry weight indicating the extreme hydrophilicity as tissue-like environment and capability to uptake medium for cell culture. From the stability test, we observed no mass losses from PAH and TMV-PAH during the 4-week period that could support the entire cell culture experiments and suit for tissue engineering applications. As well as in thermal analysis, while MDSC data supported the incorporation of virus particles into PAH, we showed that TMV did not significantly impact the thermostability of original PAH as indicated by TGA. As there were no covalent modifications on the polymer chain structure, alginate still maintains their own properties and dominates as a bulk material. The amount of TMV released from TMV-PAH into the aqueous solution was measured and it confirmed that most TMV particles were entrapped in the hydrogel matrices even upon long term incubation in solution.

The incorporation of TMV in PAH did not at all impair the pore formation or the pore architecture. Interestingly, TMV-PAH (also RGD-PAH) gained larger extent of big pores. It is possible that TMV can facilitate and stabilize the macropore formation due to its coat protein amphiphilic property similar to other peptides and proteins. TMV particles could help trapping larger hydrophobic gas pockets upon the generation of $CO_2$ to better mediate the interfacial tension between aqueous and gas phases. The mechanical properties of stem cell microenvironments are well-recognized as one of essential determinants of differentiation fate. The mechanical environments that promote certain differentiation fates vary dramatically, with as much as 300-fold difference in elastic modulus between matrices that favor soft brain tissue (0.1 kPa) and decalcifying bone (>30 kPa). It is plausible that the alginate bulk is mechanically reinforced by the inclusion of TMV particles (resulting in increased stiffness at low strains), but the macro-porous architecture begins to collapse at higher strains causing a reduction in material stiffness. Considering the cell-scaffold interaction that happens at a low strain range near the original stage of compression, this increase in stiffness has reinforced the advantage to the virus incorporated hydrogel regarding bone tissue engineering.

12. TMV-hydrogel can Support the Cell Attachment and Differentiation

To demonstrate the potential use in cell cultures, cell attachment and viabilities were determined for the three types of hydrogels. In cell attachment assay, RGD-PAH (96±1%) had significantly higher cell attachment after 8 h. incubation than for PAH (85±3%). The incorporation of TMV did not provide any significant improvement to cell attachment when compared to the control (85±1%) (FIG. 29A). Based on the metabolic assay with CTB reagent, the cell viabilities in all three different types of hydrogels were determined for day 8 and day 14 cultures and normalized to metabolic rates of cells in PAH (FIG. 29B). The results indicate that BMSCs survived in both virus modified PAHs (TMV- and RGD-PAH) and the cells cultured on RGD-PAH continued to have the highest metabolic activity (FIG. 29B). However, there was no further increase in metabolically active viable cells from day 8 to day 14.

We seeded BMSCs in hydrogels and cultured in osteogenic media as an extension of our previous work on 2D substrates with virus particles. Osteogenesis was initially assessed by alkaline phosphatase (ALP) activity for day 3, day 7, and day 14 cultures (FIG. 30A). Low levels of enzyme activity were detected for all three samples for day 3 cultures, followed by markedly increases in ALP activities on day 7 and 14. The incorporation of the virus did not appear to hinder the differentiation potential as the same elevation trends of overall ALP activities were measured among the three groups from day 3 to day 14. Interestingly, RGD-PAH seemed to accelerate an early osteogenesis of BMSCs as the ALP activity was significantly higher among three samples on day 3. Although, on day 7, the higher level of ALP activity for PAH than the other two samples was unexpected. Calcium deposition in three types of hydrogels with BMSC osteogenic culture was quantified by ICP-OES (FIG. 30B). The average amounts of calcium deposited in both TMV-PAH and RGD-PAH after background subtraction from control samples without cells were higher than in PAH (FIG. 30B). All three types of hydrogels with BMSCs osteogenic culture were stained with Alizarin red giving intense red color (FIG. 30C).

Lastly, osteocalcin, a well-known osteospecific marker, was observed by immonostaining in cell-hydrogel cultures treated with osteoinductive media in PAH, TMV-PAH, and RGD-PAH. FIG. 31 illustrated the accumulation of osteocalcin after day 10 (PAH) and day 13 (TMV-PAH and RGD-PAH) and confirmed that virus incorporation into 3D matrices did not impair the differentiation potential of BMSC into osteogenic lineage.

The implication of this process resides with the three important features of TMV: its well-defined genetic/chemical modularity, multi-valency (its capsid is composed of 2130 copies of identical subunits), and its well-defined structural features. Previous studies utilizing the native TMV on 2-dimensional supports accelerated mesenchymal stem cell differentiation and genetically modified viral particles further enhanced cell attachment and differentiation. We demonstrate that functionalization of porous alginate scaffold can be achieved by addition of viral particles with minimal processing and downstream purifications, and the cell attachment and differentiation within the macro-porous scaffold can be effectively manipulated by altering the peptide or small molecule displayed on the viral particles.

General Procedure:

Virus Purification:

Wild type TMV and its mutant variants were purified according to previously reported method with slight modification. The infected leaves were collected and stored in Ziploc® bags (~100-150 g of leaves per bag) and stored in −80° C. freezer for later processing. For purification, the frozen leaves were crushed by hand inside the plastic bag, then transferred to a 1.5 L blender (Oster). Approximately 3 volumes of phosphate buffer was added to the crushed leaves with an addition of 0.2-0.3% 2-mercaptoethanol. The leaves were blended for 2 minutes at low setting then switched to highest setting for an additional 3 minutes. The blended plant sap was filtered through two layers of cheesecloth, then flow through was centrifuged at 13,500 rpm (Sorvall SLA1500) at 4° C. for 30 minutes. The resulting supernatant was then pooled together and mixed with n-butanol/chloroform at a ratio of 2:1:1 (plant sap:n-butanol:chloroform). The homogenate was stirred for 30 minutes on ice, then centrifuged at 12,500 rpm (SLA 1500) for 20 minutes at 4° C. The aqueous layer was transferred to a beaker and the virus was precipitated by adding 0.2 M NaCl and 8% (wt/vol) PEG-8000. The mixture was stirred on ice for 60 minutes, and centrifuged at 13,500 rpm (Sorvall SLA1500) for 20 minutes. The white precipitant was then resuspended with 10 mM K phos buffer (pH 7) supplemented with PMSF protease inhibitor (10 µg/mL final concentration). The solution was centrifuged at 9,500 rpm for 10 minutes at 4° C. to remove excess PEG. The supernatant was transferred to ultracentrifuge tubes (Beckman 50.2 Ti) and the virus was pelleted at 42,000 rpm at 4° C. for 2.5 hours. The virus pellet was resuspended in 100 mM K phos buffer (pH 7) overnight at 4° C. The virus solution was centrifuged again at 9,500 rpm for 10 min at 4° C. to remove insoluble debris. UV absorbance was measured at 260 and 280 nm wavelengths to determine the concentration of the virus. The virus concentration of 0.1 mg/mL has an absorbance of 0.3 at 260 nm and exhibits a characteristic 260/280 ratio of 1.26-1.27. The purified virus solutions were aliquoted and stored at -20° C. freezer.

Atomic Force Microscopy and Scanning Electron Microscopy:

Tapping-mode atomic force microscope (AFM) images were obtained at ambient conditions using Nanoscope IIIA MultiMode AFM (Veeco). Si tips with a resonance frequency of approximately 300 kHz, a spring constant of about 40 N m-1, and a scan rate of 0.75 Hz were used. For scanning electron microscopy, the cells were washed three times in 1×PBS at ambient temperature. Cells were then fixed using 4% paraformaldehyde for 15 minutes at room temperature. After which the cell samples were fixed with 0.1 M cacodylate buffer (pH 7.2), 1% $OsO_4$ for an hour at 4° C. The samples were washed several times in cacodylate buffer, and dehydrated in a series of ethanol solutions (50%, 70%, 95%) for 10 minutes each. The samples were immersed in 100% ethanol for the final dehydration step. The cells on the cover-slips were mounted on a stub and sputter coated with a thin layer of gold prior to imaging under FEI Quanta 200 ESEM.

Generation of TMV Mutants:

TMV coat protein gene was mutated using overlap-extension PCR. The TMV coat protein gene sequence for PCR was obtained by digesting U3/12-4 plasmid (TMV U1 strain) with NcoI and KpnI restriction enzymes. The digested fragment from the TMV U3/12-4 plasmid contained the entire TMV coat protein gene plus the 3' UTR of the viral genome. The fragment was inserted into cloning vector pBluescript SK(+) II. This plasmid was designated pCP-NK. Two complementary mutagenic oligos were made with the following list of primers. For the overlap extension mutagenesis, two PCR reactions were performed in parallel, MI3F primer was paired with the mutagenic forward primer while the M13R primer was paired with mutagenic reverse primer. The products of the two PCR reactions were gel purified and combined in a third PCR reaction using the M13F and M13R primers with the two previous PCR products as templates. This final PCR product was digested with NcoI and KpnI and cloned into the TMV U3/12-4 plasmid, which was designated TMV-RGD1. The mutated coat protein ORF was confirmed by sequencing. The plasmid was cut at the unique KpnI site and the linearized plasmid was transcribed using the MEGAscript T7 kit (Ambion) following the manufacturer's instructions. Ten micrograms of RNA per tobacco leaf was used for inoculation. For the rest of the mutants, the entire TMV genome was inserted 3' of a CaMV 35S promoter within a plasmid previously digested to remove the downstream TMV sequences. The original plasmid construct was designed in a pALTER-1 vector (pU1R 35S), which exhibited some instability. Therefore the entire TMV genome with the CaMV 35S promoter was transferred to a BlueScript vector.

TABLE 5

List of TMV mutants (SEQ ID NO:S 1, 6-10, 2, 11-14 and 3-5, respectively, in order of appearance)

| Mutants | Insert Sequence | Insert Site | Calculated Mass (m/z) | Observed Mass (m/z) |
|---------|-----------------|-------------|----------------------|---------------------|
| RGD1 | GRGDSPG | Extended after T159 | 18161 | 18161 |
| RGD2 | GAGSGRGDSGA | Inserted between S155-G156 | 18408 | n/i* (no infection) |
| RGD3 | TGRGDSPASS | Deleted G156-T159 and extended from S155 | 18124 | n/i |
| RGD4 | GEPRGDTYRA | Deleted G156-T159 and extended from S155 | 18311 | n/i |
| RGD5 | AGSGRGDSGA | Inserted between S155-G156 | 18350 | n/i |
| RGD6 | GEPRGDTYRAY | Inserted between S155-G156 | 18801 | n/i |
| RGD7 | AVTGRGDSPASS | Inserted between S155-G156 | 18621 | 18622 |
| RGD8 | ENGPRGDNYRA | Inserted between S155-G156 | 18766 | n/i |
| RGD9 | AGSGEPRGDTYRASGA | Inserted between S155-G156 | 18621 | n/i |
| PHSRN1 | PHSRNG | Extended after T159 | 18183 | n/i |
| PHSRN2 | EDRVPHSRNS | Deleted G156-T159 and extended from S155 | 18387 | n/i |
| PHSRN3 | EDRVPHSRNSIT | Inserted between S155-G156 | 18927 | 18926 |
| DGEA | DGEA | Inserted between S155-G156 | 17908 | 17905 |
| P15 | GTPGPQGIAGQRGVV | Inserted between S155-G156 | 18910 | 18896 |

TABLE 6

The corresponding peptide loss associated with the truncated TMV coat protein. A mass difference of 17 is associated to the loss of a hydroxy ion. (SEQ ID NO:S 15-22, respectively, in order of appearance)

| Mutants | Δm/z | | Peptide loss |
|---------|------|---|--------------|
| A. RGD1 | 18159 − 17801 = 358 | | DSPG (374) |
| | 18159 − 17429 = 730 | | TGRGDSPG (746) |
| B. RGD7 | 18625 − 18123 = 502 | | SSGPAT (519) |
| | 18625 − 17754 = 871 | | DSPASSGPAT (889) |

TABLE 6 -continued

The corresponding peptide loss associated with the truncated TMV coat protein. A mass difference of 17 is associated to the loss of a hydroxy ion. (SEQ ID NO:S 15-22, respectively, in order of appearance)

| Mutants | Δm/z | Peptide loss |
|---|---|---|
| C. PHSRN3 | 19001 – 17399 = 1602 | RPHSRNSITGPAT (1394) |
|  | 19001 – 17399 = 1602 | DVRPHSRNSITGPAT (1608) |
| D. DGEA | 17905 – 17372 = 543 | EAGPAT (545) |
| E. P15 | 18928 – 17485 = 1443 | GPQGIAGQRGVVGPAT (1465) |

TABLE 7

TMV mutant primers (SEQ ID NO:S 23-50, respectively, in order of appearance)

| Mutant | | Primer Sequence |
|---|---|---|
| RGD1 | Forward | TCT GGT CCT GCA ACT GGA AGA GGA GAC TCT CCA GGA TGA GGT AGT CAA GAT |
|  | Reverse | ATC TTG ACT ACC TCA TCC TGG AGA GTC TCC TCT TCC AGT TGC AGG ACC AGA |
| RGD2 | Forward | AGC GGC AGA GGC GAC AGC GGC GCC GGT CCT GCA ACT TGA GGT AGT |
|  | Reverse | GCT GTC GCC TCT GCC GCT GCC GGC ACC AGA GGT CCA AAC CAA ACC |
| RGD3 | Forward | AGA GGC GAC AGC CCC GCC AGC AGC TGA GGT AGT CAA GAT GCA TAA |
|  | Reverse | GGC GGG GCT GTC GCC TCT GCC GGT AGA GGT CCA AAC CAA ACC |
| RGD4 | Forward | GGC GAG CCC AGA GGG GAC ACC TAC AGA GCC TGA GGT AGT CAA GAT GCA TAA |
|  | Reverse | GGC TCT GTA GGT GTC GCC TCT GGG CTC GCC AGA GGT CCA AAC CAA ACC |
| RGD5 | Forward | AGC GGC AGA GGC GAC AGC GGC GCC GGT CCT GCA ACT TGA GGT AGT |
|  | Reverse | GCT GTC GCC TCT GCC GCT GCC GGC AGA GGT CCA AAC CAA ACC AGA |
| RGD6 | Forward | CCG AGA GGA GAT ACA TAC AGA GCA TAC GGT CCT GCA ACT TGA GGT AGT |
|  | Reverse | TCT GTA TGT ATC TCC TCT CGG CTC TCC AGA GGT CCA AAC CAA ACC AGA |
| RGD7 | Forward | GGA AGA GGA GAT TCA CCG GCA TCA TCA GGT CCT GCA ACT TGA GGT AGT |
|  | Reverse | CGG TGA ATC TCC TCT TCC TGT CAC TGC AGA GGT CCA AAC CAA ACC AGA |
| RGD8 | Forward | AAT GGA CCG AGA GGA GAT AAT TAC AGA GCA GGT CCT GCA ACT TGA GGT |
|  | Reverse | TCT GTA ATT ATC TCC TCT CGG TCC ATT CTC AGA GGT CCA AAC CAA ACC |
| RGD9* | Forward | CGC GGT GAT ACG TAC CGT GCG AGC GGC GCC GGT CCT GCA ACT TGA |
|  | Reverse | GTA CGT ATC ACC GCG TGG CTC TCC GCT GCC GGC AGA GGT CCA AAC CAA |
| PHSRN1 | Forward | TCT GGT CCT GCA ACT CCA CAC TCT AGA AAT GGA TGA GGT AGT CAA GAT |
|  | Reverse | ATC TTG ACT ACC TCA TCC ATT TCT AGA GTG TGG AGT TGC AGG ACC AGA |
| PHSRN2 | Forward | AGA GTG CCC CAC AGC AGA AAC AGC TGA GGT AGT CAA GAT GCA TAA |
|  | Reverse | TCT GCT GTG GGG CAC TCT GTC CTC AGA GGT CCA AAC CAA ACC |
| PHSRN3 | Forward | GTG CCG CAC TCA AGG AAT TCA ATA ACG GGT CCT GCA ACT TGA GGT AGT |
|  | Reverse | ATT CCT TGA GTG CGG CAC TCT ATC CTC AGA GGT CCA AAC CAA ACC AGA |
| DGEA1 | Forward | TGG ACC TCT GAC GGC GAG GCC GGT CCT GCA ACT TGA GGT |
|  | Reverse | AGC AGG ACC GGC CTC GCC GTC AGA GGT CCA AAC CAA ACC |
| P15 | Forward | AGC GGC AGA GGC GAC AGC GGC GCC GGT CCT GCA ACT TGA GGT AGT |
|  | Reverse | GCT GTC GCC TCT GCC GCT GCC GGC AGA GGT CCA AAC CAA ACC AGA |

*RGD9 created using U3/RGD5 plasmid as template.

Interior Modification of TMV:

An interior surface of TMV was modified with fluorescein amine by using EDC/HOBT coupling reported by Schlick et al. The fluorescently labeled virus particles were purified by ultracentrifugation at 45,000 rpm for 1.5 hours (4° C.) (Beckman 70.2 Ti). The pellet was resuspended in 100 mM K phos buffer (pH 7) and used to determine surface coating density by measuring fluorescence on plate reader (ex/em 490/520 nm, Molecular Devices, SpectraMax M2e).

Mass Spectrometry Analysis of TMV Mutants:

An infected tobacco leaf of each TMV mutant was flash frozen in liquid nitrogen and ground up by using a mortar and pestle. The ground-up leaves were transferred to a 15 mL conical tube and re-suspended in 1-3 mL of 0.1 M K phos buffer (pH 7). The samples were spun down at 13,500×g (Sorvall RCS, SLA-1500 rotor) at 4° C. for 15 minutes, and the resulting supernatant (1 μL) was added to matrix solution (9 μL of saturated MS grade sinapic acid in 70% acetonitrile and 0.1% TFA). The sample mixture was then spotted on the MALDI plate, air-dried and analyzed using a Bruker Ultra-Flex I TOF/TOF mass spectrometer. Alternatively, purified virus solutions were mixed (1 μL of 0.1 mg/mL) with 9 μL of matrix solution (saturated sinapic acid in 70% acetonitrile, 0.1% TFA) and 1 μL of the mixture was spotted on the MALDI plate. The dried co-crystal was analyzed by MALDI-TOF MS using a customized setting (Bruker Daltonics Ultraflex I TOF/TOF). An average of 1000 shots was taken for each of the mutants and wild type virus solutions.

Cell Culture:

BHK cells were maintained in high glucose DMEM containing 4 mM L-glutamine, 1 mM sodium pyruvate and supplemented with 10% fetal bovine serum (FBS). CHO cells were cultured in DMEM/F12 media containing 4 mM L-glutamine, 1 mM sodium pyruvate, and supplemented 10% FBS. All cell culture reagents were purchased from HyClone.

Rat bone marrow stromal cells (rBMSCs) were harvested according to protocol approved by IACUC. Passages from 5-8 were used in the study. Rat BMSCs were isolated from the bone marrow of young adult male Wister rats (80 g, Harlan Sprague Dawley, Inc.). The procedures were performed in accordance with the guidelines for animal experimentation by the Institutional Animal Care and Use Committee, University of South Carolina. The isolated BMSCs were maintained and expanded for an additional passage in DMEM with 10% FBS. All cell culture reagents were purchased from HyClone. BMSCs were induced with DMEM/F12 without serum and had been supplemented with osteogenic factors (10 nM dexamethasone, 50 µg mL-1 ascorbic acid, 10 mM β-glycerophosphate) and growth factors (10 ng mL-1 recombinant human bFGF, 2.5 ng mL-1 recombinant human TGF-β, 10 ng mL-1 recombinant human EGF) and 1×ITS (insulin, transferrin, selenium). Dexamethasone, ascorbic acid and β-glycerophosphate were purchased from Sigma-Aldrich. Recombinant human bFGF and EGF were purchased from Stemgent, recombinant human TGF-β was purchased from Stem RD. 100×ITS stock was purchased from VWR/Mediatech. The cells were cultured to near 80% confluence and harvested by trypsinization. 4 mL of 0.25% Trypsin/EDTA (Hyclone) was used to dislodge the cells from the flasks and 3×105 cells were seeded in each well.

Adhesion Assay:

For centrifugal adhesion assay, high binding 96-well plates (Greiner Bio-one) were cleaned under UV light for 20 minutes at room temperature. Then, the plates were coated with virus solutions at concentrations of 1, 0.1 and 0.05 mg/mL-1 for 20 minutes at room temperature. The wells were rinsed three times with water, blocked with 1% BSA solution in PBS. The cells were pre-labelled with Calcein-AM (BD Bioscience) and each well was seeded with 104 BHK cells in serum-free DMEM. The cells were incubated at 37° C. for one hour, and imaged under an inverted phase contrast microscope with 10×lens (Olympus CKX41). The plate was read using a fluorimeter (Molecular Devices, SpectraMax M2e) with excitation wavelength at 490 nm, and emission cut-off at 520 nm. The wells were filled to the top with serum-free media and sealed with microplate film (Bio-Rad). The plate was inverted and spun in a swinging rotor (Beckman Coulter, SX4850) at specified RCF (g) ratings for 5 minutes at room temperature. The solution was carefully removed and fresh media (100 µl) was added. Afterwards, the fluorescence was measured and the post-spun intensities were normalized against pre-spin intensities to determine the fraction of adhered cells. The same adhesion assay was performed for CHO cells.

Adhesion Inhibition Assays:

The plates were prepared as described in adhesion assay. The cells were pre-labelled with Calcein AM for 30 minutes at 37° C. in humidified incubator. The cells were washed twice with lx DPBS and blocked with 10 µg of monoclonal antibodies (anti-α5, anti-α2, anti-αV, anti-β1, anti-β2 from BioLegend) per 105 cells in 1 mL of serum-free DMEM. The cells were incubated at 37° C. for 15 minutes, and then seeded on virus coated 96-well high binding plates (Greiner). The cells were incubated at 37° C. for an additional 30 minutes. The media was removed and replaced with new media prior to fluorescence measurements (Molecular Devices, SpectraMax M2e) with excitation wavelength at 490 nm, and emission cut-off at 515 nm. The fluorescence intensities were normalized against unblocked virus coated controls to determine the fraction of adhered cells in the presence of antibodies.

Cell Imaging and Analysis:

The cells were observed under a phase contrast microscope (Olympus CKX41). For each cells sample, the pre-spin, post 10 g spin, and post 30 g spin images were captured using Infinity2 (Lumenera). The plate was read using a fluorimeter (Molecular Devices, SpectraMax M2e) with excitation wavelength of 490 nm, and emission cutoff at 525 nm. The fluorescence data of the plate were measured for pre-spin, post 10 g spin, and post 30 g spin of BHKs cells. The post spin fluorescence values were normalized against the pre-spin fluorescence intensities. Then, the average values (n=6) and standard errors of mean were obtained for each TMV mutants. All experiments were conducted at least three separate times with multiple replicates. For CHO cells, the pre-spin, and post 10 g spin fluorescence data were obtained. The post 10 g spin data was normalized against the pre-spin data. The average values and standard errors of mean were also calculated for each TMV mutant. Significant values were based on p values<0.05 based on two-tailed equal variance Student t-tests. Layer by layer assembly and substrate characterization:

For tissue culture plasticware preparation, the 6-well plate was cleaned with $O_2$ plasma cleaner for 15 minutes. The first coating was for 30 minutes with poly(allylamine) hydrochloride (PAH, Mw~56,000, Aldrich) at a concentration of 1 mg/mL in 150 mM NaCl, filtered through 0.2 micron membrane (PALL). The wells were washed three times with $dH_2O$ (Millipore 18.2 MΩ) to remove unbound polyelectrolytes. Then each wells were incubated for 15 minutes with 1 mL of poly(styrene sulfonate) (PSS, Mw~70,000, Sigma) at a concentration of 2 mg/mL in 150 mM NaCl, filtered through 0.2 micron membrane (PALL). The polyelectrolyte solution was removed and wells were washed three times with water. The coating of polyelectrolytes, alternating between PAH and PSS, was repeated until a total of 7 layers were coated. The final layer was then coated with TMV or TMV-RGD1 (prepared at 1 mg/mL and filtered through 0.45 micron HT Tuffryn Membrane Syringe Filter, PALL life sciences). The final coating was washed with water three times and dried overnight. Prior to seeding the cells, the substrates were treated with UV irradiation for 15 minutes. All substrates were prepared within one day prior to seeding of cells.

For quartz crystal microbalance measurements, the silver electrodes were washed three times with $dH_2O$ (18.2 MΩ), dried under a stream of $N_2$. The dried electrodes were measured (9 MHz). The electrodes were then coated with PAH for 30 minutes at room temperature. The electrodes were washed with water and then dried under a stream of $N_2$. The dried electrodes were measured and the shift in oscillation frequencies was recorded. The coating, washing, and drying steps were repeated as each new layer of polyelectrolytes was added to the silver electrodes. All measurements were conducted in triplicates and in three separate experiments. The frequency shifts were converted to mass densities using Sauerbrey's equation:

$$\Delta f = \frac{-2\Delta m f_o^2}{A\sqrt{\rho_q \mu_q}}$$

Uncoated PEM and TMV coated PEM substrates were further characterized by water contact angle measurements. The piranha solution treated microscope coverslips (VWR 18 mm diameter, No. 2 thickness) measured approximately $10°\pm1°$ and the final PEM averaged $28°\pm5°$. Coating of the virus did not alter the water contact significantly, but could be well visualized by atomic force microscopy and mass density shift (QCM).

Cytochemical Staining and Immunofluorescence:

Batches of BMSCs culture on TMV coated substrates were terminated post 2 days of osteoinduction. Cells were fixed in 4% PFA in 1×D-PBS pH 7.4 at room temperature for 15 minutes. Each of the samples was then permeablized for 5 minutes with 1×D-PBS, 0.05% Triton X-100 and blocked with 3% bovine serum albumin (BSA, Rockland), 1×D-PBS for 1 hour at room temperature. After blocking, the cells were incubated overnight with primary antibodies targeting the osteo-specific marker osteocalcin. The secondary antibodies goat anti-rat FITC (VWR Scientific) were used for osteocalcin (BGLAP) at 1:100 dilutions in buffer at 4° C. TRITC-phalloidin (1:200 in 1×D-PBS) was used to stain filamentous actin. Nuclei were stained with DAPI (4, 6-di-amidino-2-phenylindole, 100 ng/ml). Images of the stained substrates were collected using Olympus IX81 fluorescent microscope with 60× oil lens (UPIanSAPO, NA=1.35). Negative control for staining included only secondary antibodies. After 2 days in osteogenic cultures, BMSCs seeded on hFN, PEM, TMV and TMV-RGD1 substrates were stained with Alizarin red calcium rich deposits. The cells were fixed in 4% paraformaldehyde at room temperature for 5 minutes, washed with water and then stained with 0.1% solution of Alizarin red (Sigma-Aldrich) pH 4.1-4.5 for 60 minutes at room temperature. Since the reaction was highly light sensitive, the substrates were wrapped in aluminum foil during the entire time of incubation.

ELISA and Western Blot:

Cells were fixed in 4% paraformaldehyde/1×D-PBS for 5 minutes at room temperature. The cells were washed and blocked with 1% BSA/1×D-PBS/0.05% Triton X-100 for 30 minutes. The primary antibody against BMP-2 was incubated in three wells overnight at 4 degrees celsius at a dilution of 1:100. The samples were rinsed with PBS, 0.05% Triton X-100, three times and the secondary antibody (anti-mouse Goat polyclonal with HRP conjugate) was incubated for 1 hour at room temperature. The samples were washed three times and incubated with TMB solution for 30 minutes and the reaction was stopped with concentrated sulfuric acid. The solution was read with a UV-Vis spectrophotometer at 450 nm.

For western blots, cells were cultured on 6-well plates. The media was aspirated and the cells were directly lysed by adding 100 µl of Laemmeli buffer (Bio-rad) containing 2-mercaptoethanol and protease inhibitor, PMSF (1 µg/mL). The lysate was scrapped and transferred to a clean microfuge tube and heated at 95° C. for 15 minutes, then immediately cooled on ice prior to loading on a 12% SDS-PAGE. The gel was run for 60 minutes at 200 V in a Mini-Protean 3 Gel electrophoresis rig (Bio-rad). The gel was transferred to PVDF membrane then block with 2% BSA in PBS with 0.05% Triton X-100 (PBS-T) for one hour at room temperature. The primary antibody (total FAK or pY397 FAK, Cell Signaling Technology) was added to the block solution at 1:1000 dilution and incubated overnight. The membrane was washed three times with PBS-T, then probed with secondary antibody (anti-rabbit goat IgG with HRP conjugate) at 1:5000 dilution for one hour at room temperature in 2% BSA in PBS-T. The membrane was washed three times, then imaged with enhanced chemiluminesence kit (Pierce ECL) according to manufacturer's protocol. The resulting blots were scanned and intensity plots were measured by ImageJ. The average of three separate images were used. The intensity of pY397 FAK was normalized to total FAK for all samples and the normalized intensities were plotted relative to cell lysates from hFN substrates.

Detailed Protocols for Purification, Handling and Use of Tobacco Mosaic Virus and Mutant Variants are incorporated by reference herein from U.S. Provisional Patent Application No. 61/795,736 filed on Oct. 24, 2012 of Wang, et al.:

Infecting plants by mechanical abrasion using purified virus stock solution: Method:

1. Infections occur best when the plants are infected near its dark cycle. The artificial sunlight may reduce infections.
2. Spray water on the leaves using a mist/spray
3. Sprinkle carborundum (silicon carbide) on the leaves. Wear a mask to prevent accidental inhalation. Carborundum is an abrasive material.
4. Dilute the virus stock solution to 0.05 mg/mL in buffer solution. Typically use 1 mg in 20 mL of buffer for one tray of plants (24 containers).
5. Cut cheesecloth to 4" square piece and soak the cheesecloth in the virus solution.
6. Wrap the cheesecloth around the index finger and gently rub the cheesecloth along the tobacco leaves. The presence of carborundum on the leaves will introduce micro-abrasions and the virus infection will occur once it penetrates through the upper layer of the leaf.
7. Repeat steps 6 and 7 for every 3-4 plants.
8. Residual carborundum should be washed off by watering the plants the next morning.

Infecting Plants by Mechanical Abrasion using Genetic Material:

Method:

1. Infections occur best when the plants are infected near its dark cycle. The artificial sunlight may reduce infections.
2. Spray water on the leaves using a mist/spray (10 microgram of genetic material is sufficient for 2 leaves from one plant).
3. Sprinkle carborundum (silicon carbide) on the leaves. Wear a mask to prevent accidental inhalation. CAUTION: Carborundum is an abrasive material.
4. Cut cheesecloth to 4" square piece and gently wipe the cheesecloth along the tobacco leaves. The presence of carborundum on the leaves will introduce micro-abrasions.
5. Pipette droplets of the genetic material around the leaves.

Post-infection Plant Monitoring:

NOTE: Wild type TMV infected plants exhibit dark green patches around the leaves.

10 to 14 days post-infection, a leaf is cut. The leaf should weigh 0.5-2 g and be one of the two primary leaves used for infection. The cut leaf is flash frozen in liquid nitrogen and ground to fine powder using a mortar and pestle. A portion of the leaf is used for protein analysis by MALDI-TOF MS and another portion for mRNA extraction and sequencing.

Viral Coat Protein Analysis by MALDI-TOF MS:

500 mg of leaf material is transferred to a 2 mL eppendorf tube, and 1 mL of chilled buffer (100 mM potassium phosphate pH 7) is added to the tube. The mixture is vortexed for 30 seconds, then centrifuged at 16,000×g for 10 minutes at 4°C. The supernatant is transferred to a new eppendorf tube. 2 µl of the supernatant is mixed with 8 µl of matrix solution (saturated solution of sinapic acid in 70% acetonitrile, 0.1% trifluoroacetic acid). The mixture is vortexed, centrifuged and 2 ul is spotted on an aluminum MALDI plate. Sample is analyzed using Bruker Daltonics MALDI-TOF MS. Expected m/z is 17,535 for singly charged wild type TMV coat protein, which matches M+H+. A peak at m/z 8,768 corresponds to a doubly charge. A peak around m/z of 10,477 is typically observed for plant lysate samples. For TMV-RGD1 mutant, the expected peak is 18,151. Save plant sap in −20°C freezer for later use.

The mass of the viral coat protein is calculated by adding the mass of an acetyl group to the N-terminal amino acid (serine). The first methionine is cleaved during post-translational processing in plant hosts.

Viral Coat Protein Gene Sequencing:

Total plant mRNA is isolated using Qiagen plant RNA extraction kit and used for cDNA synthesis using the specified primer.

```
cDNA primer/Reverse:
                                    (SEQ ID NO: 51)
5' CGT GCC TGC GGA TGT ATA TGA AC 3'
```

The cDNA is used as a template for PCR amplification of the virus coat protein gene. The two specific primers used are:

```
CP Sequencing/forward:
                                    (SEQ ID NO: 52)
5' CGT TAT CGT ACG CAC CAC GTG TG 3' cDNA primer/Reverse:
                                    (SEQ ID NO: 51)
5' CGT GCC TGC GGA TGT ATA TGA AC 3'
```

The PCR product should be 756 bp for wild type TMV. The PCR product is isolated and sequenced using the CP sequencing/forward primer.

Propagating the Mutant Virus from Single Plant Host:
(Only Necessary if Genetic Material was Used to Infect One Plant)

1. After verifying the infection has occurred in the original plant, the frozen plant supernatant/sap saved from previous method (MALDI-TOF MS) can be used to infect 20 plants (2 leaves per plant) by diluting 1 mL of the sap in 20 mL of buffer and following the method under infections by mechanical abrasions with purified virus stock.

2. If the plant sap is not available, a fresh cut leaf can be flash frozen in liquid nitrogen, ground to fine powder using mortar and pestle. For every 1 g of plant material, add 2 mL of pre-chilled buffer. Dilute the supernatant with buffer to 20 mL final volume and use to infect 20 plants following the methods under mechanical abrasions with purified virus stock.

Tobacco Mosaic Virus and Mutant Variant Purification Protocols (Chloroform/Butanol Extraction):

EQUIPMENT: Standard Kitchen brand blender (4 L) or a Laboratory grade tissue homogenizer; Sorvall RC-5C plus centrifuge and rotor models SLA -1500 and SLC-4000; 250 mL and 1 liter Nalgene centrifuge bottles (withstand up to 20,000×RCF); Beckman Ultracentrifuge, 50.2 Ti rotor and screw cap tubes MATERIALS: Organic solvents—Chloroform and n-butanol; Large Kimwipes; Cheesecloth; Beakers (1 and 2 liters); Funnels; 100 mM and 10 mM potassium phosphate buffer (pH 7); Polyethylene Glycol 8,000; β-mercaptoethanol; PMSF, aprotinin, leupeptin (for mutants with long inserts)

1. All buffers are 0.1 M potassium phosphate pH 7 unless specified, and should be pre-chilled prior to use. For TMV1Cys mutant, additional β-mercaptoethanol is used (0.3 to 0.5% of volume). For mutant strains with long peptide inserts (>4 amino acids), add plant protease inhibitors.

2. Check the bag of leaves used for the purification in the logbook.

3. The frozen bag of leaves is manually pulverized prior to transferring to a 4 L blender (Oster or any kitchen brand is used to further homogenize the plants; however a laboratory grade tissue homogenizer can be used).

4. For every 100 g of plant material, add 300 mL of pre-chilled buffer and 0.1% β-ME (vol % of buffer).

5. Slowly start the blender from lowest setting and gradually increase to highest setting to homogenize the leaves. Leave the blender on for 5 minutes.

6. Place a large beaker (1 L for 100 g of leaves, or 2 L for 200 g of leaves) on ice. Place a clean funnel on top of the beaker.

7. Place two layers of cheesecloth on top of a funnel and collect the flow-through in the large beaker.

8. Transfer the flow-through to Nalgene centrifuge tubes (250 mL tube for SLA-1500 rotor used in Sorvall RC-5C plus floor centrifuge).

9. Weigh out the tubes and balance in pairs prior to centrifuging at 10,500 RPM for 20 minutes at 4□C.

10. Prepare another beaker (same volume as step 5) on ice and a funnel on top of the beaker.

11. Place one layer of Kim-wipe on top of the funnel.

12. The clarified supernatant is filtered through one layer of Kim-wipe.

13. Add equal volume of n-butyl alcohol and chloroform (organic solvent) to the clarified plant supernatant at volume ratio of 1:1:2, respectively. (Make sure mix n-butyl alcohol and chloroform first; always pour n-butyl alcohol first so the solutions can be mixed before used; always pour those solutions under the fume hood). Stir the mixture on ice for 30 min.

14. Pour the solution into Nalgene centrifuge tubes and balance the tubes. Centrifuge at 4□C, 10,500 RPM, for 10 min in SLA-1500 rotor (Sorvall RC-5C plus)

15. For large volumes (>1 L), use the SLC-4000 rotor and centrifuge at 6,000 RPM for 20 minutes at 4□C.

16. Transfer the aqueous layer to a clean beaker.

17. Add PEG 8000 to 8% wt/vol and 0.2 M NaCl. (Ex: 8% wt/vol of PEG 8000 for 450 mL final volume requires=0.08*450 mL=36 g and 0.2 M NaCl*0.450 L*59 g/mol=5.31 g).

18. Stir the mixture on ice (or at 4° C.) for 1 hour.

19. Transfer to 250 mL Nalgene centrifuge bottles, and pellet the viral particles at 4° C., 13,500 RPM, for 20 minutes using SLA-1500 rotor in RC-5C plus Sorvall centrifuge.

20. Discard the liquid, and resuspend the pellet with 10 mM buffer pH 7. The pellet contains purified virus particles with PEG and trace contaminants.

21. Transfer the resuspension to a 50 mL conical vial and centrifuge at 9,500 RPM for 15 min at 4° C. using SLA-1500 rotor. NOTE: The conical tubes should resist up to 13,000 RCF.

22. Transfer the supernatant to ultracentrifuge tubes (For 50.2 Ti rotor use Beckman Centrifuge Bottles, Polycarbonate, Catalog Number 355654 with cap assemblies, 26.3 mL volume; for 70.1 Ti rotor, use polycarbonate centrifuge bottles with cap assemblies, catalog number 355603, 10.4 mL volume capacity) NOTE: Adhere to the vendor's instructions regarding solvent compatibilities and sterilization strategies.

23. Fill the tube up to about 2-3 cm from the top. Then, layer the sucrose cushion (30% sucrose in 10 mM buffer) at the bottom of the tube. Balance the tubes in pairs 24. Centrifuge with the 50.2 Ti rotor at 42,000 RPM for 2.5 hours at 4°C. CAUTION: Check the O rings in the rotor and the rotor lid before using it. Grease the O-rings with vacuum grease.

25. Resuspend the pellet in 100 mM buffer overnight at 4°C.

26. Transfer the solution to conical vials and centrifuge at 4°C, at 9500 RPM, for 15 minutes using Sorvall RC-5C plus centrifuge.

27. To determine the concentration, measure the UV (260 nm, 280 nm). TMV has a typical 260/280 ratio of 1.2 and 1 mg/mL solution has absorbance value of 3 at 260 nm.

28. Transfer the supernatant to a clean tube and store the purified virus solution in aliquots at −20°C or −80°C for long term storage. Do NOT flash freeze in liquid nitrogen.

Alternative Virus Purification Methods:
Tobacco Mosaic Virus and Mutant Variant Purification Protocols (Butanol ONLY):

EQUIPMENT: Standard Kitchen brand blender (4 L) or a Laboratory grade tissue homogenizer; Sorvall RC-5C plus centrifuge and rotor models SLA -1500 and SLC-4000; 250 mL and 1 liter Nalgene centrifuge bottles (withstand up to 20,000×RCF); Beckman Ultracentrifuge, 50.2 Ti rotor and screw cap tubes MATERIALS: Organic solvents—n-butanol; Large Kim-wipes; Cheesecloth; Beakers (1 and 2 liters); Funnels; 100 mM and 10 mM potassium phosphate buffer (pH 7); Polyethylene Glycol 8,000; β-mercaptoethanol; Triton X-100

1. All buffers are 0.1 M potassium phosphate pH 7 unless specified, and should be pre-chilled prior to use. For TMV1Cys mutant, additional β-mercaptoethanol is used (0.3 to 0.5% of volume).

2. Check the bag of leaves used for the purification in the logbook.

3. The frozen bag of leaves is manually pulverized prior to transferring to a 4 L blender (Oster or any kitchen brand is used to further homogenize the plants; however a laboratory grade tissue homogenizer can be used).

4. For every 100 g of plant material, add 300 mL of pre-chilled buffer and 0.2% β-ME (vol % of buffer).

5. Slowly start the blender from lowest setting and gradually increase to highest setting to homogenize the leaves. Leave the blender on for 5 minutes.

6. Place a large beaker (1 L for 100 g of leaves, or 2 L for 200 g of leaves) on ice. Place a clean funnel on top of the beaker.

7. Place two layers of cheesecloth on top of a funnel and collect the flow-through in the large beaker.

8. Add 8 mL of n-butanol for 100 mL of plant sap.

9. Transfer to Nalgene centrifuge tubes (250 mL tube for SLA-1500 rotor used in Sorvall RC-5C plus floor centrifuge).

10. Weigh out the tubes and balance in pairs prior to centrifuging the plant debris at 12,000 RPM for 15 minutes at 4°C.

11. Prepare another beaker (same volume as step 5) on ice and a funnel on top of the beaker.

12. Place one layer of Kim-wipe on top of the funnel.

13. The clarified supernatant is filtered through one layer of Kim-wipe.

14. Add 4 g of PEG 8000 and 4 g of NaCl for 100 mL of supernatant.

15. Stir the mixture on ice for ½ hour.

16. Transfer to 250 mL Nalgene centrifuge bottles, and pellet the viral particles at 4°C., 12000 RPM, for 20 minutes using SLA-1500 rotor in RC-5C plus Sorvall centrifuge.

17. Discard the liquid, and resuspend the pellet with 10 mM buffer pH 7, 1% Triton X-100.

18. Transfer the resuspension to a 50 mL conical vial and centrifuge at 9,500 RPM for 15 min at 4°C using SLA-1500 rotor. NOTE: The conical tubes should resist up to 13,000 RCF.

19. Transfer the supernatant to ultracentrifuge tubes (For 50.2 Ti rotor use Beckman Centrifuge Bottles, Polycarbonate, Catalog Number 355654 with cap assemblies, 26.3 mL volume; for 70.1 Ti rotor, use polycarbonate centrifuge bottles with cap assemblies, catalog number 355603, 10.4 mL volume capacity) NOTE: Adhere to the vendor's instructions regarding solvent compatibilities and sterilization strategies.

20. Fill the tube up to about 2-3 cm from the top. Then, layer the sucrose cushion (30% sucrose in 10 mM buffer) at the bottom of the tube. Balance the tubes in pairs 21. Centrifuge with the 50.2 Ti rotor at 42,000 RPM for 2.5 hours at 4°C. CAUTION: Check the O rings in the rotor and the rotor lid before using it. Grease the O-rings with vacuum grease.

22. Resuspend the pellet in 100 mM buffer overnight at 4°C.

23. Transfer the solution to conical vials and centrifuge at 4°C, at 9500 RPM, for 15 minutes using Sorvall RC-5C plus centrifuge.

24. To determine the concentration, measure the UV (260 nm, 280 nm). TMV has a typical 260/280 ratio of 1.2 and 1 mg/mL solution has absorbance value of 3 at 260 nm.

25. Transfer the supernatant to a clean tube and store the purified virus solution in aliquots at −20°C or −80°C for long term storage. Do NOT flash freeze in liquid nitrogen.

NOTE: Use of Triton X-100 will increase yield but can affect downstream use of the viral particles. If the trace amount of the detergent needs to be removed, additional ultracentrifugation step is required.

Coating Virus on Surfaces for Cell Cultures: Layer by layer coating on plasticwares:

EQUIPMENT: Harrick's Plasma Cleaner with $O_2$ regulator; Bio-safety cabinet for aseptic operations MATERIALS: Polyallyamine Hydrochloride (Alfa Aesar, Cat. No. 43092)—1 mg/mL in 18.2 MΩ MilliQ dd$H_2$O; Poly(sodium 4-styrenesulfonate) (Aldrich, Cat. No. 527483)—2 mg/mL diluted in 18.2 MΩ MilliQ dd$H_2$O; Tissue culturewares (Corning, Bio-Greiner One have been tested from 6-well plates to 96-well plates); 0.45 micron syringe filters PALL HT Tuffryn low protein binding membrane; Syringe; Sterile conical tubes; 10 mM potassium phosphate buffer pH 7; Sterile water solution 1. Tissue culture plasticware is cleaned with oxygen plasma for 15 minutes (Harrick's plasma cleaner). Oxygen plasma is a white pink glow. Purple glow note air plasma, and oxidation will be sub-optimal. Plasma treatment should be for 30 minutes for 96-well plates.

2. Substrates are immediately coated with PAH (1 mg/mL, polyallylamine chloride) solution for 15 minutes. The solution should be sufficient to cover the entire well (2 mL per well for 6-well plates, 1 mL per well for 12-well plates, 0.5 mL for 24-well plates and 0.1 mL per well for 96-well plates).

3. The polymer solution is removed and the surfaces are washed with water (18.2 MΩ MilliQ ddH2O) three times, and then coated with PSS (2 mg/mL, polystyrene sulfonate) solution for 15 minutes.

4. The polymer is removed and washed three times with water. Steps 2-4 are repeated until 5 total layers of polymers are coated on the surface (PAH/PSS/PAH/PSS/PAH). The final top layer should be PAH.

5. The polymer coating is UV-irradiated for 15 minutes, then air-dried in the sterile hood overnight. CAUTION: Failure to dry the polymer coating will result in loose coating which will peel off during cell culture.

6. Filter sterilize the virus solution with a syringe filter (PALL HT Tuffryn low protein binding membrane 0.45 micron) and verify the virus concentration by measuring UV-Vis absorbance at 260 and 280 wavelengths. Concentration should be adjusted to 0.1 mg/mL in 10 mM potassium phosphate buffer (pH 7).

7. Pipette the virus solution to the wells and incubate for 20 minutes at room temperature.

8. Remove the virus solution and wash three times with water

9. UV-irradiate for 15 minutes and let the substrate air-dry overnight.

NOTE: The final substrate as dried film is very stable at room temperature as long as contaminants are avoided by keeping a lid or a tight seal around the plates. For coating the glass coverslips or other silica based substrates, the glass is treated with piranha solution (70% sulfuric acid, 30% hydrogen peroxide) for 10-20 minutes. After cleaning glass with piranha solution, rinse with copious amounts of water and proceed with polymer coatings (steps 2-4).

Preparing the Piranha Solution

Chemicals: Sulfuric Acid (H2SO4 96%), Hydrogen Peroxide (H2O2 30%).

Note: These percentages are the dilutions as they arrive in the bottles from the chemical supplier. Just use the solution straight out of the bottle. Single polymer layer coating on plasticwares:

EQUIPMENT: Harrick's Plasma Cleaner with O2 regulator; Bio-safety cabinet for aseptic operations MATERIALS: Polyallyamine Hydrochloride (Alfa Aesar, Cat. No. 43092)—1 mg/mL in 18.2 MΩ MilliQ ddH2O with pH adjusted to 5 with 1 M NaOH; Tissue culturewares (Corning, Bio-Greiner One have been tested from 6-well plates to 96-well plates); 0.45 micron syringe filters PALL HT Tuffryn low protein binding membrane; Syringe; Sterile conical tubes; 1 M NaOH; 10 mM potassium phosphate buffer pH 5; Sterile water solution 1. Tissue culture plasticware is cleaned with oxygen plasma for 15 minutes (Harrick's plasma cleaner). Oxygen plasma is a white pink glow. Purple glow note air plasma, and oxidation will be sub-optimal. Plasma treatment should be for 30 minutes for 96-well plates.

2. Prepare PAH (1 mg/mL, polyallylamine chloride) solution by dissolving the polymer in water (18.2 MΩ MilliQ ddH2O) and adjust to pH 5 with 1 M NaOH.

3. The polymer solution is used to coat the surfaces for 15 minutes.

4. The solution is removed and the surfaces are washed with water (18.2 MΩ MilliQ ddH2O) three times.

5. The polymer coating is UV-irradiated for 15 minutes, then air-dried in the sterile hood overnight. CAUTION: Failure to dry the polymer coating will prevent virus from binding to the substrate.

6. Filter sterilize the virus solution with a syringe filter (PALL HT Tuffryn low protein binding membrane 0.45 micron) and verify the virus concentration by measuring UV-Vis absorbance at 260 and 280 wavelengths. Concentration should be adjusted to 1 mg/mL in 10 mM potassium phosphate buffer (pH 5).

7. Pipette the virus solution to the wells and incubate for 20 minutes at room temperature.

8. Remove the virus solution and wash three times with water

9. UV-irradiate for 15 minutes and let the substrate air-dry overnight.

NOTE: The final substrate as dried film is very stable at room temperature as long as contaminants are avoided by keeping a lid or a tight seal around the plates. Glass substrates can also be coated by cleaning with piranha solution and rinsing with large amounts of water.

Direct Virus Coating on High Binding Plasticwares:

EQUIPMENT: Bio-safety Cabinet for Aseptic Operations

MATERIALS: Tissue culturewares (high binding 96-well plates from Corning, or Bio-Greiner One); 0.45 micron syringe filters PALL HT Tuffryn low protein binding membrane; Syringe; Sterile conical tubes; Sterile water solution 1. Virus solution is directly pipette to the high binding plates at concentration of 0.1 mg/mL, 100 mM potassium phosphate buffer pH 5.

2. Remove the virus solution and wash three times with water

3. UV-irradiate for 15 minutes and let the substrate air-dry overnight.

Follow-up Quality Control Assessments on Virus Coated Substrates:

EQUIPMENT: Veeco Atomic Force Microscope; Water contact angle measurement using static sessile drop method with goniometer (VCA Optima contact angle)

PROCEDURE:

1. Samples were cut out from the plasticware with a box cutter knife. Tapping-mode atomic force microscope (AFM) images were obtained at ambient conditions using Nanoscope IIIA MultiMode AFM (Veeco). Si tips with a resonance frequency of approximately 300 kHz, a spring constant of about 40 N m-1, and a scan rate of 0.75 Hz were used.

2. Three different substrates are cut out and measured with static sessile drop method with goniometer (VCA Optima contact angle). Two measurements per drop and three different areas on each substrate are recorded (total measurements equals 6 per substrate).

Bone Marrow Derived Mesenchymal Stem Cell Cultures on Virus-coated Surfaces:

MATERIALS: DMEM/F12 (HyClone or Mediatech) without phenol red indicator; 10×ITS (Mediatech); Basic FGF (Stemgent)—100 μg/mL stock solution in 5 μl aliquots and stored at −80° C.; TGF-beta (Stemgent)~100 μg/mL stock solution in 2 μl aliquots and stored at −80° C. EGF (Stemgent)—100 μg/mL stock solution in 5 μl aliquots and stored at −80° C.; Trypsin/EDTA solution (HyClone) ~0.25%; 1×D-PBS sterile; Sodium beta glycerophosphate (Sigma); Ascorbic 2-phosphate (Sigma)—Prepare a 25 g/mL stock solution in sterile water; Dexamethasone (Sigma)—prepared by dissolving 1 mg in 1 mL absolute ethanol and adding 49 mL of sterile media.

Procedure:

1. To prepare 150 mL of serum-free osteogenic media, add 0.46 g of sodium beta glycerophosphate, 0.3 mL of 25 g/mL ascorbic 2-phosphate stock solution and 30 μl of dexamethasone (20 μg/mL stock solution) to DMEM/F12.

2. Transfer 40 mL of the media to conical vial and add 0.4 mL of 10×ITS (Mediatech)

3. Add 1 μl of 100 μg/mL TGF-beta, 4 ul of 100 μg/mL bFGF, and 100 μg/mL EGF.

4. The media with growth factors can be used for 3-7 days.

5. Bone-derived mesenchymal stem cells are cultured to near confluence in standard media (DMEM/F12 supplemented with 10% FBS), then harvested by trypsinization.

6. The cells are centrifuged at 300 rpm for 5 minutes and washed twice in pre-warmed serum-free media (DMEM/F12).

7. The cells are centrifuged and resuspended in osteogenic serum-free medium at cell density of 100,000 per mL.

8. For controls, use human fibronectin (hFN, BD Biosciences) coatings. Cells will attach and spread on hFN coated substrates.

Synthesis of Virus-Incorporated Porous Alginate Hydrogels and Cell Culturing

The synthesis of gas template solid foam was based on the methodology reported by Barbetta et al.20 Briefly, 5% w/v low viscosity sodium-alginate (Protanal® LF 10/60 FT, 30-60 mPas for 1%, kindly provided by FMC Biopolymer UK Ltd.), was dissolved in 2% w/v sodium bicarbonate (NaHCO3) and 4% w/v pluronic F108 solution. Molar equivalent of citric acid with respect to NaHCO3 was added to the mixture while stirring. Stirring was continued for 15 min to allow $CO_2$ to fully develop. Afterward, the foamy alginate solution was flash frozen in liquid nitrogen and freeze-dried. The resulting solid foam was soaked in 2 M of $CaCl_2$ for 24 h to induce the formation of the calcium-based physical gel and then dialyzed against large volume of 0.1 M $CaCl_2$. Finally, the solid foam was freeze-dried, resulting in porous alginate hydrogel (PAH). For the TMV modified PAH (TMV-PAH), or mutant TMV-RGD1 modified PAH (RGD-PAH), 0.1% w/v of virus was added to the solution 10 min after adding citric acid. The mixture was stirred for another 5 min.

TMV-PAH was de-crosslinked and dissolved in 0.5 M EDTA, and the solution was analyzed under transmission electron microscopy (TEM) (Hitachi H-8000 microscope) on 300 mesh copper grids coated with carbon and stained with 2% uranyl acetate. The absorbance at 260 nm was measured by UV-Vis spectroscopy to confirm the concentration of TMV in de-crosslinked alginate solution.

Lyophilized PAH, TMV-PAH, and RGD-PAH were cut to 3×3×2 mm3 cubes. In each set of experiment, six hydrogels per type of sample were used for these studies. Hydrogels were sterilized in 70% ethanol for 15 min, ethanol was drained on sterile filter paper and the hydrogels were further sterilized under UV-light for 60 min in laminar airflow hood. Hydrogels were then saturated in complete primary media at 37° C. for 60 min, blotted excess media with sterile filter paper, and placed in 12-well non-adhesive plate (6 hydrogels in each well). Rat BMSCs were harvested from 80% confluent culture flask using 0.25% trypsin/EDTA for 5 min and counted the number of cells and re-suspended in complete primary media. 1.4×103 BMSCs were seeded per one volume of hydrogel. Rat BMSCs loaded hydrogels were initially incubated with 200 μL of complete primary media in each well to prevent hydrogels from drying out. After 6 h of an initial incubation, hydrogels were completely submersed in 1 mL of complete primary media in each well. The hydrogels seeded with rBMSCs were cultured at 37° C. and 5% $CO_2$.

Attachment percentages were determined for different types of hydrogels on day 1 after cell seeding by counting floating cells in each well with a hematocytometer. Three separate experiments were carried out in this study.

Cell viability. Attachment percentage =

$$\frac{\text{total seeding cell number} - \text{floating cell number}}{\text{total seeding cell number}}$$

CellTiter-Blue® (CTB) cell viability assay (Promega) after day 8 and day 14 of culture was performed for each type of hydrogel. The culture media in each well was replaced by pre-warmed with 1 mL of media containing 10% CTB and incubated for 1 h at 37° C. and 5% $CO_2$. The media containing CTB was used without cells as negative controls. The measurement of the CTB product was taken at two time points. First, to detect the cells that attached to the outer surface of hydrogel, the solution was collected and replaced with 1 mL of culture media. The incubation was continued for another 2 h to allow diffusion of the fluorescent product from the inner part of hydrogel. After 2-hour incubation, the media solution was collected again and replaced with 1 mL of culture media in each well to continue cell culture. The 1:1 mixture of solution from first collection and second collection was measured fluorescence intensity at 560/590 nm (Ex/Em) using SpectraMax M2 Multi-Mode microplate reader (Molecular Devices). Also, three separate experiments were conducted with each type of sample comprised of 6 hydrogels.

Osteogenic Culture:

After 1 day of cell seeding, complete primary media was replaced by osteogenic media consisting of DMEM supplemented with 10% FBS, 10 mM sodium β-glycerol phosphate, I-ascorbic acid (50 μg/mL), 10-2 μM dexamethasone, penicillin (100 units/mL), streptomycin (100 μg/mL), and amphotericin B (1 μg/mL). The osteogenic media was changed every 2 days. The culture was incubated at 37° C. and 5% $CO_2$.

Alkaline Phosphatase (ALP) and Mineralization Assays:

Alkaline phosphatase (ALP) activity was determined using pNPP (p-nitrophenyl phosphate) assay (Sigma Diagnostics). After 3, 7 and 14 days, the hydrogels with cells were pre-washed with TBS then incubated with pNPP solution at room temperature for 2.5 h. Absorbance was read using a M2 SpectraMax plate reader at 405 nm indicating ALP activity levels. The enzyme activity was calculated from Beer-Lambert law as follow, $$\text{Enzyme activity}(\mu\text{moles/min}/\mu g) = \frac{V(\mu l) \times OD405 \text{ nm}(\text{cm}^{-1})}{\varepsilon \times \text{incubation time (min)} \times \text{enzyme}(\mu g)}$$

where ε is the molar extinction coefficient (M-1×cm-1). For p-nitrophenol, ε=1.78×104 M-1×cm-1. OD405 nm (cm-1) is the absorbance at 405 nm divided by the light-path length (cm). V is the final assay volume (100 μL).

Alizarin Red S (ARS) staining for $Ca^{2+}$ was performed on day 14 cultures. The hydrogels with cells were washed 3 times with TBS and fixed in 10% buffered formalin overnight and sliced into 1 mm thick. The sections were then stained with 0.1% solution of ARS (Sigma-Aldrich) pH 4.1-4.5 for 30 min, washed with 1:1 xylene:acetone solution and placed with toluene mounting solution on glass slides. Control experiments without cells were conducted for PAH, TMV-PAH, and RGD-PAH.

Calcium concentrations were quantified using Varian 720-ES ICP-OES (Inductively Coupled Plasma—Optical Emission Spectrometer) elemental analysis. Standards were created using 0-0.4 mg/L calcium standard solutions. PAH, TMV-PAH and RGD-PAH with similar size and weight were seeded with BMSCs and cultured with osteogenic supplement media until day 6. Samples were washed with sterile Milli-Q water and completely lysed with dissolving solution (0.1% HNO3, 0.01% TritonX-100, in 100 mM sodium citrate). The dissolved samples were diluted to fit the range of the standard curve. Approximately 4 mL of each diluted sample was fed into the instrument per run. The experiment was performed in triplicates. Control experiments without cells were also performed for PAH, TMV-PAH, and RGD-PAH in the same manner. Immunostaining:

Immunostaining was performed to observe the presence of osteocalcin. rBMSCs culture in PAH, TMV-PAH, and RGD-PAH were terminated after culturing 10 days for PAH and 13 days for TMV-PAH and RGD-PAH hydrogels in osteogenic media. Hydrogels were washed three times with 100 mM cacodylated buffer and then fixed in 2.5% glutaraldehyde in cacodylated buffer overnight. The fixed samples were then permeablized for 15 min in TBST (0.05% Tween20) and blocked in 2% w/v bovine serum albumin (BSA, Sigma-Aldrich) in TBS for 20 min with gentle agitation at room temperature. After blocking, the hydrogels were incubated for 2 h with primary antibody targeting the osteospecific gene osteocalcin (Santa Cruz Biotechnology). Secondary antibody detection Alexa Fluor® 546 (Molecular Probes, Invitrogen) was used for osteocalcin at 1:100 dilutions in blocking buffer for 1 hat room temperature. In the end, the hydrogels were washed with TBS and counterstained with DAPI (nuclear staining) and FITC-Phalloidin (actin staining). Images of the stained samples were obtained using Olympus IX81 with DSU confocal mode under 20×oil lens (NA=0.85). Exposure times were kept constant for all samples (500 ms for DAPI and phalloidin, 1000 ms for osteocalcin).

SUMMARY

The viruses are well-tolerated as underlying substrates by various mammalian cells (murine and human cells), and have surprisingly exhibited some tremendous potential in guiding cells for outgrowth and even for osteogenic differentiation. Previous studies had primarily focused on the role of native TMV U1 strain and its chemically modified variants to promote cell attachment and direct cell outgrowth. Other groups have demonstrated the possibility of inserting cell binding motifs to the coat proteins of bacteriophages to promote cell differentiation, redirect the natural targeting motifs towards specific cell types, or repackage the inner contents with imaging agents or therapeutic agents. For this study, longer cell binding peptide sequences were inserted near the carboxy end of the viral coat protein (up to 15 amino acids), which is not permissible for the major coat protein of M13 bacteriophages. Two of the RGD mutant containing different flanking sequences, a 12-mer fibronectin synergy site, and two collagen peptide sequence variants were successfully expressed on the TMV coat protein. A systematic screening protocol with the centrifugal adhesion assay was adapted to determine the biological functionality of the peptide inserts on the viral particles. The virus coating density has been reduced significantly and only a minimal amount of the virus (10 µg per well) was needed whereas our previous studies with mesenchymal stem cells required milligram quantities per coverslip. The virus-based substrates can be screened by a simple and quantifiable process to aid many of the future projects for determining receptor specificity, ligand concentration effects, and competitive assays.

The results indicate that native TMV capsids provide little to no cell binding specificity under the reported experimental conditions. Cells attached to the substrates coated with virus mutants containing RGD peptide sequences near the carboxy terminus of the viral coat protein. However of the 9 different mutants designed, only two mutants exhibited systemic infections (Supplementary Table 1). The BHK cells seeded on TMV-RGD1 and RGD7 had similar attachment profiles, but promoted stronger attachment for CHO cells. There are several differences between RGD1 and RGD7 insertions. RGD1 is based on a 7-mer insert that extends from the carboxy terminus of the coat protein, whereas RGD7 insert a 12-mer sequence that sits between residues serine 155 and glycine 156. The difference in attachment strengths could be attributed to the different flanking sequences, which may provide different tertiary conformation of RGD peptide for improved binding for RGD1. There is also one additional residue for the RGD1 mutant (-S155GPATG-RGD- (SEQ ID NO: 53)) whereas RGD7 amino acid sequence has the binding sequence (-S155AVTG-RGD- (SEQ ID NO: 54)). A single residue extension and the different flanking sequence (a bend introduced by proline in RGD1 whereas RGD7 has mostly small side chain amino acids) could provide greater surface exposure and receptor binding potential. Both possibilities are both logical explanations for the adhesion strength differences. The two cell lines tested showed weaker attachment to the surfaces coated with the TMV mutant that contains the fibronectin synergy site, PHSRN (SEQ ID NO: 55) than the TMV-RGD mutants. The collagen derived peptide inserts for TMV-DGEA was a minor improvement in comparison to the native TMV particles and TMV-P15 provided the strongest attachment for both cell lines among all of the mutants screened by the centrifugal assay. Additional mutations will be needed to determine ideal sequences for promoting stronger cell attachments.

The TMV mutants reported here incorporate longer flanking sequences than previously reported RGD peptide inserts displayed on viral particles. It is currently thought that the integrin specificity could rise from the difference between the flanking sequences surrounding the RGD motif, but also from the structural orientation of the ligand and the presence of other synergy site, such as the PHSRN (SEQ ID NO: 55) on fibronectin. The first isolated RGD mutant possesses the typical GRGDSPG (SEQ ID NO: 1) insert with only four additional amino acids to flank the binding site. The other RGD mutant contains a much longer 12 amino acid insert, based on the sequence of fibronectin with four amino acids flanking the amino and five amino acids flanking the carboxy end. Both of these RGD inserts are not displayed as a loop, but as a linear fragment displayed at the carboxy terminus of the TMV coat protein. Alternative mutation sites as well as circular permutations of the coat protein are potential routes to enclose these binding sites in a loop. The sequence, PHSRN (SEQ ID NO: 55), has been reported as the peptide fragment derived from the synergy site of fibronectin that promote the interaction between native fibronectin with its receptor, integrin $\alpha 5\beta 1$. Several reports have shown that RGDS (SEQ ID NO: 56) peptides often bind non-preferentially to several integrin receptors, making it difficult to control its effects on stem cells and tissue engineering scaffolds. In the crystal reconstructed image of fibronectin, these two sequences are also slightly at an off-angle, which might suggest that the positioning of the two regions could affect binding to the integrin receptor. Based on the crystal structure of TMV, we find that each carboxy region of the coat protein are separated by 2-3 nm, which is similar to the distance between the RGDS (SEQ ID NO: 56) and PHSRN (SEQ ID NO: 55) sequences along the native fibronectin. Whether the TMV mutant or other plant viruses can mimic this complex structural feature remains to be seen.

Despite the growing scientific interest in adapting the virus particles as nano-agents in biomedical applications, a key issue remains. How will these fare when introduced to the body? Manchester, Stuhlmann and colleagues have demonstrated that fluorescently labelled CPMV particles can circulate in animal hosts as potent vasculature imaging agents. Appending short polyethylene chains to shield the virus particles have also been suggested by researchers to avoid the host immune response. However, TMV is a powerful antigenic carrier that has been used to display high copy numbers of an epitope and activate cellular immune system to protect vaccinated animal hosts against lethal challenge of pathogens. Translating a virus-based vaccine agent as an implantable tissue scaffold will require a balance between recruiting stem cells to the scaffolds while repelling the macrophages and other immune cells. One possibility is by culturing the tissues ex-vivo with the virus scaffolds in serum-free, chemically defined cultures then transplanting the engineered tissue to the injury site. Due to its proteinaceous nature, majority of the TMV particles are likely degraded over time by the proteinases secreted by the cells. Our current studies have modelled the viruses in three-dimensional scaffolds, and initial studies suggest that such immunogenic responses can be avoided by proper timing of the ex vivo cultures and tissue implantation. As long as the virus provides an "electrical" jolt to jump start the stem cell differentiation process, followed by degradation of the virus particles and replacement by natural ECM proteins, the virus-based biomaterial may yet be a feasible concept for tissue engineering.

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged both in whole or in part. Furthermore, those of ordinary skill in the art will appreciate that the foregoing description is by way of example only, and is not intended to limit the invention so further described in the appended claims.

What is claimed:

1. A method of forming a hydrogel, the method comprising:
   forming modified Tobacco Mosaic Virus particles, the modification comprising including a cell binding motif on a carboxy end of a coat protein of the Tobacco Mosaic Virus particles;
   incorporating a plurality of the modified Tobacco Mosaic Virus particles into a hydrogel precursor formulation; and
   polymerizing the hydrogel precursor formulation to form a hydrogel matrix with the modified Tobacco Mosaic Virus particles incorporated therein.

2. The method of claim 1, wherein the hydrogel precursor formulation comprises a mixture of alginate in bicarbonate solution and a mild acid.

3. The method of claim 1, further comprising crosslinking the hydrogel matrix.

4. The method of claim 1, wherein the cell binding motif comprises an RGD tripeptide sequence derived from fibronectin.

5. The method of claim 1, wherein the cell binding motif comprises an RGD tripeptide sequence derived from vitronectin.

6. The method of claim 1, wherein the cell binding motif comprises an RGD tripeptide sequence derived from osteocalcin.

7. The method of claim 1, wherein the cell binding motif comprises a PHSRN (SEQ ID NO: 55) sequence derived from fibronectin.

8. The method of claim 1, wherein the cell binding motif comprises an DGEA (SEQ ID NO: 4) peptide sequence derived from collagen.

9. The method of claim 1, wherein the cell binding motif comprises a P15 peptide sequence derived from collagen.

10. The method of claim 1, wherein the cell binding motif is selected from the group consisting of GRGDSPG (SEQ ID NO: 1), AVTGRGDSPASS (SEQ ID NO: 2), EDRVPHSRNSIT (SEQ ID NO: 3), DGEA (SEQ ID NO: 4), and GTPGPQGIAGQRGVV (SEQ ID NO: 5).

11. The method of claim 1, further comprising maintaining the hydrogel in a serum-free environment supplemented with growth factors.

12. The method of claim 11, wherein the growth factors comprise a fibroblast growth factor, a transforming growth factor-beta 1, or an epidermal growth factor.

13. The method of claim 1, further comprising seeding the hydrogel with cells.

14. The method of claim 13, wherein upon the seeding, the cells bind to the virus particles.

15. The method of claim 1, wherein the method is free of covalent modification of the hydrogel.

16. A method of forming a hydrogel, the method comprising:
   incorporating a plurality of modified Tobacco Mosaic Virus particles into a hydrogel precursor formulation;
   polymerizing the hydrogel precursor formulation to form a hydrogel matrix with the modified Tobacco Mosaic Virus particles incorporated therein; and
   maintaining the hydrogel incorporating the modified Tobacco Mosaic Virus particles therein in a serum-free environment supplemented with growth factors.

17. The method of claim 16, wherein the growth factors comprise a fibroblast growth factor, a transforming growth factor-beta1, or an epidermal growth factor.

18. The method of claim 16, wherein the modified Tobacco Mosaic Virus particles comprise a cell binding motif on a carboxy end of a coat protein of the modified Tobacco Mosaic Virus particles.

19. A method of forming a hydrogel, the method comprising:
   incorporating a plurality of modified Tobacco Mosaic Virus particles into a hydrogel precursor formulation;
   polymerizing the hydrogel precursor formulation to form a hydrogel matrix with the modified Tobacco Mosaic Virus particles incorporated therein; and
   seeding the hydrogel incorporating the modified Tobacco Mosaic Virus particles therein with cells.

20. The method of claim 19, wherein upon the seeding, the cells bind to the modified Tobacco Mosaic Virus particles.

21. The method of claim 19, wherein the modified Tobacco Mosaic Virus particles comprise a cell binding motif on a carboxy end of a coat protein of the Tobacco Mosaic Virus particles.

* * * * *

SEQUENCE LISTING

```
<160> NUMBER OF SEQ ID NOS: 56

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Arg Gly Asp Ser Pro Gly
1               5

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ala Val Thr Gly Arg Gly Asp Ser Pro Ala Ser Ser
1               5                   10

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Asp Arg Val Pro His Ser Arg Asn Ser Ile Thr
1               5                   10
```

```
<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Gly Glu Ala
1

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Thr Pro Gly Pro Gln Gly Ile Ala Gly Gln Arg Gly Val Val
1               5                   10                  15

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Ala Gly Ser Gly Arg Gly Asp Ser Gly Ala
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Thr Gly Arg Gly Asp Ser Pro Ala Ser Ser
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Glu Pro Arg Gly Asp Thr Tyr Arg Ala
1               5                   10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9
```

Ala Gly Ser Gly Arg Gly Asp Ser Gly Ala
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Glu Pro Arg Gly Asp Thr Tyr Arg Ala Tyr
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Asn Gly Pro Arg Gly Asp Asn Tyr Arg Ala
1               5                   10

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ala Gly Ser Gly Glu Pro Arg Gly Asp Thr Tyr Arg Ala Ser Gly Ala
1               5                   10                  15

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Pro His Ser Arg Asn Gly
1               5

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Glu Asp Arg Val Pro His Ser Arg Asn Ser
1               5                   10

<210> SEQ ID NO 15
<211> LENGTH: 4
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 15

Asp Ser Pro Gly
1

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Thr Gly Arg Gly Asp Ser Pro Gly
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Ser Ser Gly Pro Ala Thr
1               5

<210> SEQ ID NO 18
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Ser Pro Ala Ser Ser Gly Pro Ala Thr
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Pro His Ser Arg Asn Ser Ile Thr Gly Pro Ala Thr
1               5                   10

<210> SEQ ID NO 20
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Asp Val Arg Pro His Ser Arg Asn Ser Ile Thr Gly Pro Ala Thr
1               5                   10                  15
```

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Glu Ala Gly Pro Ala Thr
1               5

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Pro Gln Gly Ile Ala Gly Gln Arg Gly Val Val Gly Pro Ala Thr
1               5                   10                  15

<210> SEQ ID NO 23
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
tctggtcctg caactggaag aggagactct ccaggatgag gtagtcaaga t          51

<210> SEQ ID NO 24
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
atcttgacta cctcatcctg gagagtctcc tcttccagtt gcaggaccag a          51

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agcggcagag gcgacagcgg cgccggtcct gcaacttgag gtagt                 45

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gctgtcgcct ctgccgctgc cggcaccaga ggtccaaacc aaacc                 45

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
agaggcgaca gccccgccag cagctgaggt agtcaagatg cataa            45

<210> SEQ ID NO 28
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28 ggcgggctg tcgcctctgc cggtagaggt ccaaaccaaa cc               42

<210> SEQ ID NO 29
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ggcgagccca gaggcgacac ctacagagcc tgaggtagtc aagatgcata a     51

<210> SEQ ID NO 30
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggctctgtag gtgtcgcctc tgggctcgcc agaggtccaa accaaacc         48

<210> SEQ ID NO 31
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
agcggcagag gcgacagcgg cgccggtcct gcaacttgag gtagt            45

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gctgtcgcct ctgccgctgc cggcagaggt ccaaaccaaa ccaga            45

<210> SEQ ID NO 33
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ccgagaggag atacatacag agcatacggt cctgcaactt gaggtagt                48

<210> SEQ ID NO 34
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
tctgtatgta tctcctctcg gctctccaga ggtccaaacc aaaccaga                48

<210> SEQ ID NO 35
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ggaagaggag attcaccggc atcatcaggt cctgcaactt gaggtagt                48

<210> SEQ ID NO 36
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cggtgaatct cctcttcctg tcactgcaga ggtccaaacc aaaccaga                48

<210> SEQ ID NO 37
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
aatggaccga gaggagataa ttacagagca ggtcctgcaa cttgaggt                48

<210> SEQ ID NO 38
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tctgtaatta tctcctctcg gtccattctc agaggtccaa accaaacc                48

```
<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
cgcggtgata cgtaccgtgc gagcggcgcc ggtcctgcaa cttga            45

<210> SEQ ID NO 40
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gtacgtatca ccgcgtggct ctccgctgcc ggcagaggtc caaaccaa         48

<210> SEQ ID NO 41
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tctggtcctg caactccaca ctctagaaat ggatgaggta gtcaagat         48

<210> SEQ ID NO 42
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
atcttgacta cctcatccat ttctagagtg tggagttgca ggaccaga         48

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
agagtgcccc acagcagaaa cagctgaggt agtcaagatg cataa            45

<210> SEQ ID NO 44
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tctgctgtgg ggcactctgt cctcagaggt ccaaaccaaa cc               42

<210> SEQ ID NO 45
```

```
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtgccgcact caaggaattc aataacgggt cctgcaactt gaggtagt                    48

<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
attccttgag tgcggcactc tatcctcaga ggtccaaacc aaaccaga                    48

<210> SEQ ID NO 47
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tggacctctg acggcgaggc cggtcctgca acttgaggt                              39

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
agcaggaccg gcctcgccgt cagaggtcca aaccaaacc                              39

<210> SEQ ID NO 49
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
agcggcagag gcgacagcgg cgccggtcct gcaacttgag gtagt                       45

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gctgtcgcct ctgccgctgc cggcagaggt ccaaaccaaa ccaga                       45

<210> SEQ ID NO 51
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cgtgcctgcg gatgtatatg aac                                          23

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
cgttatcgta cgcaccacgt gtg                                          23

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ser Gly Pro Ala Thr Gly Arg Gly Asp
1               5

<210> SEQ ID NO 54
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Ala Val Thr Gly Arg Gly Asp
1               5

<210> SEQ ID NO 55
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Pro His Ser Arg Asn
1               5

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Arg Gly Asp Ser
1
```